US008173984B2

(12) United States Patent
Moriya et al.

(10) Patent No.: US 8,173,984 B2

(45) Date of Patent: May 8, 2012

(54) EXTREME ULTRAVIOLET LIGHT SOURCE APPARATUS

(75) Inventors: Masato Moriya, Hiratsuka (JP); Tamotsu Abe, Hiratsuka (JP); Takashi Suganuma, Hiratsuka (JP); Hiroshi Someya, Hiratsuka (JP); Takayuki Yabu, Hiratsuka (JP); Akira Sumitani, Hiratsuka (JP); Osamu Wakabayashi, Hiratsuka (JP)

(73) Assignees: Komatsu Ltd., Tokyo (JP); Gigaphoton Inc., Tokyo (JP)

( * ) Notice: Subject to any disclaimer, the term of this patent is extended or adjusted under 35 U.S.C. 154(b) by 165 days.

(21) Appl. No.: 12/382,964

(22) Filed: Mar. 27, 2009

(65) Prior Publication Data

US 2010/0171049 A1 Jul. 8, 2010

(30) Foreign Application Priority Data

Jan. 6, 2009 (JP) ................................ 2009-000520

(51) Int. Cl.

*A61N 5/06* (2006.01)
*G01J 3/10* (2006.01)
*H05G 2/00* (2006.01)

(52) U.S. Cl. ................ 250/504 R; 250/423 R; 250/424; 250/425; 250/493.1; 250/494.1

(58) Field of Classification Search .............. 250/504 R, 250/423 R, 424, 425, 493.1, 494.1
See application file for complete search history.

(56) References Cited

U.S. PATENT DOCUMENTS

2005/0173375 A1* 8/2005 Mitrovic et al. ................ 216/60
2005/0199829 A1* 9/2005 Partlo et al. ............... 250/504 R
2010/0171049 A1* 7/2010 Moriya et al. ............ 250/504 R
2010/0176310 A1* 7/2010 Moriya et al. ............. 250/493.1
2010/0200776 A1* 8/2010 Yabu et al. ................ 250/504 R

FOREIGN PATENT DOCUMENTS

JP 2003-229298 8/2003
JP 2005-235959 9/2005

OTHER PUBLICATIONS

Japanese Office Action, w/ partial English translation thereof, issued in Japanese Patent Application No. 2006-275442, dated Sep. 20, 2011.

* cited by examiner

*Primary Examiner* — Jack Berman
*Assistant Examiner* — Meenakshi Sahu
(74) *Attorney, Agent, or Firm* — McDermott Will & Emery LLP

(57) ABSTRACT

An EUV light source apparatus can reliably detect and accurately judge deterioration of an optical element in a laser beam focusing optics disposed within an EUV light generation chamber. This EUV light source apparatus includes: the EUV light generation chamber; a target material supply unit; an EUV light collector mirror; a driver laser; a window; a parabolic mirror which focuses collimated laser beam by reflection and is disposed within the EUV light generation chamber; an energy detector detecting energy of the laser beam diffused without being applied to a target material after being focused by the laser beam focusing optics when the EUV light is not generated; and a processing unit for judging the deterioration of the window and the parabolic mirror according to the laser beam energy detected by the energy detector.

27 Claims, 37 Drawing Sheets

EXTREME ULTRAVIOLET LIGHT SOURCE APPARATUS

BACKGROUND OF THE INVENTION

1. Field of the Invention

The present invention relates to an LPP (laser produced plasma) type EUV (extreme ultraviolet) light source apparatus generating extreme ultraviolet light which is used for exposing a semiconductor wafer or the like.

2. Description of a Related Art

Recently, along with a finer semiconductor process, optical lithography has been making a rapid progress for realizing a finer pattern, and is now required to realize a fine process at 60 nm through 45 nm and further a fine process at 32 nm and beyond in the next generation. Accordingly, it is expected to develop, for example, an exposure equipment using a combination of an EUV light source generating extreme ultraviolet (EUV) light with a wavelength of approximately 13 nm and a reduced projection reflective system in order to cope with the fine process at 32 nm and beyond.

There are three types of EUV light sources including an LPP (laser produced plasma) light source using plasma which is generated by application of a laser beam onto a target, a DPP (discharge produced plasma) light source using plasma generated by discharge, and an SR (synchrotron radiation) light source using synchrotron orbital radiation light. Among these light sources, the LPP light source is considered to be a good candidate for the EUV lithography light source which is required to have a power of a hundred or more watts. This is because of advantages thereof such as one that the LPP light source can provide extremely high luminance close to that of black body radiation since plasma density can be made considerably high therein. The LPP light source also can emit only light within a desired waveband by selecting a target material, and forms a point light source which has an almost isotropic angular intensity distribution and provides an extremely great collection solid angle like $2\pi$ to $4\pi$ steradians, since there is no structure surrounding the light source such as electrodes.

FIG. 37 is a diagram showing an outline of a conventional LPP type EUV light source apparatus. As shown in FIG. 37, this EUV light source apparatus is configured with a driver laser 101, an EUV light generation chamber 102, a target material supply unit 103, and a laser beam focusing optics 104, as main constituents.

The driver laser 101 is an oscillation-amplification (Master Oscillator Power Amplifier) type laser apparatus generating drive laser beam used for exciting a target material.

The EUV light generation chamber 102 is a chamber in which the EUV light is generated, and is made vacuum therein by a vacuum pump 105 for turning the target material easily into plasma and preventing the EUV light from being absorbed. In addition, the EUV light generation chamber 102 is provided with a window 106 attached thereto for transmitting a laser beam 120 generated in the driver laser 101 to the inside of the EUV light generation chamber 102. Further, a target injection nozzle 103*a*, a target collection cylinder 107, and an EUV light collector mirror 108 are disposed within the EUV light generation chamber 102.

The target material supply unit 103 supplies a target material used for generating the EUV light to the inside of the EUV light generation chamber 102 via the target material injection nozzle 103*a* which is a part of the target material supply unit 103. The target collection cylinder 107A collects a remaining part of the supplied target material, which becomes unnecessary without being irradiated with the laser beam.

The laser light focusing optics 104 includes a mirror 104*a* reflecting the laser beam 120 emitted from the driver laser 101 in the direction of the EUV light generation chamber 102, a mirror adjustment mechanism 104*b* adjusting the position and angle (tilt angle) of the mirror 104*a*, a collector element 104*c* focusing the laser beam 120 reflected by the mirror 104*a*, and a collector element adjustment mechanism 104*d* moving the collector element 104*c* along the optical axis of the laser beam. The laser beam 120 focused by the laser beam focusing optics 104 is transmitted through the window 106 and a hole formed in the center part of the EUV light collector mirror 108 and reaches a path of the target material. In this manner, the laser beam focusing optics 104 focuses the laser beam 120 so as to form a focus on the path of the target material. Thereby, the target material 109 is excited into plasma and an EUV light 121 is generated.

The EUV light collector mirror 108 is a concave mirror which has a Mo/Si film formed on the surface thereof for reflecting light with a wavelength of 13.5 nm, for example, in a high reflectance, and focuses the generated EUV light 121 to an IF (intermediate focusing point) by the reflection. The EUV light 121 reflected by the EUV light collector mirror 108 is transmitted through a gate valve 110 provided to the EUV light generation chamber 102 and a filter 111 which eliminates unnecessary light (electromagnetic wave (light) with a wavelength shorter than the EUV light and light with a wavelength longer than the EUV light (e.g., ultraviolet light, visible light, infrared light, etc.)) from the light generated from the plasma and transmits only the desired EUV light (e.g., light with a wavelength of 13.5 nm). After that, the EUV light 121 focused on the IF point (intermediate focusing point) is guided to an exposure unit or the like via a transmission optics.

Large energy is radiated from the plasma generated within the EUV light generation chamber 102, and this radiation increases the temperature of the components within the EUV light generation chamber 102. There is known a technique preventing such a temperature rise of the components.

For example, Japanese Patent Application Laid-Open Publication No. 2003-229298A discloses an X-ray generation apparatus including an X-ray source which turns a target material into plasma and radiates an X-ray from the plasma, and a vacuum chamber which accommodates the X-ray source, wherein an inner wall formed with a material having a high absorption rate for an electromagnetic wave in the range from infrared light to an X-ray is provided within the vacuum chamber. In this X-ray generation apparatus, it is possible to prevent the components within the vacuum chamber from being unnecessarily heated by the radiation energy which is reflected and scattered by the inner wall of the vacuum chamber.

Meanwhile, the plasma generated within the EUV light generation chamber 102 shown in FIG. 37 is diffused as time elapses and a portion thereof flies apart as atoms and ions. These atoms and ions are called debris and radiated to the inner wall and a structure within the EUV light generation chamber 102.

The following phenomena can be caused by the above radiation of the debris flying from the plasma and the electromagnetic wave radiated from the plasma.

(a) The atoms flying from the plasma adhere to the surface of the window 106 on the inner side of the EUV light generation chamber 102. The laser beam 120 is absorbed by the atoms adhered to the surface of the window 106 on the inner side of the EUV light generation chamber 102 in this manner.

(b) The ions flying from the plasma are radiated to the surface of the window 106 on the inner side of the EUV light generation chamber 102 and the surface of the window 106 on the inner side of the EUV light generation chamber 102 is deteriorated (the surface is made rough and becomes unsmooth). Thereby, the window 106 becomes to absorb the laser beam 120 emitted from the driver laser 101.

(c) The ions flying from the plasma are radiated to the inner wall and the structure of the EUV light generation chamber 102. By the sputtering, the atoms flying from the inner wall and the structure of the EUV light generation chamber 102 adhere to the window 106 on the inner side of the EUV light generation chamber 102. The laser beam 120 is absorbed by the atoms adhered to the window 106 on the inner side of the EUV light generation chamber 102 in this manner.

(d) The material of the window 106 is deteriorated by the absorption of an electromagnetic wave (light) generated from the plasma and having a short wavelength. Thereby, the window 106 becomes to absorb the laser beam 120.

(e) When the operation period of the EUV light source apparatus becomes long to some extent, the material of the window 106 is deteriorated or damaged by application of the laser beam 120 during the operation period. Thereby, the window 106 becomes to absorb the laser beam 120.

Occurrences of the phenomena of above (a) to (e) cause reduction in energy for turning the target material into plasma and reduction in generation efficiency of the EUV light 121.

In addition, when the window 106 and the atoms adhered to the window 106 absorb the laser beam 120, the temperature of the window 106 increases and the substrate (base material) of the window 106 is distorted, resulting in reduction of the beam focusing capability. Such a reduction of the beam focusing capability invites a further reduction in the generation efficiency of the EUV light 121. Further, the large distortion in the substrate of the window 106 finally invites the breakage of the window 106.

Note that a part of the laser beam focusing optics 104 (e.g., lens, mirror, etc.) is sometimes disposed within the EUV light generation chamber 102. In such a case, the above phenomena of (a) to (e) can be caused also in the part of the laser beam focusing optics 104 disposed within the EUV light generation chamber 102. In particular, in the case that the mirror reflecting the laser beam is disposed within the EUV light generation chamber 102, the above phenomena of (a) to (e) caused in the mirror reduces a laser beam reflectance of a reflection enhancement coating on the reflection surface of the mirror. Thereby, the energy for turning the target material into plasma is reduced and the generation efficiency of the EUV light 121 is reduced.

When the above phenomena of (a) to (e) occur and the window 106 or the laser beam focusing optics 104 is deteriorated, it is necessary to replace the deteriorated optical element with a new optical element.

However, since the laser beam 120 is focused onto the plasma generation position (onto the path of the target material) within the EUV light generation chamber 102, there arises a problem that it is difficult to know whether the window 106 or the laser beam focusing optics 104 is deteriorated or not and to take a rapid response action (replacement of the optical element).

Meanwhile, in addition to the deterioration of the window 106 or the laser beam focusing optics 104, a focusing position (focus) shift of the laser beam 120 is pointed out as a factor inviting instability of the plasma generation and finally changing or reducing the generation efficiency of the EUV light 121. The focusing position shift of the laser beam 120 is caused by an alignment shift of the laser beam focusing optics 104, a pointing shift of the driver laser 101, or the like. The alignment shift of the laser beam focusing optics 104 is mainly caused when an optical element included in the laser beam focusing optics 104 or an optical element holder holding such an optical element bears a thermal burden and the optical element or the optical element holder is deformed, along with the operation of the EUV light source apparatus. Further, the pointing shift of the driver laser 101 is mainly caused when an element or a component within the driver laser 101 bears a thermal burden and the element or the composition member is deformed along with the operation of the EUV light source apparatus.

When the focusing position shift of the laser beam 120 is caused as described above, a focusing spot size or an intensity distribution becomes inappropriate at the plasma generation position (on the path of the target material), or the laser beam 120 is deflected from the target material. Thereby, instability of the plasma generation is invited finally resulting in variation or reduction in the generation efficiency of the EUV light 121.

Note that the focusing position shift of the laser beam 120 can be repaired by readjustment of the alignment in the laser beam focusing optics 104, without replacing the optical element. Thereby, the focusing position of the laser beam 120 can be returned to the original position (plasma generation position) and it is possible to stabilize the plasma generation and resultantly to recover the generation efficiency of the EUV light 121 to the original value.

However, since the laser beam 120 is focused to the inside of the EUV light generation chamber 102 (plasma generation position), there is a problem that it is difficult to know whether the focusing position of the laser beam 120 is shifted or not, and to take a rapid response action (readjustment of the alignment in the laser beam focusing optics 104).

SUMMARY OF THE INVENTION

Accordingly, in view of the above problem, an object of the present invention is to provide an extreme ultraviolet light source apparatus in which it is possible to take a rapid action against reduction or variation of an EUV light generation efficiency caused by deterioration or the like of a window and/or a laser beam focusing optics in an EUV light generation chamber.

In order to achieve the above object, an extreme ultraviolet light source apparatus according to one aspect of the present invention is an apparatus for generating extreme ultraviolet light from plasma by applying a laser beam to a target material and thereby turning the target material into plasma, and the apparatus includes:

an extreme ultraviolet light generation chamber, in which the extreme ultraviolet light is generated;

a target material supply unit for injecting the target material into the extreme ultraviolet light generation chamber when the extreme ultraviolet light is generated;

a driver laser for emitting the laser beam;

a window provided to the extreme ultraviolet light generation chamber, and for transmitting the laser beam into the extreme ultraviolet light generation chamber;

a laser beam focusing optics including at least one optical element, and for focusing the laser beam emitted from said driver laser onto a path of the target material injected into said extreme ultraviolet light generation chamber to generate said plasma;

an extreme ultraviolet light focusing optics for focusing and emitting the extreme ultraviolet light generated from the plasma;

a laser beam detector provided outside the extreme ultraviolet light generation chamber, and for detecting an intensity of the laser beam diffused without being applied to the target material after being focused by the laser beam focusing optics, and being emitted from the extreme ultraviolet light generation chamber, when the extreme ultraviolet light is not generated; and a processing unit for judging deterioration of the window and/or the at least one optical element according to the intensity of the laser beam detected by the laser beam detector, when the extreme ultraviolet light is not generated.

DESCRIPTION OF THE PREFERRED EMBODIMENTS

Hereinafter, the preferred embodiments for implementing the present invention will be described in detail with reference to the drawings. Note that the same constituent is denoted by the same reference symbol and description thereof will be omitted.

Figure 1:
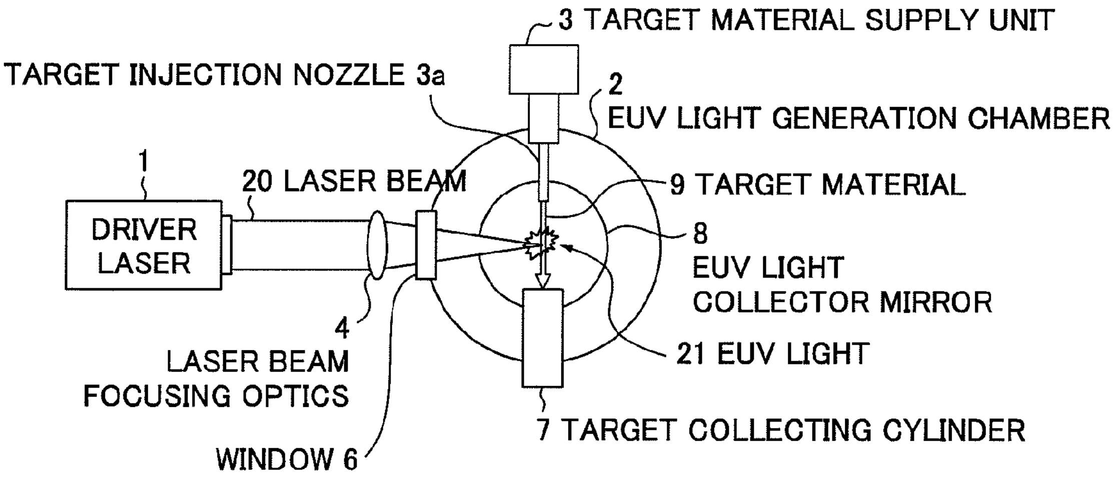
FIG. 1 is a schematic diagram showing an outline of an EUV light source apparatus according to the present invention.

FIG. 1 is a schematic diagram showing an outline of an extreme ultraviolet light source apparatus (hereinafter, also simply called "EUV light source apparatus") according to the present invention. As shown in FIG. 1, this EUV light source apparatus includes a driver laser 1, an EUV light generation chamber 2, a target material supply unit 3, and a laser beam focusing optics 4.

The driver laser 1 is an oscillation-amplification type laser apparatus generating dive laser beam used for exciting the target material. Various lasers known in public (e.g., ultraviolet laser such as KrF and XeF or infrared laser such as Ar, $CO_2$, and YAG) can be used for the driver laser 1.

The EUV light generation chamber 2 is a vacuum chamber in which the EUV light is generated. A window 6 is attached to the EUV light generation chamber 2 for transmitting the laser beam 20 generated by the driver laser 1 therethrough into the EUV light generation chamber 2. Further, a target injection nozzle 3*a*, a target collection cylinder 7, and an EUV light collector mirror 8 are disposed within the EUV light generation chamber 2.

The target material supply unit 3 supplies the target material used for generating the EUV light to the inside of the EUV light generation chamber 2 via the target injection nozzle 3*a* which is a unit of the target material supply unit 3. A part of the supplied target material which becomes unnecessary without being irradiated with the laser beam is collected by the target collection cylinder 7. Various materials known in public (e.g., tin (Sn), xenon (Xe), etc.) can be used for the target material. Further, the state of the target material may be any of solid, liquid, and gas, and the target material may be supplied to a space within the EUV light generation chamber 2 in any publicly known state such as a continuous flow (target jet flow) and liquid drops (droplets). For example, in the case of using a liquid xenon (Xe) target for the target material, the target material supply unit 3 is configured with a gas cylinder supplying high purity xenon gas, a mass flow controller, a refrigeration unit for liquefying the xenon gas, the target injection nozzle, etc. Further, in the case of generating droplets, a vibration device such as a piezoelectric element is added to the above configuration.

Note that the target material supply unit 3 supplies the target material to the inside of the EUV light generation chamber 2 when the EUV light source apparatus generates the EUV light, and does not supply the target material to the inside of the EUV light generation chamber 2 when the EUV light source apparatus does not generate the EUV light.

The laser beam focusing optics 4 focuses the laser beam 20 emitted from the driver laser 1 so as to form a focus on the path of the target material. Thereby, the target material 9 is excited into plasma and the EUV light 21 is generated. Note that the laser beam focusing optics 4 can be configured with a single optical element (e.g., one convex lens) and also with a plurality of optical elements. In the case that the laser beam focusing optics 4 is configured with the plurality of optical elements, some of the optical elements can be disposed within the EUV light generation chamber 2.

The EUV light collector mirror 8 is a concave mirror having a Mo/Si film on the surface thereof for reflecting light with wavelength of 13.5 nm, for example, in a high reflectance, and collects the generated EUV light 21 by reflection to guide the EUV light 21 to a transmission optics. This EUV light 21 is guided further to an exposure unit or the like via the transmission optics. Note that the EUV light collector mirror 8 shown in FIG. 1 collects the EUV light 21 in the front direction of the page.

(First Embodiment)

Next, an EUV light source apparatus according to a first embodiment of the present invention will be described.

Figure 2:
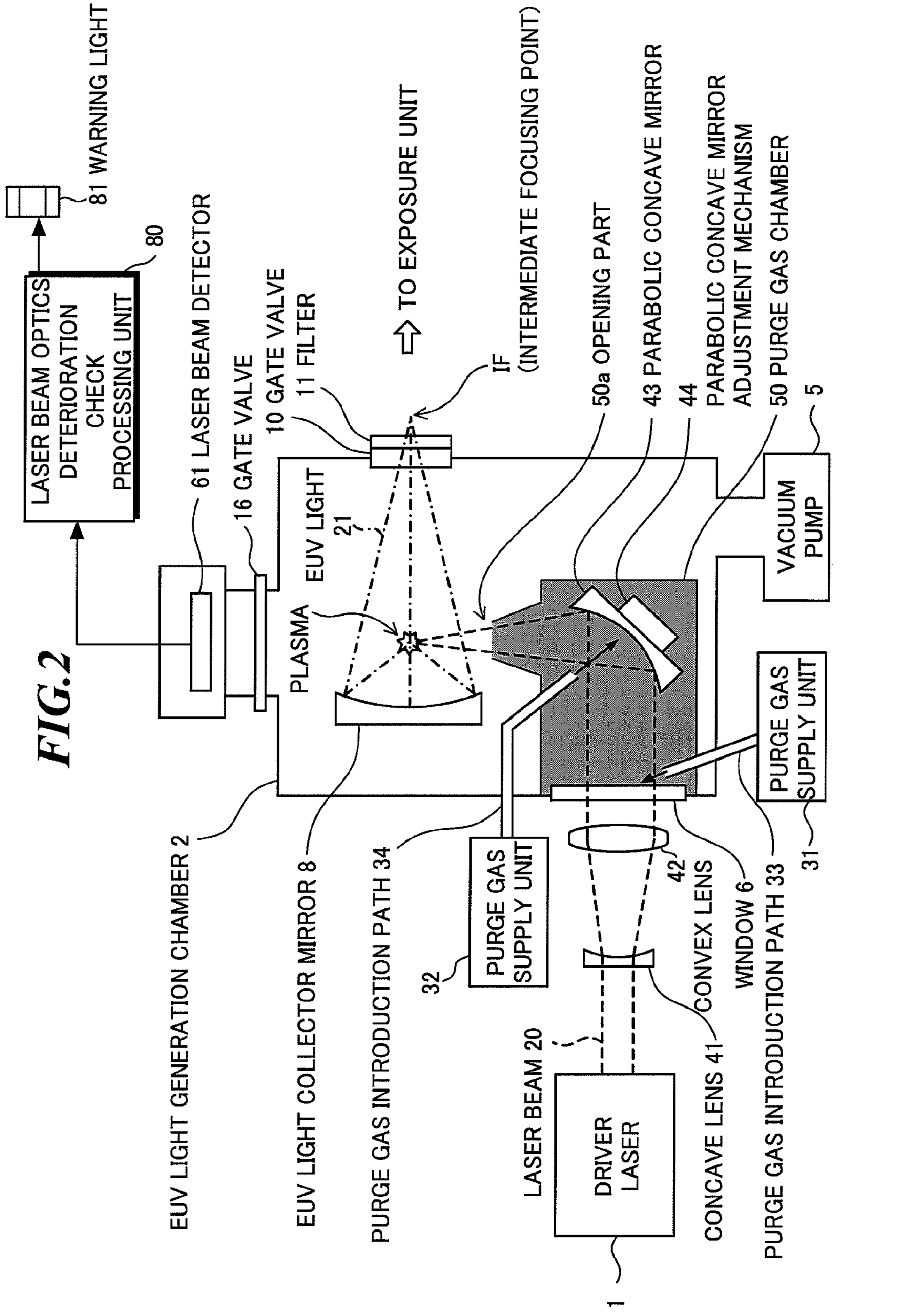
FIG. 2 is a schematic diagram showing a state of EUV light generation in an EUV light source apparatus according to a first embodiment of the present invention.
Figure 3:
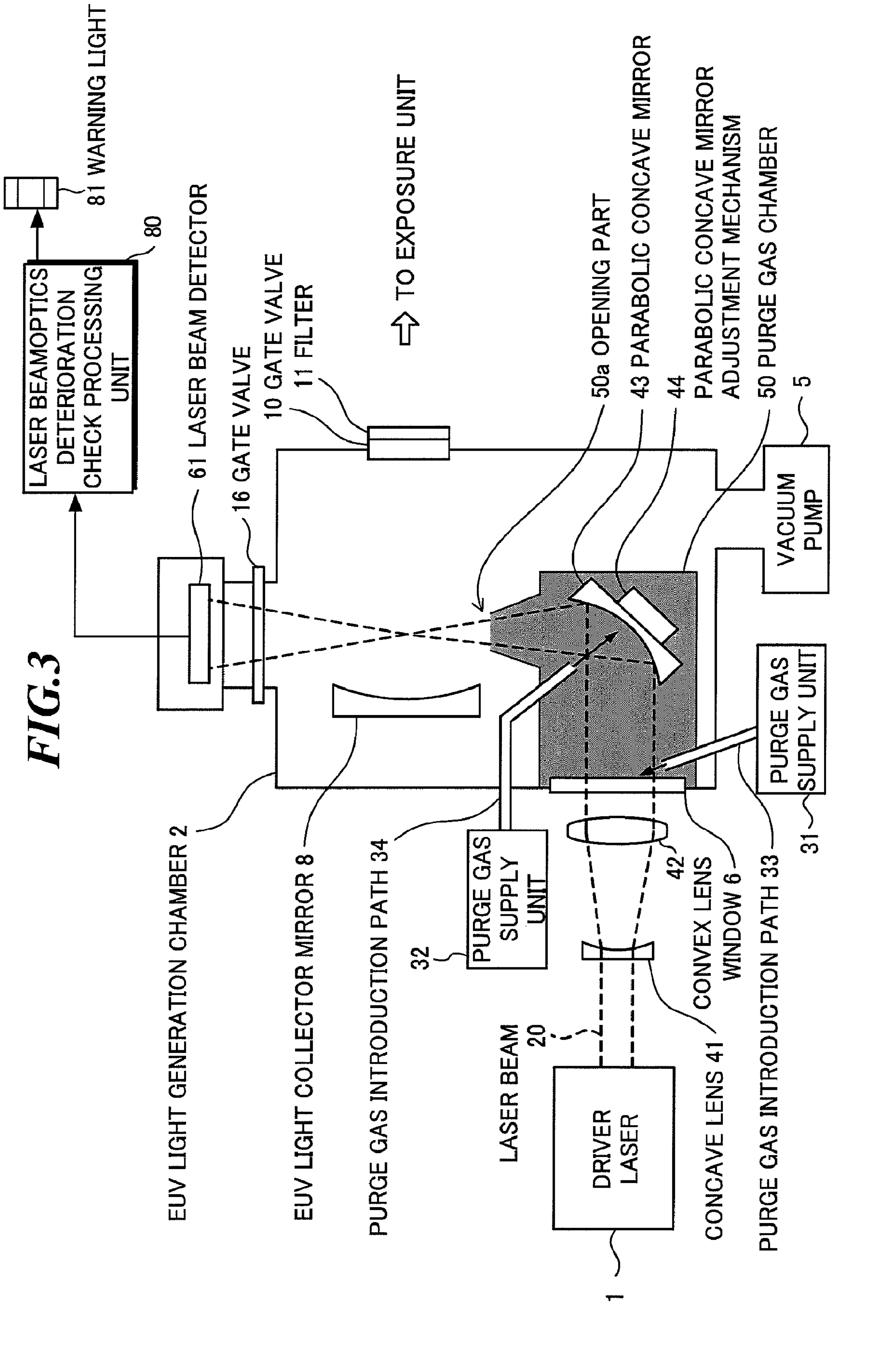
FIG. 3 is a schematic diagram showing a state without EUV light generation in the EUV light source apparatus according to the first embodiment of the present invention.

FIG. 2 and FIG. 3 are schematic diagrams showing the EUV light source apparatus according to the present embodiment. FIG. 2 is a schematic diagram showing a state when the EUV light source apparatus according to the present embodiment generates the EUV light, and FIG. 3 is a schematic diagram showing a state when the EUV light source apparatus according to the present embodiment does not generate the EUV light. Note that FIG. 2 and FIG. 3 omit the target material supply unit 3 and the target material collecting cylinder 7 (refer to FIG. 1) from the drawings, and the target material is assumed to be injected in the direction perpendicular to the page.

First, mainly with reference to FIG. 2, the operation of the EUV light source apparatus according to the present embodiment will be described for a case of the EUV light generation, and then, mainly with reference to FIG. 3, the operation of the EUV light source apparatus according to the present embodiment will be described for a case without the EUV light generation.

As shown in FIG. 2, the laser beam 20 emitted from the driver laser 1 in the right direction of the drawing is diffused by a concave lens 41, and collimated by a convex lens 42, and passes through the window 6, and inputs into the EUV light generation chamber 2. Note that, for the material of the concave lens 41, the convex lens 42, and the window 6, it is preferable to use a material absorbing little of the laser beam 20 such as synthetic quartz, $CaF_2$, and $MgF_2$. When the infrared laser such as $CO_2$ laser is used for the driver laser 1, ZnSe, GaAs, Ge, Si, etc. are suitable for the material of the concave lens 41, the convex lens 42, and the window 6. Further, it is preferable to provide an anti-reflection (AR) coating of a dielectric multilayer film on each surface of the concave lens 41, the convex lens 42, and the window 6.

A parabolic concave mirror 43, and a parabolic concave mirror adjustment mechanism 44 adjusting the position and angle (tilt angle) of the parabolic concave mirror 43 are disposed within the EUV light generation chamber 2. For the substrate material of the parabolic concave mirror 43, it is possible to use synthetic quartz, CaF2, Si, Zerodur (registered trade mark), Al, Cu, Mo, or the like, and it is preferable to provide a reflection coating of a dielectric multi layer film on the surface of such a substrate.

Figure 4A:
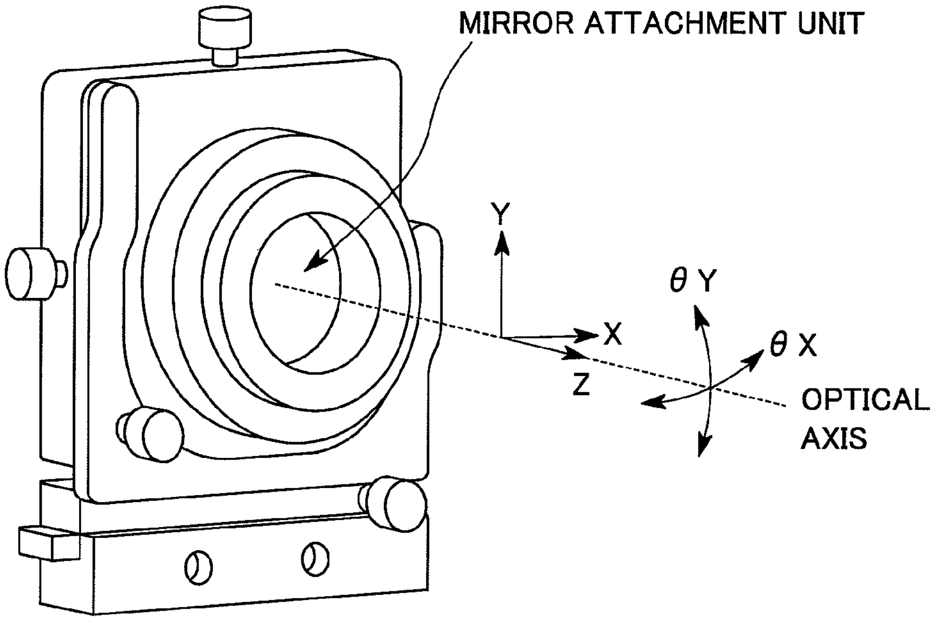
FIGS. 4A and 4B are schematic diagrams showing examples of a parabolic concave mirror adjustment mechanism in FIG. 2 and FIG. 3.
Figure 4B:
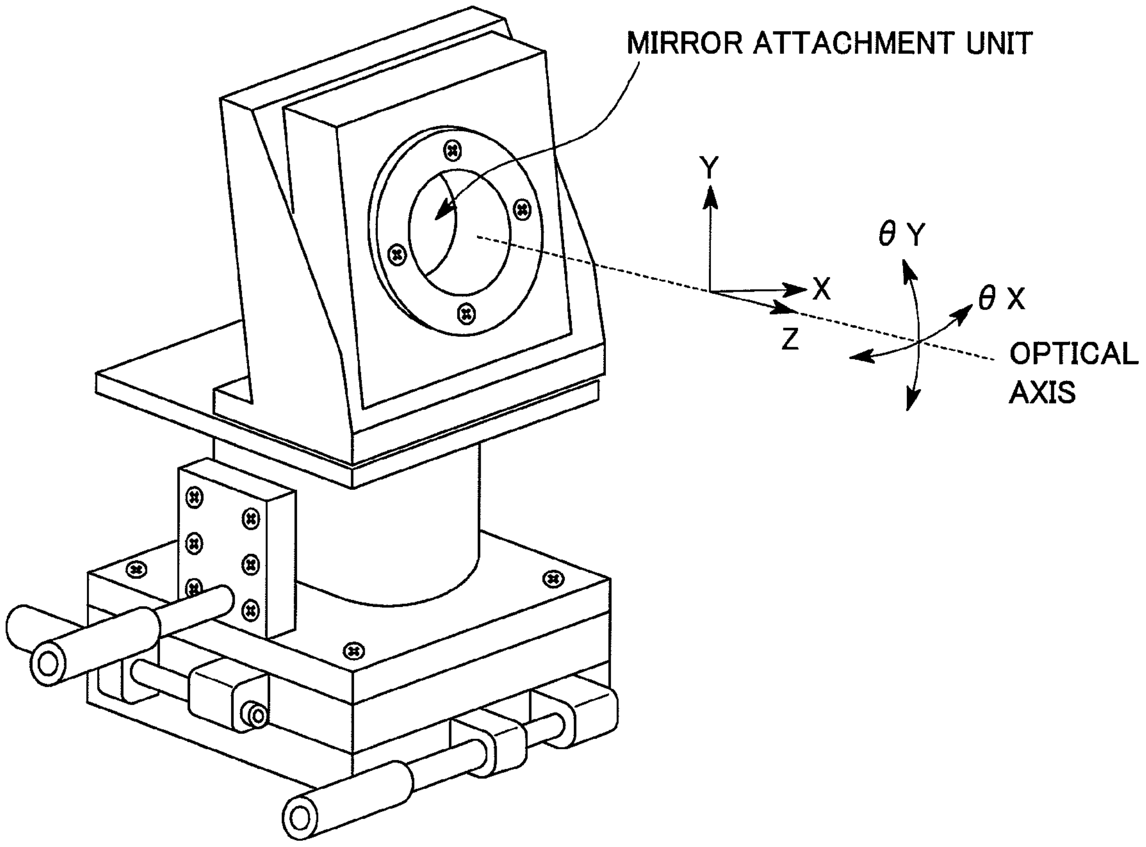

FIGS. 4A and 4B are diagrams showing examples of the parabolic concave mirror adjustment mechanism 44. As shown in FIGS. 4A and 4B, for adjusting an optical axis angle of the laser beam, the parabolic concave mirror adjustment mechanism 44 preferably can adjust tilt angles of the parabolic concave mirror 43 in the $\theta x$ direction and $\theta y$ direction of the drawing and also can move the parabolic concave mirror 43 in the x-axis direction, y-axis direction, and z-axis direction of the drawing while maintaining the tilt angles of the parabolic concave mirror 43.

With another reference to FIG. 2, the laser beam 20, which passes though the window 6 and inputs into the EUV light generation chamber 2, is reflected by the parabolic concave mirror 43 in the upper direction of the drawing and focused on the path of the target material. Thereby, the target material is excited into plasma and the EUV light 21 is generated.

Note that it is possible to make length of a back focus longer than its focal length by focusing the incident light after diffusing the incident light once. Such an optics is called a retro-focus optics.

The EUV light collector mirror 8 is a concave mirror, for example, having a Mo/Si film on the surface thereof for reflecting a light with wavelength of 13.5 nm in high reflectance, and reflects the generated EUV light 21 in the right direction of the drawing to focus the EUV light 21 onto the IF (intermediate focusing point). The EUV light 21, which is reflected by the EUV light collector mirror 8, passes through a gate valve 10 which is provided to the EUV generation chamber 2, and a filter 11 which eliminates unnecessary light (electromagnetic wave (light) with wavelength shorter than that of the EUV light and light having a longer wavelength than that of the EUV (e.g., ultraviolet light, visible light, infrared light, etc.)) from the light generated from the plasma and is passed through only with the desired EUV light (e.g., light with a wavelength of 13.5 nm). The EUV light 21 focused onto the IF (intermediate focusing point) is guided subsequently to the exposure unit or the like via the transmission optics.

This EUV light source apparatus further includes purge gas supply units 31 and 32 for injecting and supplying purge gasses, respectively, a purge gas introduction path 33 for introducing the purge gas injected from the purge gas supply unit 31 to the window 6 on the surface inside the EUV light generation chamber 2, and a purge gas introduction path 34 for introducing the purge gas injected from the purge gas supply unit 32 to the reflection surface of the parabolic concave mirror 43. For the purge gas, it is preferable to use inert gas (e.g., Ar, He, $N_2$, Kr, or the like).

Note that, when the EUV light source apparatus does not generate the EUV light, the purge gas supply units 31 and 32 may not inject the purge gasses, respectively.

Further, a purge gas chamber 50 is attached to the inner wall of the EUV light generation chamber 2 so as to surround the window 6, the parabolic concave mirror 43, and the parabolic concave mirror adjustment mechanism 44. The purge gas chamber 50 has a tapered cylindrical shape at the upper part thereof in the drawing, and is provided with an opening part 50*a* for letting pass the laser beam 20 through which is reflected by the parabolic concave mirror 43 at the top thereof (upper part in the drawing).

Further, a gate valve 16 is disposed at the upper part of the EUV light generation chamber 2 in the drawing. The gate valve 16 is closed when the EUV light source apparatus generates the EUV light (refer to FIG. 2) and opened when the EUV light source apparatus does not generate the EUV light (refer to FIG. 3). Thereby, in the case that the EUV light source apparatus generates the EUV light, the plasma, materials which fly apart when the plasma whittles (sputters) the inner wall of the EUV light generation chamber 2, or the like, and electromagnetic waves including the EUV light are blocked by the gate valve 16 as shielding means, and are not emitted to the outside of the EUV light generation chamber 2.

Next, with reference to FIG. 3, the operation of the EUV light source apparatus according to the present embodiment will be described for a case without the EUV light generation.

When the EUV light source apparatus does not generates the EUV light, as described herein above, the target material supply unit 3 does not supply the target material to the inside of the EUV light generation chamber 2, and the gate valve 16 is opened. Thereby, the laser beam focused by the parabolic concave mirror 43 is not applied to the target material and passes through the gate valve 16, while being diffused, to be emitted from the EUV light generation chamber 2 in the upper direction of the drawing.

At the upper part of the gate valve 16 in the drawing, a laser beam detector 61 is disposed for detecting the laser beam which passes through the gate valve 16 and is emitted from the EUV light generation chamber 2. For the laser beam detector 61, it is preferable to use a pyro-electric (pyro) sensor from a view point of resistance against a laser beam.

The laser beam, which has passed through the gate valve 16, is input into the laser beam detector 61, and the laser beam detector 61 detects the intensity of the incident laser beam. A signal or data representing the laser beam intensity detected by the laser beam detector 61 is sent to a laser beam optics deterioration check processing unit 80 which carries out processing for judging whether the window 6 and/or the parabolic concave mirror 43 is deteriorated or not. Note that the laser beam optics deterioration check processing unit 80 can be realized by a personal computer (PC) and a program. The laser beam optics deterioration check processing unit 80 is connected with a warning light 81 notifying user (operator) of the deterioration when the window 6 and/or the parabolic concave mirror 43 is deteriorated.

Figure 5:
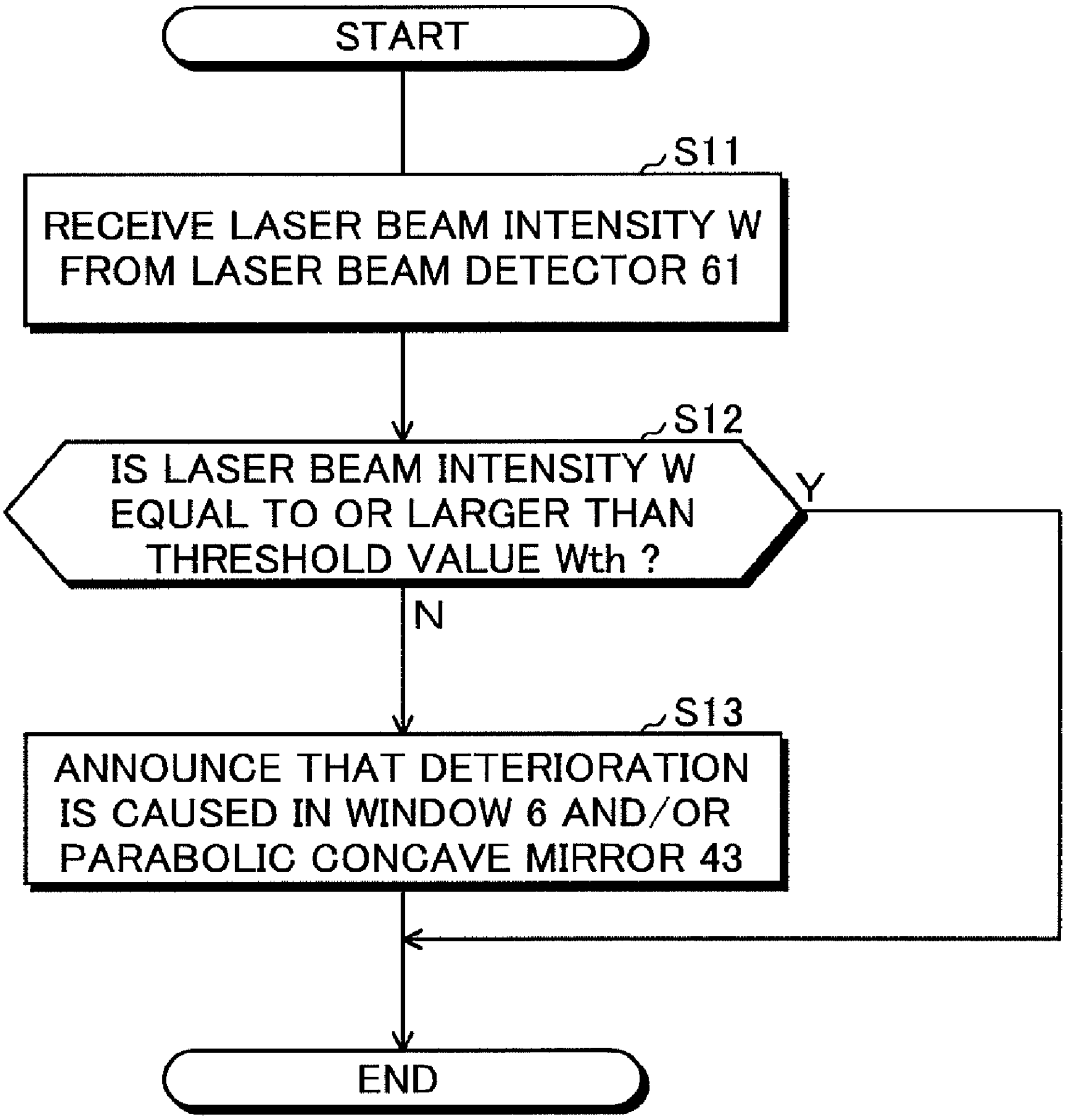
FIG. 5 is a flowchart showing processing carried out by a laser beam optics deterioration check processing unit in FIG. 2 and FIG. 3.

FIG. 5 is a flowchart showing the processing carried out by the laser beam optics deterioration check processing unit 80. The laser beam optics deterioration check processing unit 80 carries out the processing shown in FIG. 5 when the EUV light source apparatus does not generate the EUV light.

First, the laser beam optics deterioration check processing unit 80 receives the signal or data representing laser beam intensity W from the laser beam detector 61 (Step S11).

As described above, the deterioration of the window 6 reduces a transmittance of the laser beam 20 for the transmission through the window 6 and thereby reduces the laser beam intensity to be input into the EUV light generation chamber 2. Further, the deterioration in the reflection surface of the parabolic concave mirror 43 reduces a reflectance of the parabolic concave mirror 43 to reflect the laser beam, and thereby reduces the intensity of the laser beam to be applied to the target material.

Accordingly, in Step S12, the laser beam optics deterioration check processing unit 80 checks whether the laser beam intensity W is equal to or more than a predetermined threshold value Wth, and then determines that the deterioration is not caused in the window 6 or the parabolic concave mirror 43 and terminates the processing, if the laser beam intensity W is equal to or more than the predetermined threshold value Wth. On the other hand, if the laser beam intensity W is not equal to nor more than the predetermined threshold value Wth, the laser beam optics deterioration check processing unit 80 determines that the deterioration is caused in the window 6 and/or the parabolic concave mirror 43 and advances the process to Step S13. Note that, if the laser beam intensity W is equal to or more than the predetermined threshold value Wth, the process may be returned to Step S11 and the laser beam intensity check may be carried out repeatedly.

Then, if the laser beam intensity W is not equal to nor more than the predetermined threshold value Wth, that is, when the deterioration is determined to be caused in the window 6 and/or the parabolic concave mirror 43, the laser beam optics deterioration check processing unit 80 notifies the user (operator) of the deterioration (Step S13). Note that the notification may be carried by turning-on, blinking, or change of a blinking pattern of the warning light 81 about the deterioration caused in the window 6 and/or the parabolic concave mirror 43. Further, the notification may be carried out by sounding of a buzzer or the like, or may be carried out by displaying of characters or an image on a display device such as an LCD.

In this manner, according to the present embodiment, it is possible to easily detect that the window 6 and/or the parabolic concave mirror 43 is deteriorated and to notify the user (operator) of the deterioration, in the state without the EUV generation, and thereby the user (operator) can grasp appropriately whether or not to replace the window 6 and/or the parabolic concave mirror 43. Accordingly, it becomes possible to generate the EUV light stably.

Further, in the present embodiment, the gate valve 16 is closed when the EUV light source apparatus generates the EUV light (FIG. 2), and thereby it is possible to prevent the laser beam detector 61 from being destroyed by the plasma, materials which fly apart when the plasma whittles (sputters) the inner wall of the EUV light generation chamber 2, or the like, or the EUV light.

Note that, in order to adjust the alignment (position and tilt angle) of the parabolic concave mirror 43 close to a design value, it is preferable to assemble the concave mirror 41, the convex mirror 42, the window 6, and the parabolic concave mirror 43 integrally into a unit, and to complete the alignment of the parabolic concave mirror 43 before assembling this unit into the EUV light generation chamber 2, so as to obtain a design performance of the laser beam focusing.

Moreover, while two lenses (concave lens 41 and convex lens 42) are used in the present embodiment, three or more lenses may be used. Further, intensity of the laser beam input into the laser beam detector 61 may be adjusted by an ND (Neutral Density: attenuation) filter disposed in the optical path between the gate valve 16 and the laser beam detector 61.

(Second Embodiment)

Next, an EUV light source apparatus according to a second embodiment of the present invention will be described.

Figure 6:
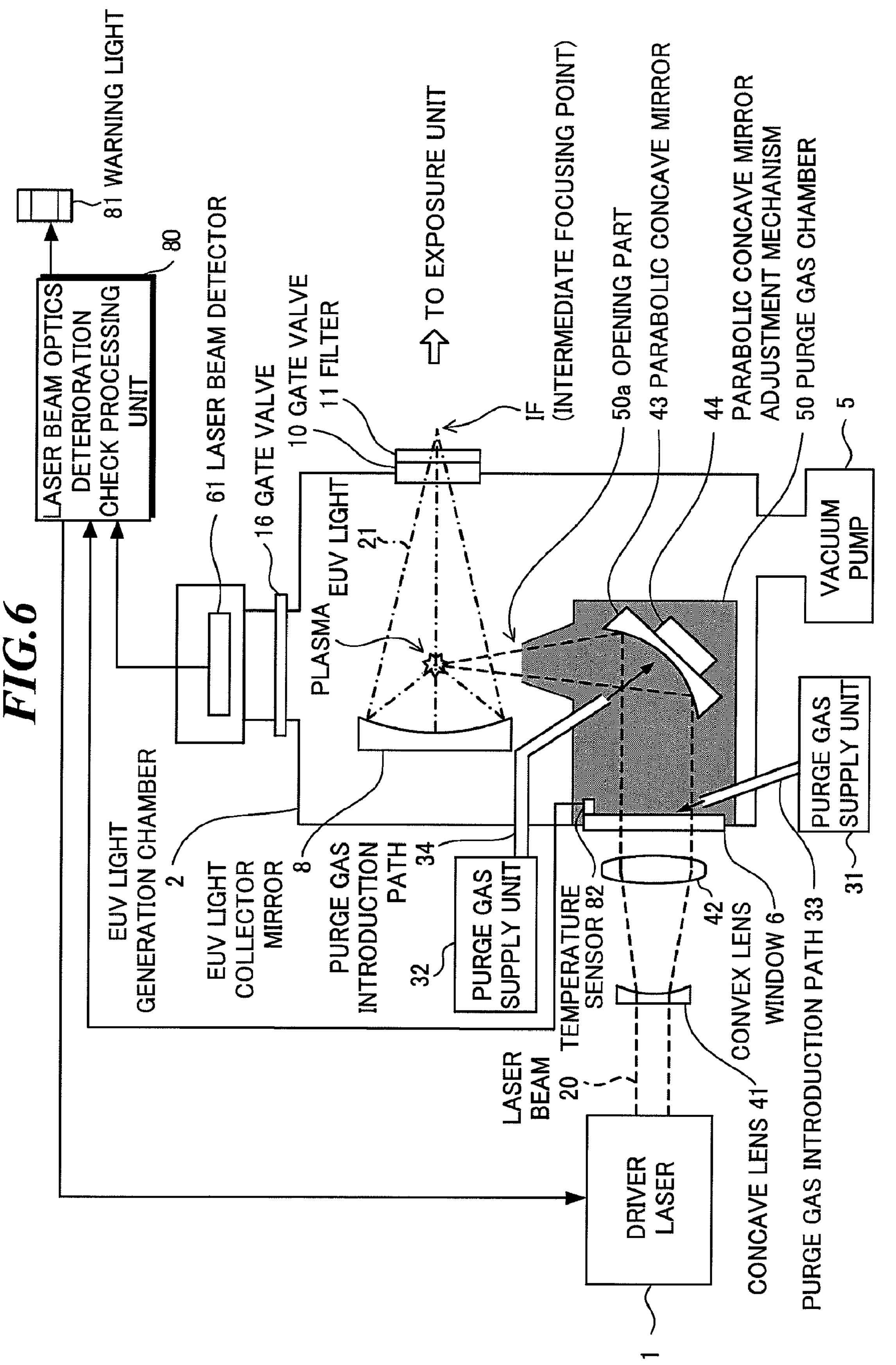
FIG. 6 is a schematic diagram showing a state of EUV light generation in an EUV light source apparatus according to a second embodiment of the present invention.
Figure 7:
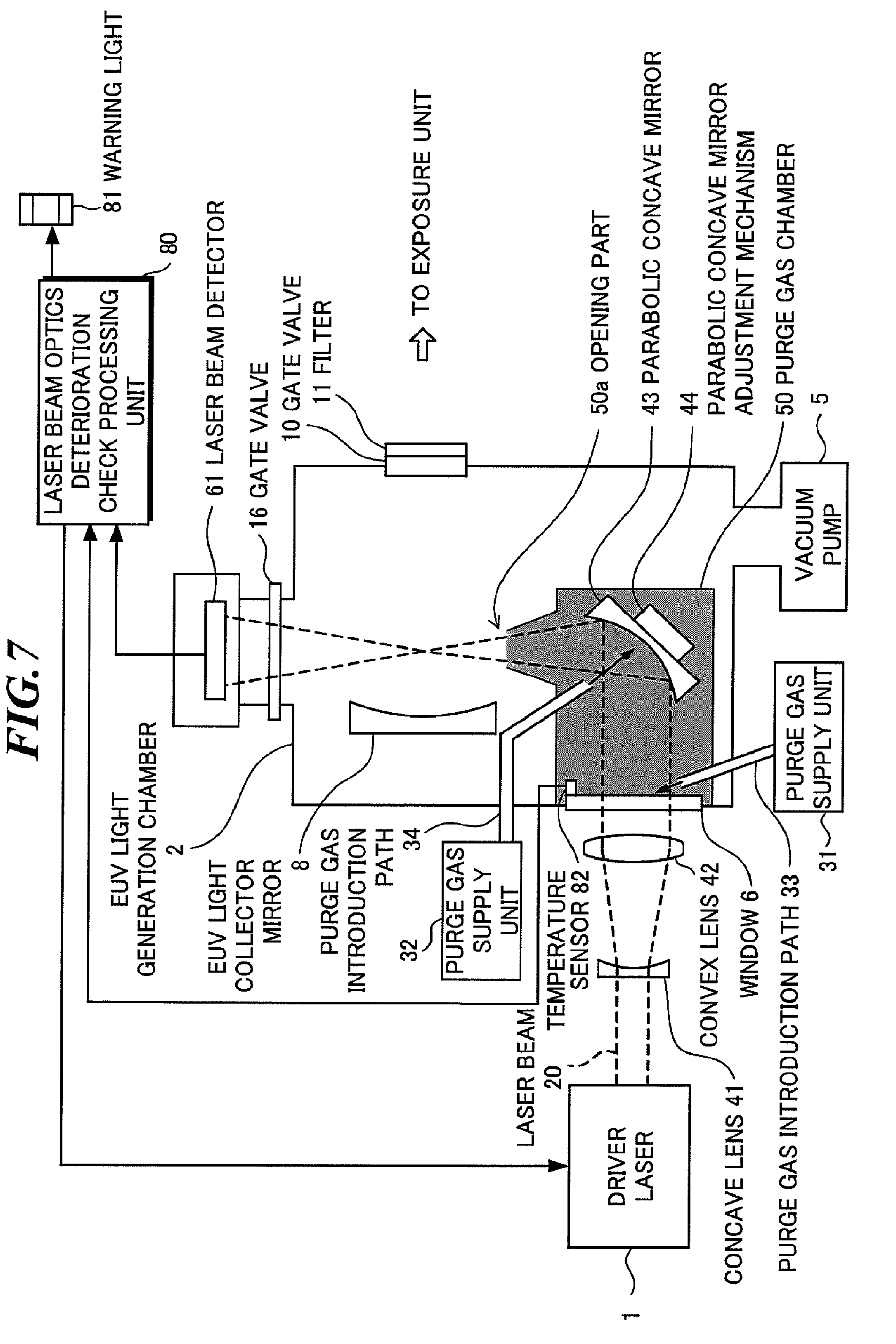
FIG. 7 is a schematic diagram showing a state without EUV light generation in the EUV light source apparatus according to the second embodiment of the present invention.

FIG. 6 and FIG. 7 are schematic diagrams showing the EUV light source apparatus according to the present embodiment. FIG. 6 is a schematic diagram showing a state when the EUV light source apparatus according to the present embodiment generates the EUV light, and FIG. 7 is a schematic diagram showing a state when the EUV light source apparatus according to the present embodiment does not generate the EUV light. Note that FIG. 6 and FIG. 7 omit the target material supply unit 3 and the target material collecting cylinder 7 (refer to FIG. 1) from the drawings, and the target material is assumed to be injected in the direction perpendicular to the page.

As shown in FIG. 6 and FIG. 7, this EUV light source apparatus further includes a temperature sensor 82 which is added to the above described EUV light source apparatus according to the first embodiment (refer to FIG. 2 and FIG. 3) and detects the temperature of the window 6. For the temperature sensor 82, it is possible to use a sheath type thermocouple, for example, in order to maintain a vacuum state and a clean state within the EUV light generation chamber 2. A signal or data representing the temperature of the window 6 detected by the temperature sensor 82 is sent to the laser beam optics deterioration check processing unit 80.

The operation of the EUV light source apparatus according to the present embodiment in the state without EUV light generation (refer to FIG. 7) is the same as the above described operation of the EUV light source apparatus according to the first embodiment in the state without EUV light generation (refer to FIG. 3). In this case, the laser beam optics deterioration check processing unit 80 carries out the above described processing shown in the flowchart of FIG. 5.

Next, the operation of the EUV light source apparatus according to the present embodiment will be described in the case of EUV light generation (refer to FIG. 6).

Figure 8:
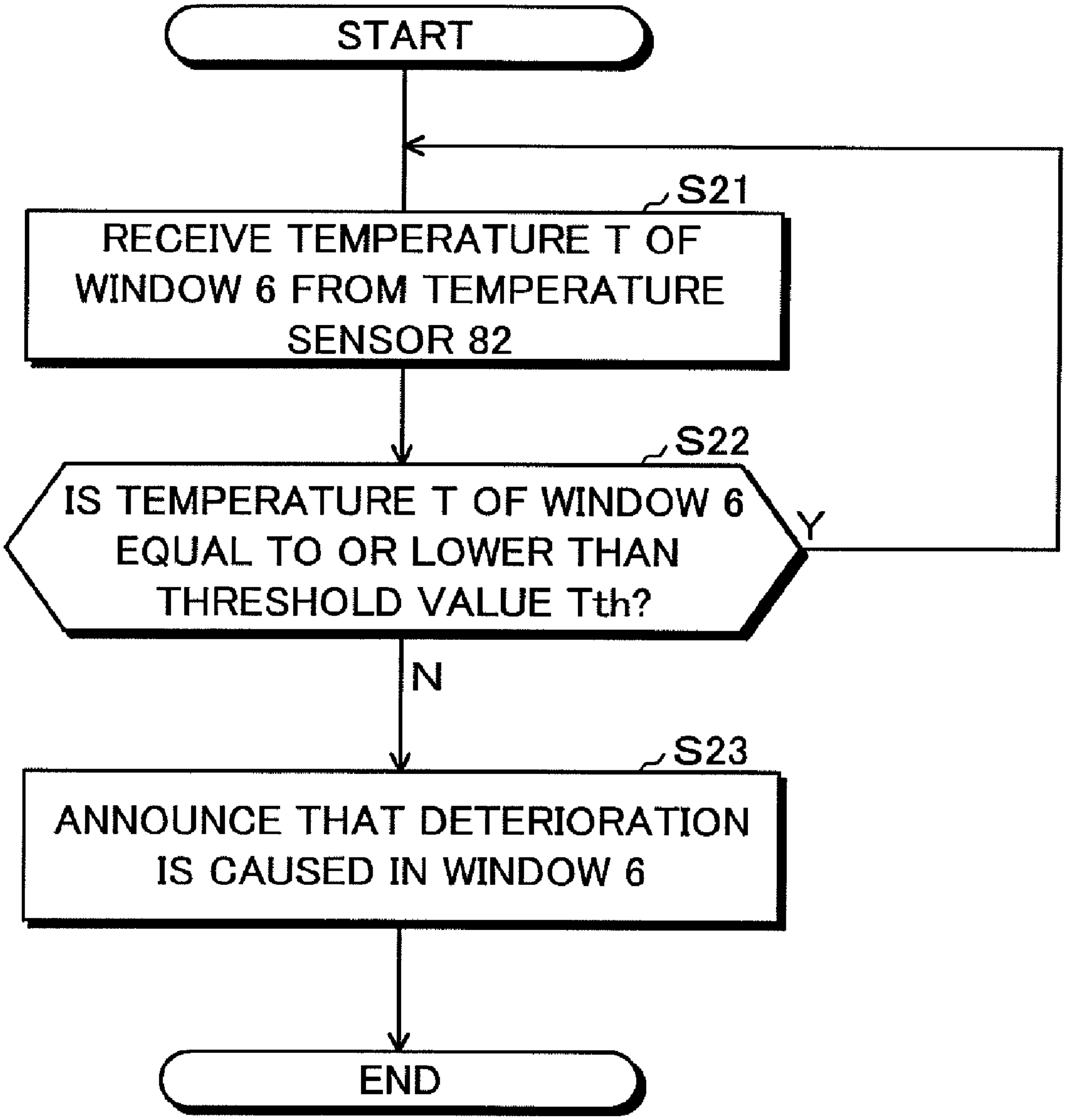
FIG. 8 is a flowchart showing processing carried out by the laser beam optics deterioration check processing unit in FIG. 6 and FIG. 7.

FIG. 8 is a flowchart showing processing carried out by the laser beam optics deterioration check processing unit 80 in the case of EUV light generation in the EUV light source apparatus according to the present embodiment.

First, the laser beam optics deterioration check processing unit 80 receives the signal or data representing the temperature T of the window 6 from the temperature sensor 82 (Step S21).

As described hereinabove, when the window 6 is deteriorated, the window 6 absorbs the laser beam 20 and thereby the temperature of the window 6 increases.

Accordingly, in Step S22, the laser beam optics deterioration check processing unit 80 checks whether or not the temperature T of the window 6 is equal to or less than a predetermined threshold value Tth, and, if the temperature T of the window 6 is equal to or less than the predetermined threshold value Tth, the laser beam optics deterioration check processing unit 80 determines that the window 6 is not deteriorated and returns the process to Step S21. On the other hand, if the temperature T of the window 6 is not equal to nor less than the predetermined threshold value Tth, the laser beam optics deterioration check processing unit 80 determines that the window is deteriorated and moves the process to Step S23.

Then, if the temperature T of the window 6 is not equal to nor less than the predetermined threshold value Tth, that is, when the window 6 is determined to be deteriorated, the laser beam optics deterioration check processing unit 80 notifies the user (operator) of the deterioration (Step S23). Note that the notification about the deterioration caused in the window 6 may be carried out by turning-on, blinking, or change of a blinking pattern of the warning light 81. In addition, the notification may be carried out by sounding of a buzzer or the like, or may be carried out by displaying of characters or an image on a display device such as an LCD. Further, at this time, the laser beam optics deterioration check processing unit 80 may output an operation stop control signal to the driver laser 1 for stopping the operation of the driver laser 1.

In this manner, according to the present embodiment, it is possible to easily detect the deterioration caused in the window 6 and to notify the user (operator), in the state of EUV light generation. Thereby, the judgment whether the window 6 is deteriorated or not can be made more reliable.

(Third Embodiment)

Next, an EUV light source apparatus according to a third embodiment of the present invention will be described.

Figure 9:
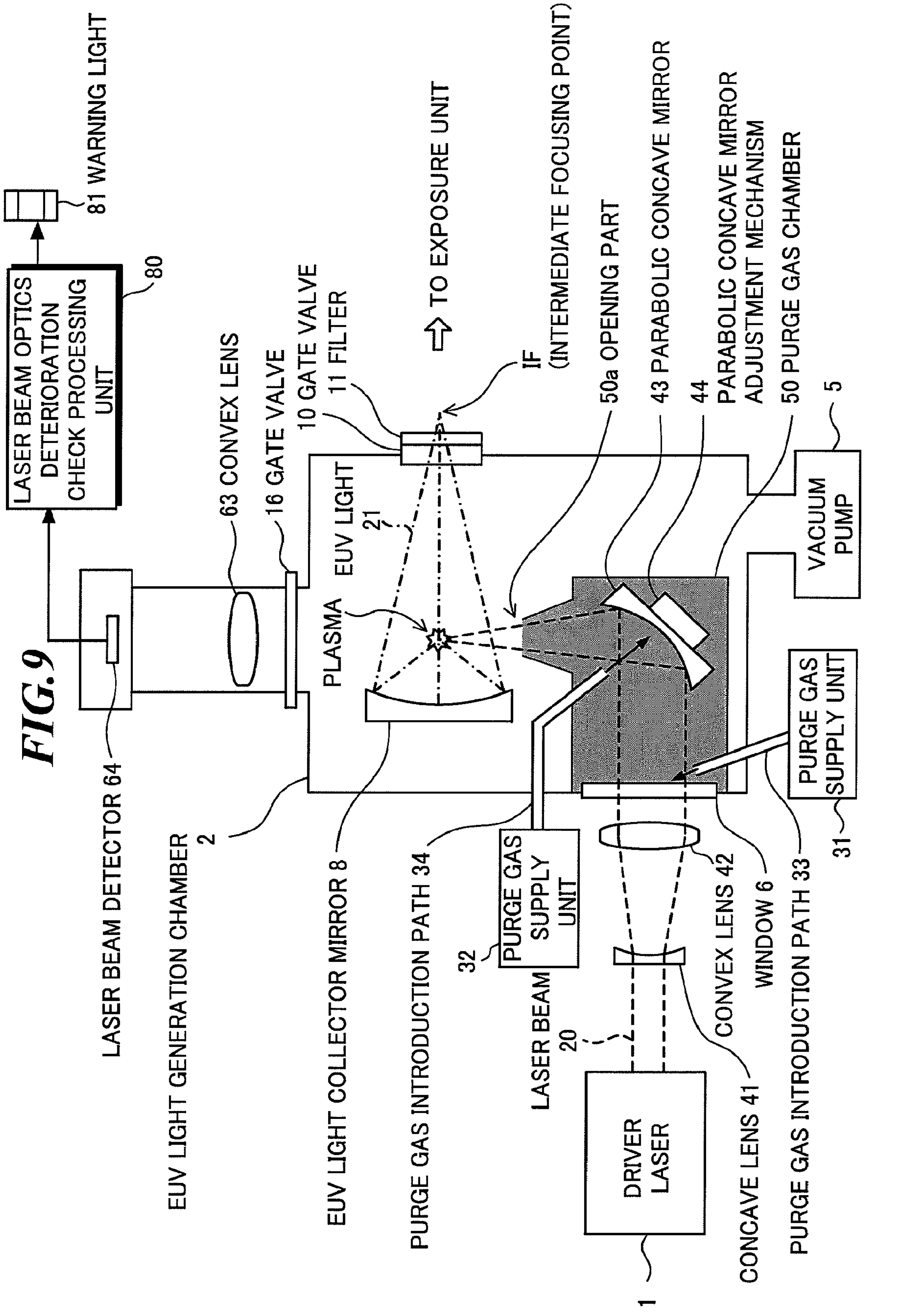
FIG. 9 is a schematic diagram showing a state of EUV light generation in an EUV light source apparatus according to a third embodiment of the present invention.
Figure 10:
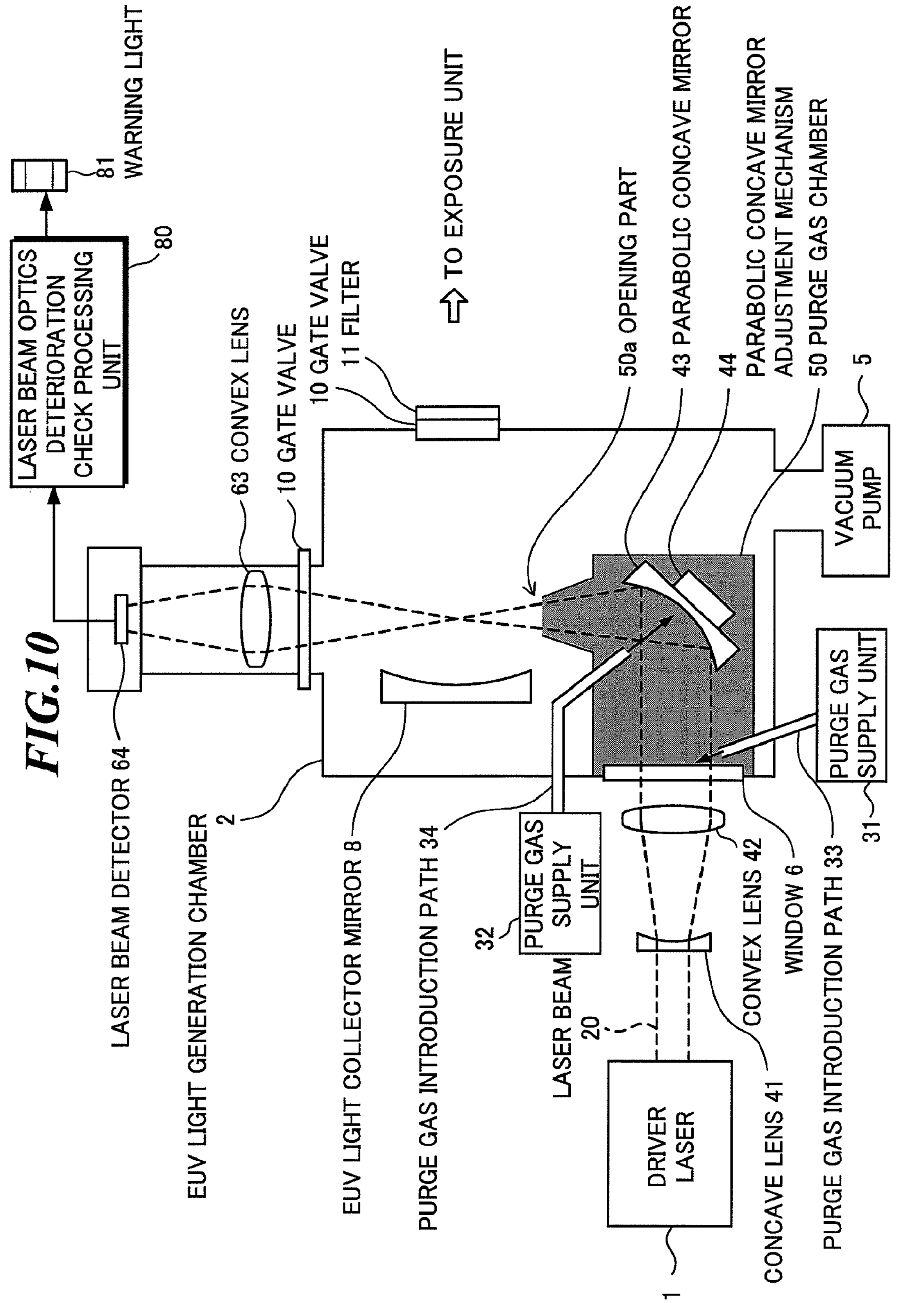
FIG. 10 is a schematic diagram showing a state without EUV light generation in the EUV light source apparatus according to the third embodiment of the present invention.

FIG. 9 and FIG. 10 are schematic diagrams showing the EUV light source apparatus according to the present embodiment. FIG. 9 is a schematic diagram showing a state when the EUV light source apparatus according to the present embodiment generates the EUV light, and FIG. 10 is a schematic diagram showing a state when the EUV light source apparatus according to the present embodiment does not generate the EUV light. Note that FIG. 9 and FIG. 10 omit the target material supply unit 3 and the target material collecting cylinder 7 (refer to FIG. 1) from the drawings, and the target material is assumed to be injected in the direction perpendicular to the page.

As shown in FIG. 9 and FIG. 10, this EUV light source apparatus is further provided with a convex lens 63 focusing the laser beam having passed through the gate valve 16 in addition to the above described EUV light source apparatus according to the first embodiment (refer to FIG. 2 and FIG. 3). Further, the EUV light source apparatus according to the present embodiment is provided with a smaller laser beam detector 64 which replaces the above described laser beam detector 61 in the EUV light source apparatus according to the first and second embodiments.

The operation of the EUV light source apparatus according to the present embodiment in the case of EUV light generation (refer to FIG. 9) is the same as the above described operation of the EUV light source apparatus according to the first embodiment (FIG. 2).

Next, the operation of the EUV light source apparatus according to the present embodiment in the case without EUV light generation (refer to FIG. 10) will be described.

As shown in FIG. 10, in the case without EUV light generation in the EUV light source apparatus according to the present embodiment, the laser beam having passed through the gate valve 16 is focused by the convex lens 63 and input into the laser beam detector 64.

Note that, at this time, the laser beam optics deterioration check processing unit 80 carries out the above described processing shown in the flowchart of FIG. 5.

According to the present embodiment, it is possible to make the size of the laser beam detector 64 smaller than that of the above described laser beam detector 61 in the first embodiment by further providing the convex lens 63 which focuses the laser beam having passed through the gate valve 16.

Note that the EUV light source apparatus according to the present embodiment may be further provided with a temperature sensor 82 (refer to FIG. 6 and FIG. 7) and the laser beam optics deterioration check processing unit 80 may carry out the processing shown in the flowchart of FIG. 8 in the case of EUV generation in the EUV light source apparatus according to the present embodiment.

(Fourth Embodiment)

Next, an EUV light source apparatus according to a fourth embodiment of the present invention will be described.

Figure 11:
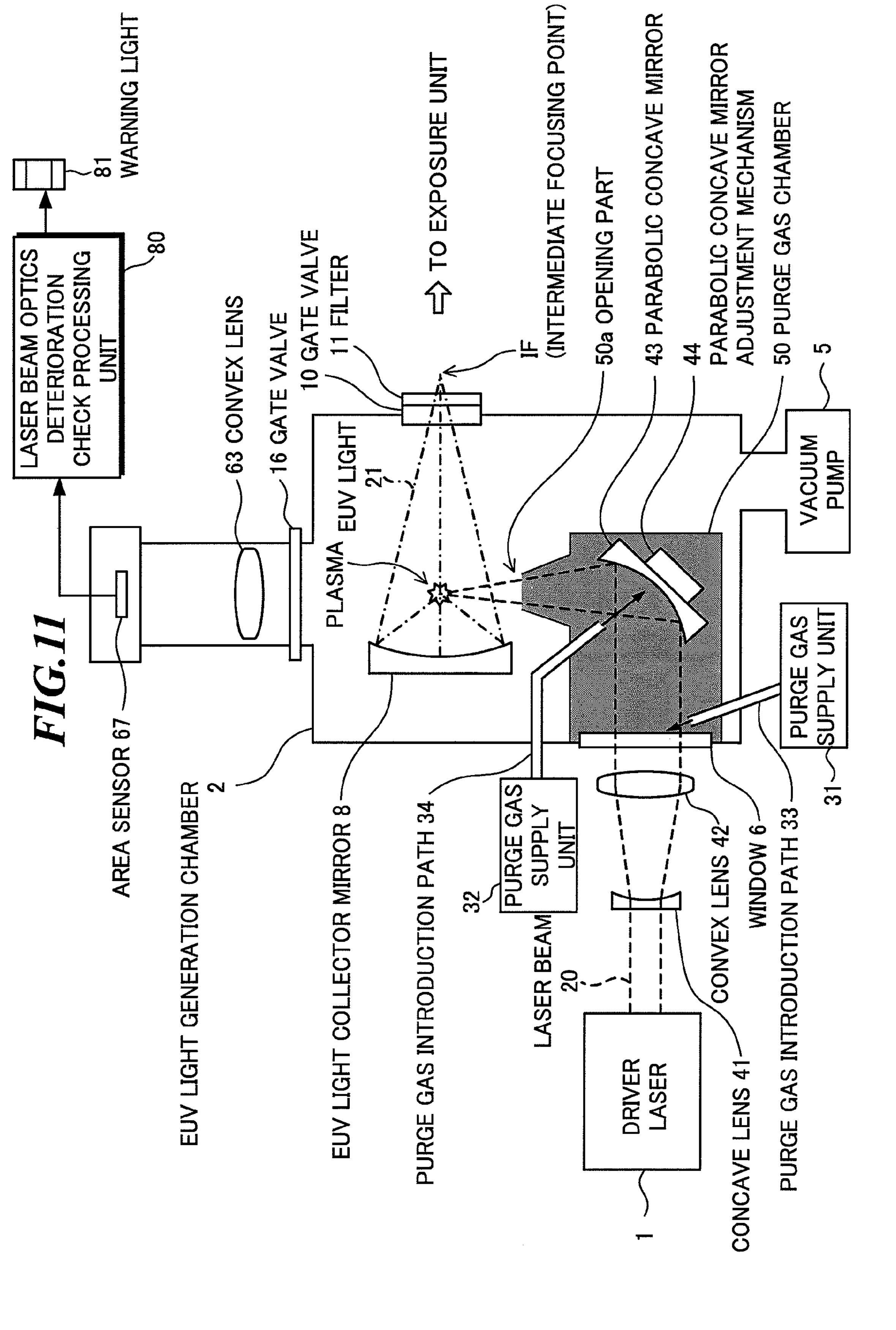
FIG. 11 is a schematic diagram showing a state of EUV light generation in an EUV light source apparatus according to a fourth embodiment of the present invention.
Figure 12:
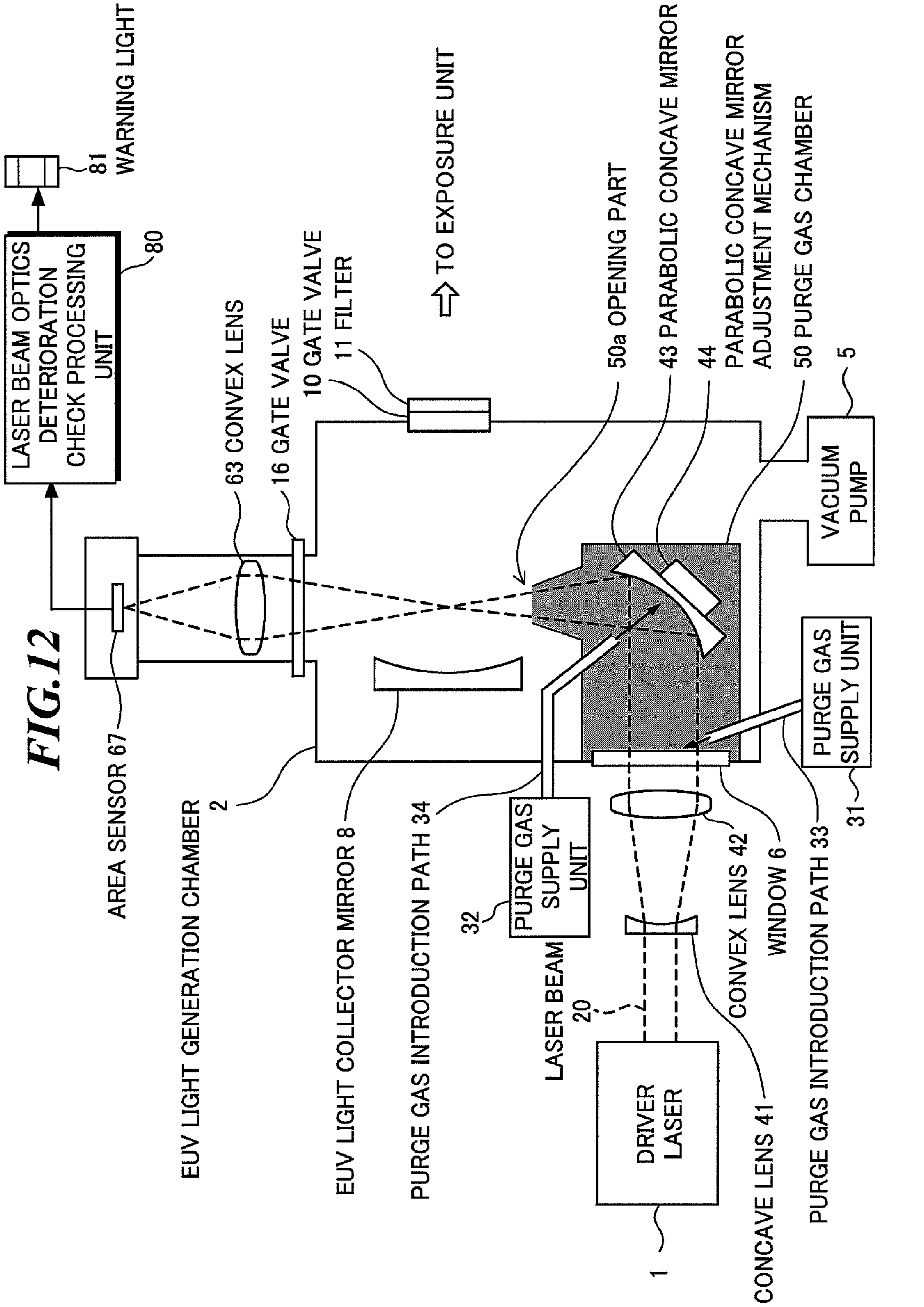
FIG. 12 is a schematic diagram showing a state without EUV light generation in the EUV light source apparatus according to the fourth embodiment of the present invention.

FIG. 11 and FIG. 12 are schematic diagrams showing the EUV light source apparatus according to the present embodiment. FIG. 11 is a schematic diagram showing a state when the EUV light source apparatus according to the present embodiment generates the EUV light, and FIG. 12 is a schematic diagram showing a state when the EUV light source apparatus according to the present embodiment does not generate the EUV light. Note that FIG. 11 and FIG. 12 omit the target material supply unit 3 and the target material collecting cylinder 7 (refer to FIG. 1) from the drawings, and the target material is assumed to be injected in the direction perpendicular to the page.

As shown in FIG. 11 and FIG. 12, this EUV light source apparatus is provided with an area sensor 67, which can shoot a two dimensional image of the laser beam, replacing the above described laser beam detector 64 in the EUV light source apparatus according to the third embodiment (refer to FIG. 9 and FIG. 10). As the area sensor 67, it is possible to use a CCD area sensor, a CMOS area sensor, or the like. The convex lens 63 focuses the laser beam diffused after having been focused by the parabolic concave mirror 43 so as to form a focus on a light receiving surface of the area sensor 67. The area sensor 67 detects the two dimensional image of the incident laser beam and sends an image signal representing the two dimensional image to the laser beam optics deterioration check processing unit 80. In the present embodiment, the area sensor 67 is assumed to send the image signal of (N×M) pixels to the laser beam optics deterioration check processing unit 80 (N and M are integers of two or larger).

The operation of the EUV light source apparatus according to the present embodiment in the case of EUV light generation (refer to FIG. 11) is the same as the above described operation of the EUV light source apparatus according to the first embodiment (FIG. 2).

Next, the operation of the EUV light source apparatus according to the present embodiment in the case without EUV light generation will be described with reference to FIG. 12.

As shown in FIG. 12, the laser beam passed through the gate valve 16 is focused by the convex lens 63 to form an image on the light receiving surface of the area sensor 67, in the case without EUV light generation in the EUV light source apparatus according to the present embodiment.

Figure 13:
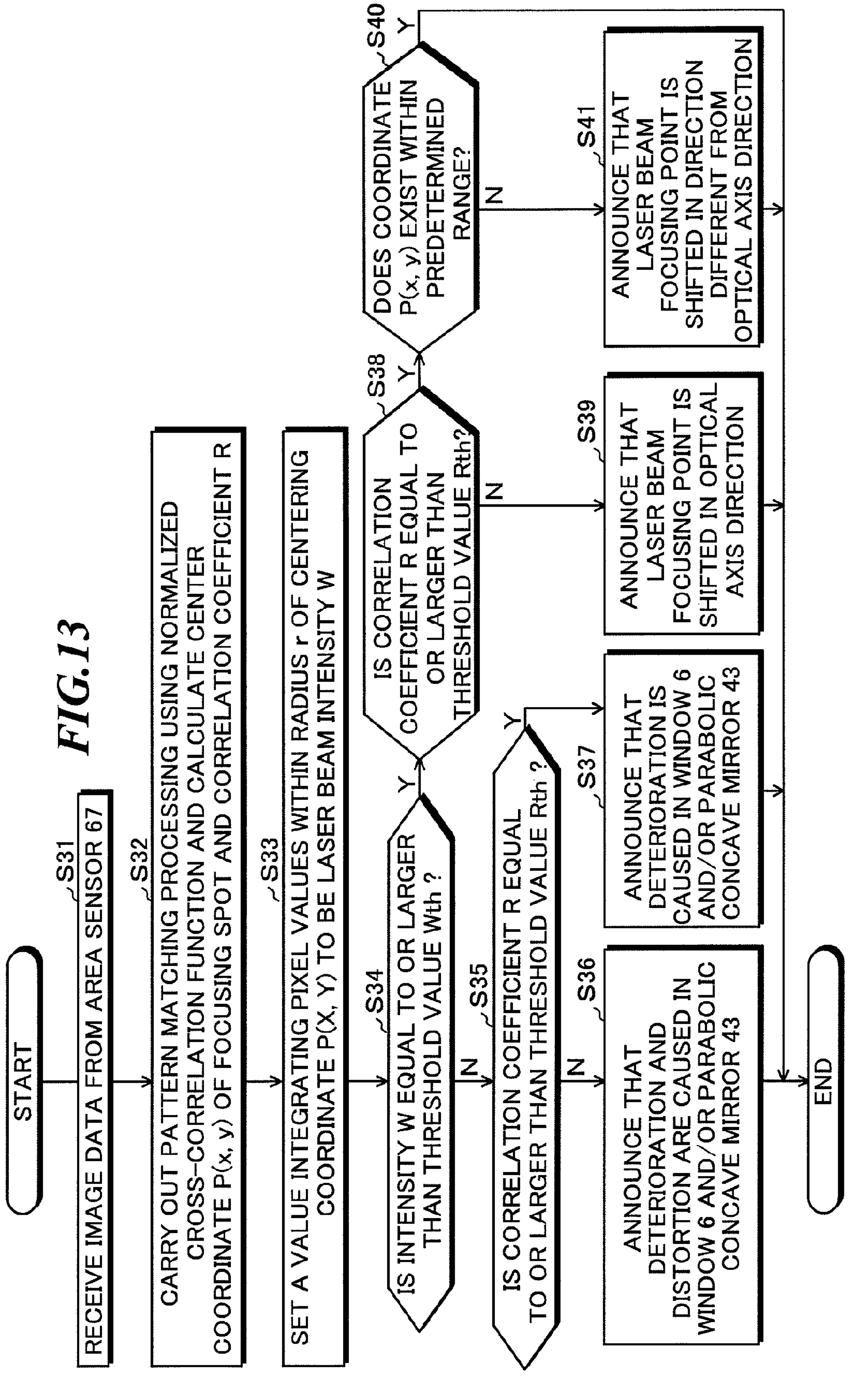
FIG. 13 is a flowchart showing a process carried out by a laser beam optics deterioration check processing unit in FIG. 11 and FIG. 12.

FIG. 13 is a flowchart showing processing carried out by laser beam optics deterioration check processing unit 80 in the case without EUV light generation in the EUV light source apparatus according to the present embodiment (refer to FIG. 12).

Figure 14B:
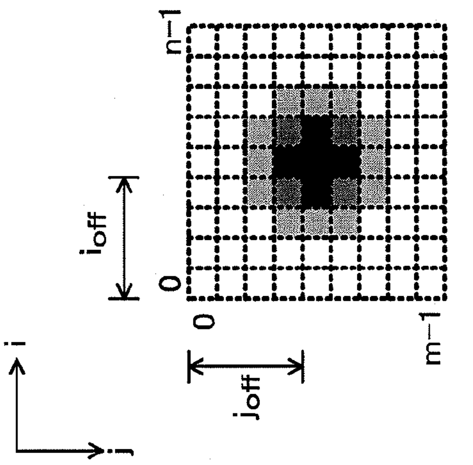
FIGS. 14A and 14B are diagrams showing an example of image data shot by an area sensor shown in FIG. 11 and FIG. 12.
Figure 14A:
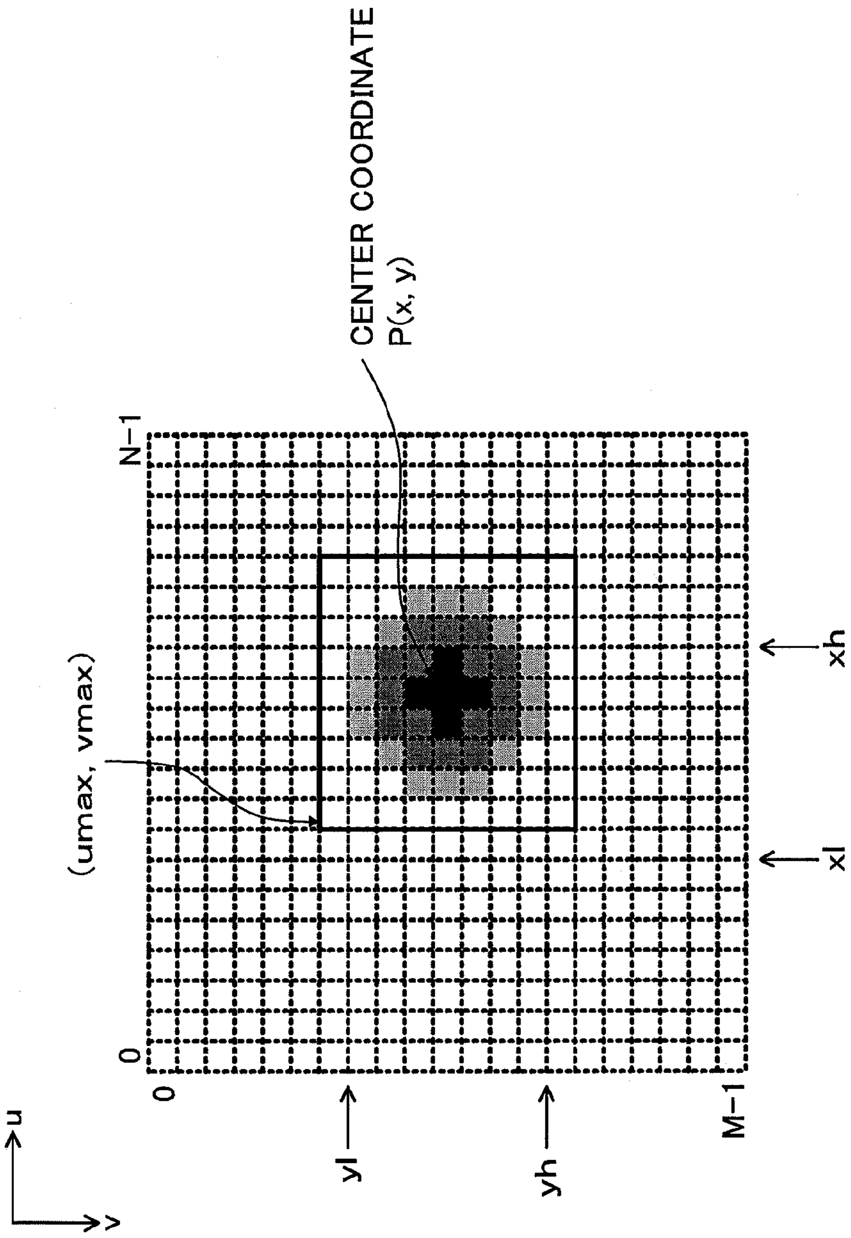

First, the laser beam optics deterioration check processing unit 80 receives the image signal (hereinafter, called "image data" or "imaging data") representing the two dimensional image of the laser beam from the area sensor 67 (Step S31). FIG. 14A is a diagram showing an example of the imaging data which the laser beam optics deterioration check processing unit 80 receives from the area sensor 67.

Then, the laser beam optics deterioration check processing unit 80 carries out pattern matching processing for predetermined template image data and the imaging data using a normalized cross-correlated function, and obtains center coordinate P (x, y) of the focusing spot of the laser beam in the imaging data and also calculates a correlation coefficient R thereof (Step S32). Note that, the present embodiment assumes that the template image data is image data of the laser beam focusing spot at a normal state in which the window 6 or the parabolic concave mirror 43 does not have deterioration nor an alignment shift, and the template image data is assumed to have (n×m) pixels (n<N, m<M). FIG. 14B is a diagram showing an example of the template image. In the template image data shown in FIG. 14B, an offset in the i-axis direction between the coordinate (0, 0) and the center coordinate of the focusing spot is denoted by $i_{off}$ and an offset in the j-axis direction between the two coordinates is denoted by $j_{off}$.

Next, the pattern matching processing using the normalized cross-correlation function will be described.

The pattern matching processing using the normalized cross-correlation function is processing as follows. That is, when each pixel value composing the template image data is denoted by T(i, j) (where, 0≦i≦n−1, 0≦j≦m−1) and each pixel value composing the imaging data is denoted by F(u, v) (where, 0≦u≦N−1, 0≦v≦M−1), the normalized cross-correlation function NR(u, v) for each set of the coordinates (u, v) of the imaging data is calculated from the following formula (1) for the purpose of searching for a maximum value of the normalized cross-correlation function NR(u, v), and thereby searching for an area where the imaging data has the highest correlation with the template image data (in an area of (n×m) pixels in the present embodiment).

$$NR(u,v)=\frac{\sum_{i=0}^{n-1}\sum_{j=0}^{m-1}(F(i+u,j+v)-\overline{F}(u,v))(T(i,j)-\overline{T})}{\sqrt{\sum_{i=0}^{n-1}\sum_{j=0}^{m-1}(F(i+u,j+v)-\overline{F}(u,v))^2}\sqrt{\sum_{i=0}^{n-1}\sum_{j=0}^{m-1}(T(i,j)-\overline{T})^2}} \quad (1)$$

where $$\overline{F}(u,v)=\frac{\sum_{i=0}^{n-1}\sum_{j=0}^{m-1}F(i+u,j+v)}{n\cdot m} \quad (2)$$

and $$\overline{T}=\frac{\sum_{i=0}^{n-1}\sum_{j=0}^{m-1}T(i,j)}{n\cdot m} \quad (3)$$

The u-axis component umax of the imaging data coordinate (umax, vmax) maximizing the above formula (1) is added with the above described offset $i_{off}$ and denoted by x, and the v-axis component of vmax is added with the above described offset $j_{off}$ and denoted by y. Then, the coordinate (x, y) are presumed as the center coordinate P (x, y) of the focusing spot. And NR (umax, Vmax) is presumed as a correlation function R.

That is, $$x=u\max+I_{off} \quad (4)$$

$$y=v\max+J_{off} \quad (5)$$

$$R=NR(u\max, v\max) \quad (6)$$

With another reference to FIG. 13, the laser beam optics deterioration check processing unit 80 integrates the pixel values of pixels located within a circle having a predetermined radius r centering the center coordinates P (x, y) of the focusing spot and presumes the integrated value as an intensity W of the laser beam (Step S33).

Next, in Step S34, the laser beam optics deterioration check processing unit 80 checks whether or not the laser beam intensity W is equal to or larger than a predetermined threshold value Wth. If the laser beam intensity W is not equal to nor larger than the threshold value Wth, it is determined that the window 6 and/or the parabolic concave mirror 43 is deteriorated, and the process goes to Step S35, and if the laser beam intensity W is equal to or larger than the threshold value Wth, it is determined that the window 6 or the parabolic concave mirror 43 is not deteriorated and the process goes to Step S38.

In Step 35, the laser beam optics deterioration check processing unit 80 further checks whether or not the correlation coefficient R is equal to or larger than a predetermined threshold value Rth. If the correlation coefficient R is not equal to nor larger than the threshold value Rth, it is determined that the distribution of the focusing spots is abnormal and the window 6 and/or the parabolic concave mirror 43 is distorted, and the process goes to Step S36, and, if the correlation coefficient R is equal to or larger than the threshold value Rth, it is determined that the distribution of the focusing spots is normal and the window 6 and the parabolic concave mirror 43 is not distorted, and the process goes to Step S37.

If the laser beam intensity W is not equal to nor larger than the predetermined threshold value Wth and also the correlation coefficient R is not equal to nor larger than the predetermined threshold value Rth, the laser beam optics deterioration check processing unit 80 determines that the window 6 and/or the parabolic concave mirror 43 is deteriorated and also the window 6 and/or the parabolic concave mirror 43 is distorted, and notifies the user (operator) of the determination (Step S36). In this case, the user (operator) may generate the EUV light normally by change of the window 6 and/or the parabolic concave mirror 43. Note that the notification may be carried out by turning-on, blinking, or change of a blinking pattern of the warning light 81 about the deterioration and the distortion caused in the window 6 and/or the parabolic concave mirror 43. In addition, the notification may be carried out by sounding of a buzzer or the like, or may be carried out by displaying of characters or an image on a display device such as an LCD.

On the other hand, if the laser beam intensity W is not equal to nor larger than the predetermined threshold value Wth but the correlation coefficient R is equal to or larger than the predetermined threshold value Rth, the laser beam optics deterioration check processing unit 80 determines that the window 6 and/or the parabolic concave mirror 43 is deteriorated and notifies the user (operator) of the determination (Step S37). Also in this case, the user (operator) may generate the EUV light normally by change of the window 6 and/or the parabolic concave mirror 43.

In Step S38, even if the laser beam intensity W is equal to or larger than the predetermined threshold value Wth, the laser beam optics deterioration check processing unit 80 checks whether or not the correlation coefficient R is equal to or larger than the predetermined threshold value Rth. If the correlation coefficient R is not equal to nor larger than the predetermined threshold value Rth, it is determined that focusing of the laser beam is shifted in the optical axis direction (z-axis direction in FIGS. 4A and 4B) of the laser beam, and the process goes to Step S39, and, if the correlation coefficient R is equal to or larger than the predetermined threshold value Rth, it is determined that the focusing of the laser beam is not shifted in the optical axis direction of the laser beam and the process goes to Step S40.

If the laser beam intensity W is equal to or larger than the predetermined threshold value Wth but the correlation coefficient R is not equal to nor larger than the predetermined threshold value Rth, the laser beam optics deterioration check processing unit 80 determines that the laser beam focusing is shifted in the optical axis direction (z-axis direction in FIGS. 4A and 4B) of the laser beam, and notifies the user (operator) of the determination (Step S39). In this case, the user (operator) may operate the parabolic concave mirror adjustment mechanism 44 to move the parabolic concave mirror 43 in the z-axis direction in FIGS. 4A and 4B so as to generate the desired EUV light.

On the other hand, if the laser beam intensity W is equal to or larger than the predetermined threshold value Wth and also the correlation coefficient R is equal to or larger than the predetermined threshold value Rth, the laser beam optics deterioration check processing unit 80 further checks whether or not the coordinate P(x, y) of the center of the focusing spot exists within a predetermined range (Step S40). Whether or not the coordinate P(x, y) of the center of the focusing spot exists within the predetermined range can be checked by examinations whether x exists between predetermined threshold values x1 and xh (refer to FIG. 14A), that is, whether x1<x<xh is true, and whether y exists between predetermined threshold values y1 and yh (refer to FIG. 14A), that is, whether y1<y<yh is true.

In Step S40, if the coordinate P(x, y) of the center of the focusing spot exists within the predetermined range, the laser beam optics deterioration check processing unit 80 determines that the window 6 and/or the parabolic concave mirror 43 does not have deterioration, distortion or alignment shift, and terminates the processing. If the coordinate P(x, y) of the center of the focusing spot does not exist within the predetermined range, the laser beam optics deterioration check processing unit 80 determines that the focusing of the laser beam is shifted in a direction different from the optical axis of the laser beam and the x and y alignment shifts are caused in the parabolic concave mirror 43, and advances the process to Step S41. The case that the x and y alignment shifts are caused in the parabolic concave mirror 43 corresponds to the case that the parabolic concave mirror 43 is shifted in the x-axis direction and the y-axis direction in FIGS. 4A and 4B or the case that the tilt angle of the parabolic concave mirror 43 is shifted in the θx-direction and/or θy-direction in FIGS. 4A and 4B. Note that, when the window 6 or the parabolic concave mirror 43 does not have any abnormality, the process may be returned to Step S31 to repeatedly carry out the check of the laser beam intensity.

In Step 41, the laser beam optics deterioration check processing unit 80 notifies the user (operator) of that the x and y alignment shift is caused in the parabolic concave mirror 43. In this case, the user (operator) can generate the desired EUV light by moving the parabolic concave mirror 43 in the x-axis direction and/or the y-axis direction in FIGS. 4A and 4B or by adjusting the tilt angle of the parabolic concave mirror 43, in the operation of the parabolic concave mirror adjustment mechanism 44.

In this manner, according to the present embodiment, since it can be easily detected in the case without EUV light generation that the window 6 and/or the parabolic concave mirror 43 has deterioration and/or distortion, and/or that the laser beam focusing is shifted and the user (operator) can be notified about those conditions, the user (operator) can appropriately grasp whether or not to replace the window 6 and/or the parabolic concave mirror 43, and/or whether to carry out the alignment adjustment. Accordingly, it becomes possible to generate the EUV light stably.

Figure 15:
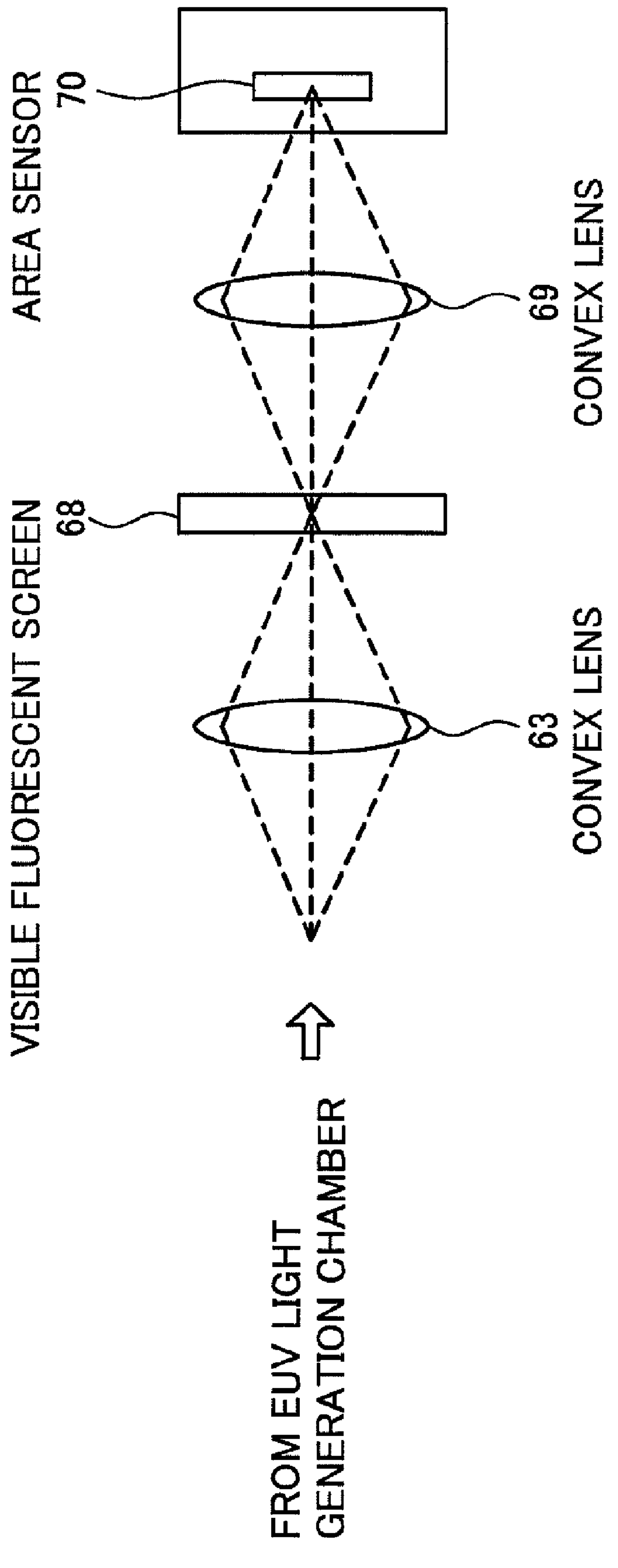
FIG. 15 is a schematic diagram showing an example using another area sensor instead of the area sensor shown in FIG. 11 and FIG. 12.

Note that, while the laser beam focused by the convex lens 63 is input directly into the area sensor 67 in the present embodiment, as shown in FIG. 15, the laser beam focused by the convex lens 63 may be input into a visible fluorescent screen 68 to be converted into visible light, and the visible light may be focused by a convex lens 69 to be input into a usual area sensor 70 which has sensitivity in the visible light region. Thereby, it becomes possible to use the inexpensive area sensor 70 which has sensitivity in the visible light region, instead of the expensive area sensor 67 which has sensitivity in the laser light region. Further, even when the EUV light source apparatus according to the present embodiment is used for a long period and the visible fluorescent screen 68 is deteriorated, it becomes possible to suppress the deterioration of the area sensor 70. In this case, only the visible fluorescent screen 68, which is less expensive than the area sensor 70, may be replaced, and the area sensor 70 needs not to be replaced.

In addition, the EUV light source apparatus according to the present embodiment may be further provided with a temperature sensor 82 (refer to FIG. 6 and FIG. 7), and the laser beam optics deterioration check processing unit 80 may carry out the processing shown in the flowchart of FIG. 8 in the case of EUV light generation in the EUV light source apparatus according to the present embodiment.

(Fifth Embodiment)

Next, an EUV light source apparatus according to a fifth embodiment of the present invention will be described.

Figure 16:
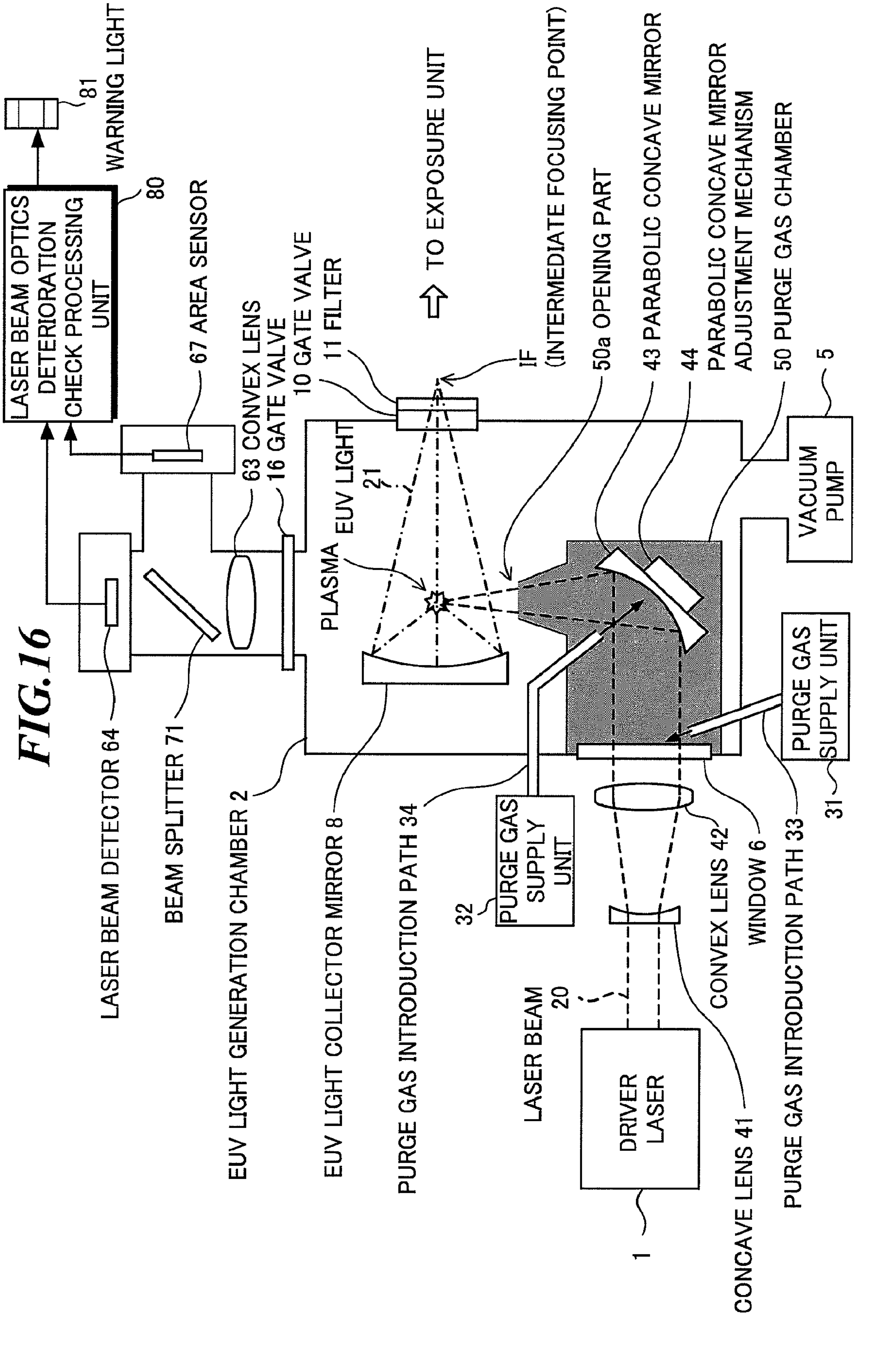
FIG. 16 is a schematic diagram showing a state of EUV light generation in an EUV light source apparatus according to a fifth embodiment of the present invention.
Figure 17:
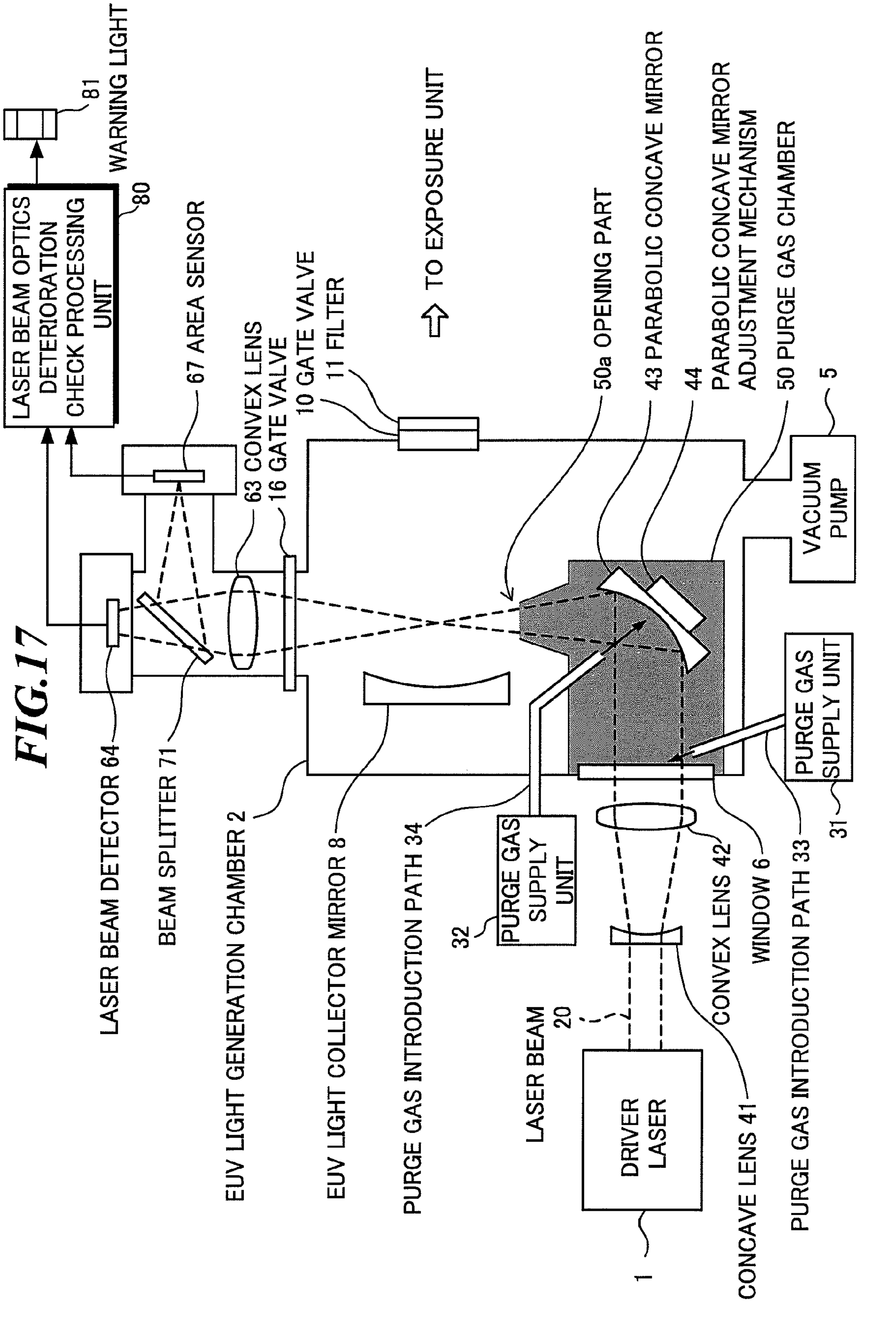
FIG. 17 is a schematic diagram showing a state without EUV light generation in the EUV light source apparatus according to the fifth embodiment of the present invention.

FIG. 16 and FIG. 17 are schematic diagrams showing the EUV light source apparatus according to the present embodiment. FIG. 16 is a schematic diagram showing a state of EUV light generation in the EUV light source apparatus according to the present embodiment, and FIG. 17 is a schematic diagram showing a state without EUV light generation in the EUV light source apparatus according to the present embodiment. Note that, FIG. 16 and FIG. 17 omit the target material supply unit 3 and the target material collecting cylinder 7 (refer to FIG. 1) from the drawings and the target material is assumed to be injected in the direction perpendicular to the page.

As shown in FIG. 16 and FIG. 17, this EUV light source apparatus is further provided with a beam splitter 71 dividing the laser beam focused by the convex lens 63 and the above described area sensor 67 in the EUV light source apparatus according to the fourth embodiment (refer to FIG. 11 and FIG. 12) in addition to the above described EUV light source apparatus according to the third embodiment (refer to FIG. 9 and FIG. 10).

The operation of the EUV light source apparatus according to the present embodiment in the case of EUV light generation (refer to FIG. 16) is the same as the above described operation of the EUV light source apparatus according to the first embodiment (FIG. 2).

Next, the operation of the EUV light source apparatus according to the present embodiment in the case without EUV light generation will be described with reference to FIG. 17.

In the case without EUV light generation in the EUV light source apparatus according to the present embodiment, the laser beam having passed through the gate valve 16 is focused by the convex lens 63 and divided by the beam splitter 71 in a first direction (an upward direction in the drawing) and a second direction (a rightward direction in the drawing) The laser beam transmitted through the beam splitter 71 in the first direction is input into the laser beam detector 64, and the laser beam transmitted through the beam splitter 71 in the second direction is input into the area sensor 67.

In the case without EUV light generation in the EUV light source apparatus according to the present embodiment, the laser beam optics deterioration check processing unit 80 carries out the processing shown in the flowchart of FIG. 5 using the signal or data from the laser beam detector 64 and also carries out the processing shown in the flowchart of FIG. 13 using the image data from the area sensor 67.

In this manner, according to the present embodiment, it is possible to detect the intensity of the laser beam by the laser beam detector 64 and to detect the center coordinate or the like of the laser beam by the area sensor 67, at the same time. Thereby, the judgment can be made more reliable whether or not the window 6 and/or the parabolic concave mirror 43 has deterioration or the like.

Note that the EUV light source apparatus according to the present embodiment may be further provided with a temperature sensor 82 (refer to FIG. 6 and FIG. 7), and the laser beam optics deterioration check processing unit 80 may carry out the processing shown in the flowchart of FIG. 8 in the case of EUV light generation in the EUV light source apparatus according to the present embodiment.

(Sixth Embodiment)

Next, an EUV light source apparatus according to a sixth embodiment of the present invention will be described.

Figure 18:
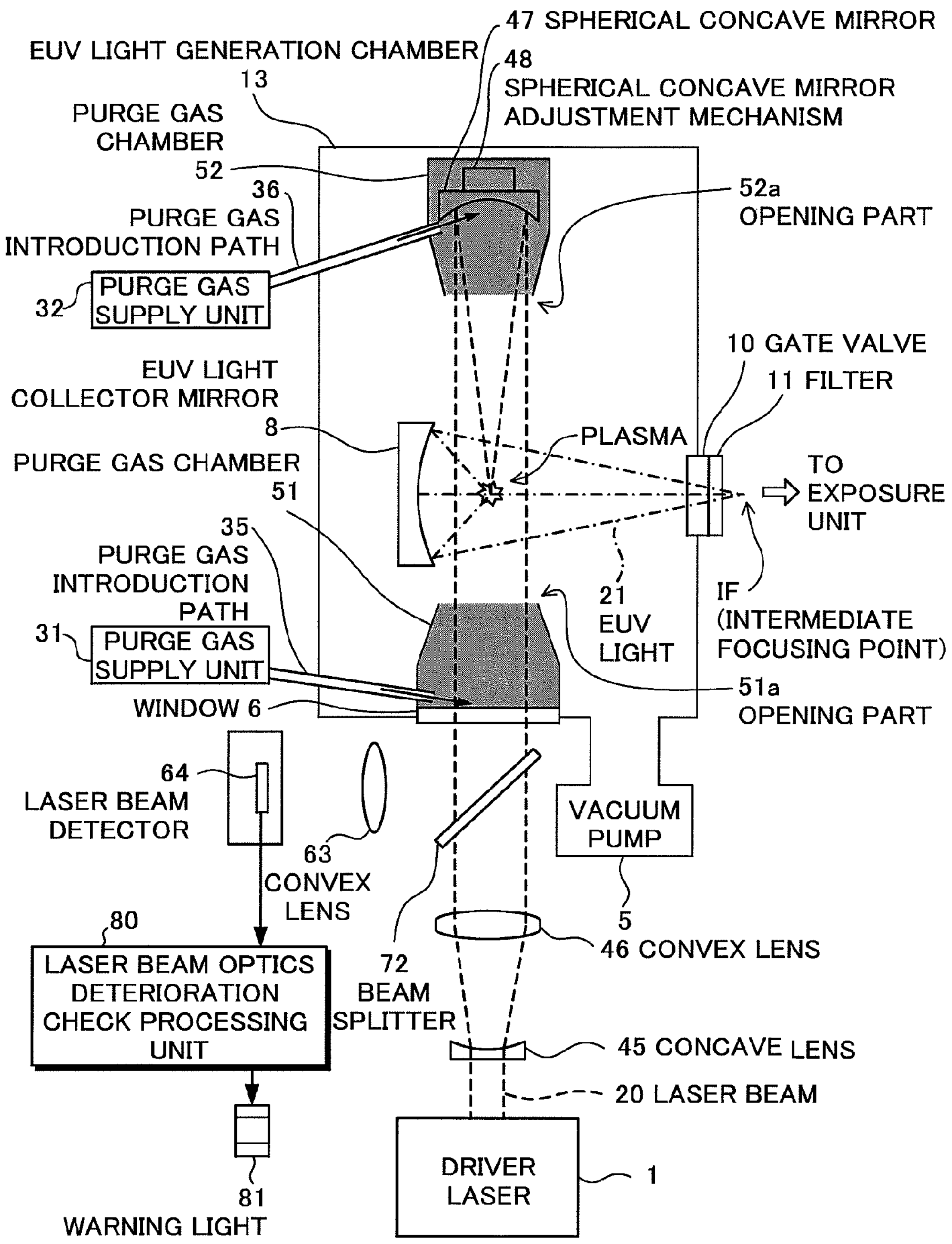
FIG. 18 is a schematic diagram showing a state of EUV light generation in an EUV light source apparatus according to a sixth embodiment of the present invention.
Figure 19:
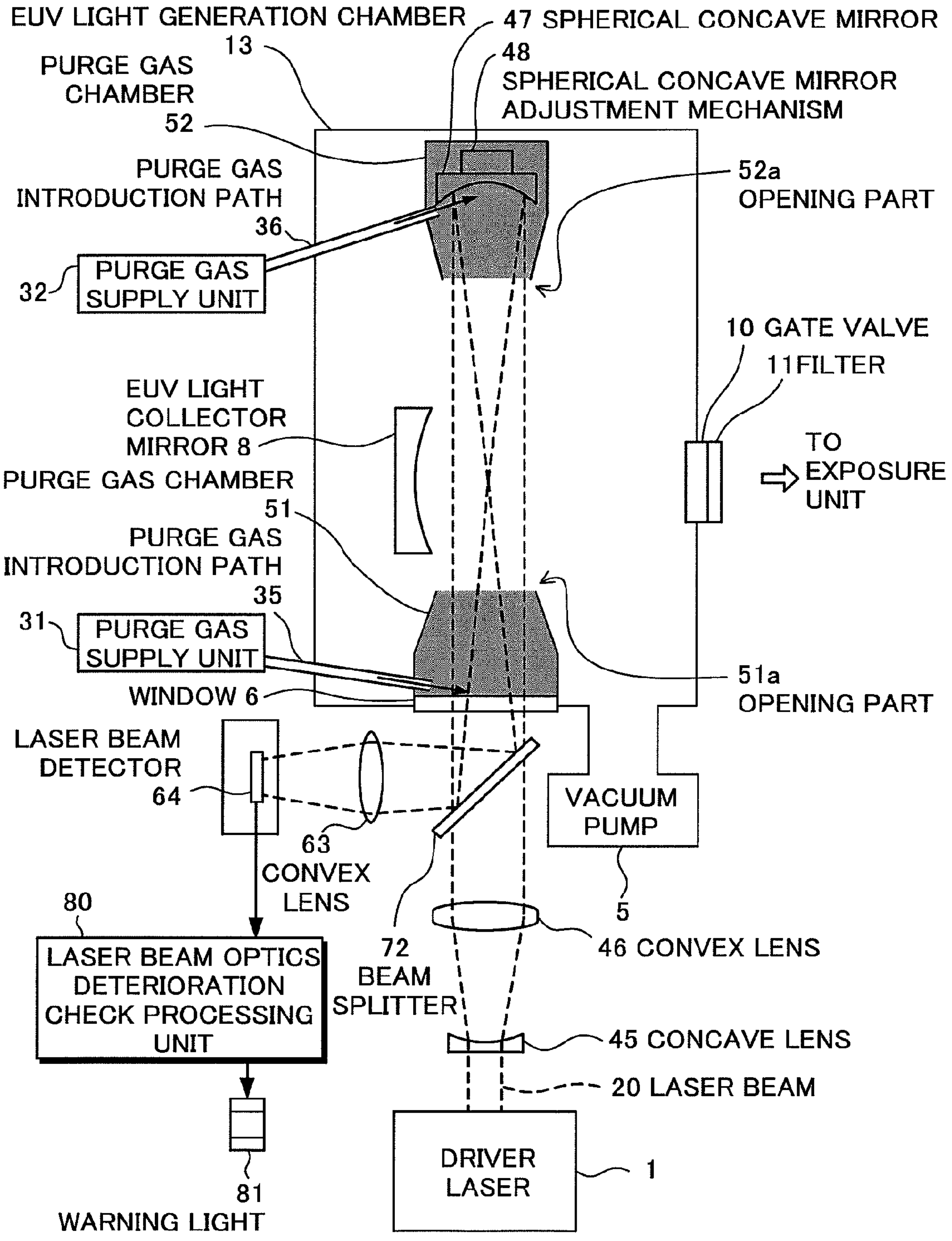
FIG. 19 is a schematic diagram showing a state without EUV light generation in the EUV light source apparatus according to the sixth embodiment of the present invention.

FIG. 18 and FIG. 19 are schematic diagrams showing the EUV light source apparatus according to the present embodiment. FIG. 18 is a schematic diagram showing a state of EUV light generation in the EUV light source apparatus according to the present embodiment, and FIG. 19 is a schematic diagram showing a state without EUV light generation in the EUV light source apparatus according to the present embodiment. Note that, FIG. 18 and FIG. 19 omit the target material supply unit 3 and the target material collecting cylinder 7 (refer to FIG. 1) from the drawings and the target material is assumed to be injected in the direction perpendicular to the page.

First, mainly with reference to FIG. 18, the operation in the case of EUV light generation in the EUV light source apparatus according to the present embodiment will be described, and then, mainly with reference to FIG. 19, the operation in the case without EUV light generation in the EUV light source apparatus according to the present embodiment will be described.

As shown in FIG. 18, the laser beam 20 emitted from the driver laser 1 in the upward direction of the drawing is diffused by a concave lens 45, collimated by a convex lens 46, and transmitted through a beam splitter 72 and the window 6 to be input into an EUV light generation chamber 13.

A spherical concave mirror 47 and a spherical concave mirror adjustment mechanism 48 adjusting the position and the angle (tilt angle) of the spherical concave mirror 47 are disposed within the EUV light generation chamber 13.

The laser beam 20, which has been transmitted through the window 6 and input into the EUV light generation chamber 13, is reflected by the spherical concave mirror 47 in the downward direction of the drawing and focused onto the path of the target material. Thereby, the target material is excited into plasma and the EUV light 21 is generated.

The EUV light collector mirror 8 reflects the generated EUV light 21 in the rightward direction of the drawing to focus the EUV light onto the IF (intermediate focusing point). The EUV light 21 reflected by the EUV light collector mirror 8 is transmitted through the gate valve 10 and the filter 11 provided to the EUV light generation chamber 13. The EUV light 21 focused onto the IF (intermediate focusing point) is guided to the exposure unit or the like via the transmission optics thereafter.

This EUV light source apparatus further includes the purge gas supply units 31 and 32, a purge gas introduction path 35 for introducing the purge gas injected from the purge gas supply unit 31 to the surface of the window 6 on the inner side of the EUV light generation chamber 13, and a purge gas introduction path 36 for introducing the purge gas injected from the purge gas supply unit 32 to the reflection surface of the spherical concave mirror 47.

Further, a purge gas chamber 51 surrounding the window 6, and a purge gas chamber 52 surrounding the spherical concave mirror 47 and the spherical concave mirror adjustment mechanism 48 are disposed within the EUV light generation chamber 13. The purge gas chamber 51 has a tapered cylindrical shape at the upper part thereof in the drawing, and is provided with an opening part 51*a* at the top thereof (upper part in the drawing) for transmitting the laser beam 20 having been transmitted through the window 6. Further, the purge gas chamber 52 has a tapered cylindrical shape at the lower part thereof and is provided with an opening part 52*a* at the bottom thereof (lower part in the drawing) for transmitting the laser beam 20 having been transmitted through the window 6 and the laser beam 20 reflected by the spherical concave mirror 47.

Next, with reference to FIG. 19, the operation in the case without EUV light generation in the EUV light source apparatus according to the present embodiment will be described.

In the case without EUV light generation in the EUV light source apparatus, the target material supply unit 3 does not supply the target material into the EUV light generation chamber 13 as described hereinabove. Thereby, the laser beam focused by the spherical concave mirror 47 is not applied to the target material and is transmitted through the window 6, while being diffused, to be emitted from the EUV light generation chamber 13 in the downward direction of the drawing.

The laser beam, which is emitted from the EUV light generation chamber 13 in the downward direction of the drawing, is reflected by the beam splitter 72 to the leftward direction of the drawing and focused by the convex lens 63 to be input into the laser beam detector 64. Note that the laser beam optics deterioration check processing unit 80 carries out the foregoing processing shown in the flowchart of FIG. 5 in the case without EUV light generation in the EUV light source apparatus according to the present embodiment.

According to the present embodiment, since the spherical concave mirror 47 has a function to correct the chromatic aberration of the concave lens 45 or the convex lens 46, it is possible to focus the laser beam 20 more efficiently than in the case of using a parabolic concave mirror. Thereby, the EUV light can be generated more efficiently.

Note that the EUV light source apparatus according to the present embodiment may be further provided with a temperature sensor 82 (refer to FIG. 6 and FIG. 7) and the laser beam optics deterioration check processing unit 80 may carry out the processing shown in the flowchart of FIG. 8 in the case of EUV light generation in the EUV light source apparatus according to the present embodiment.

Further, the EUV light source apparatus according to the present embodiment may be provided with an area sensor 67 instead of or in addition to the laser beam detector 64. In this case, the laser beam optics deterioration check processing unit 80 may carry out the processing shown in the flowchart of FIG. 13 in the case without EUV light generation in the EUV light source apparatus according to the present embodiment.

(Seventh Embodiment)

Next, an EUV light source apparatus according to a seventh embodiment of the present invention will be described.

Figure 20:
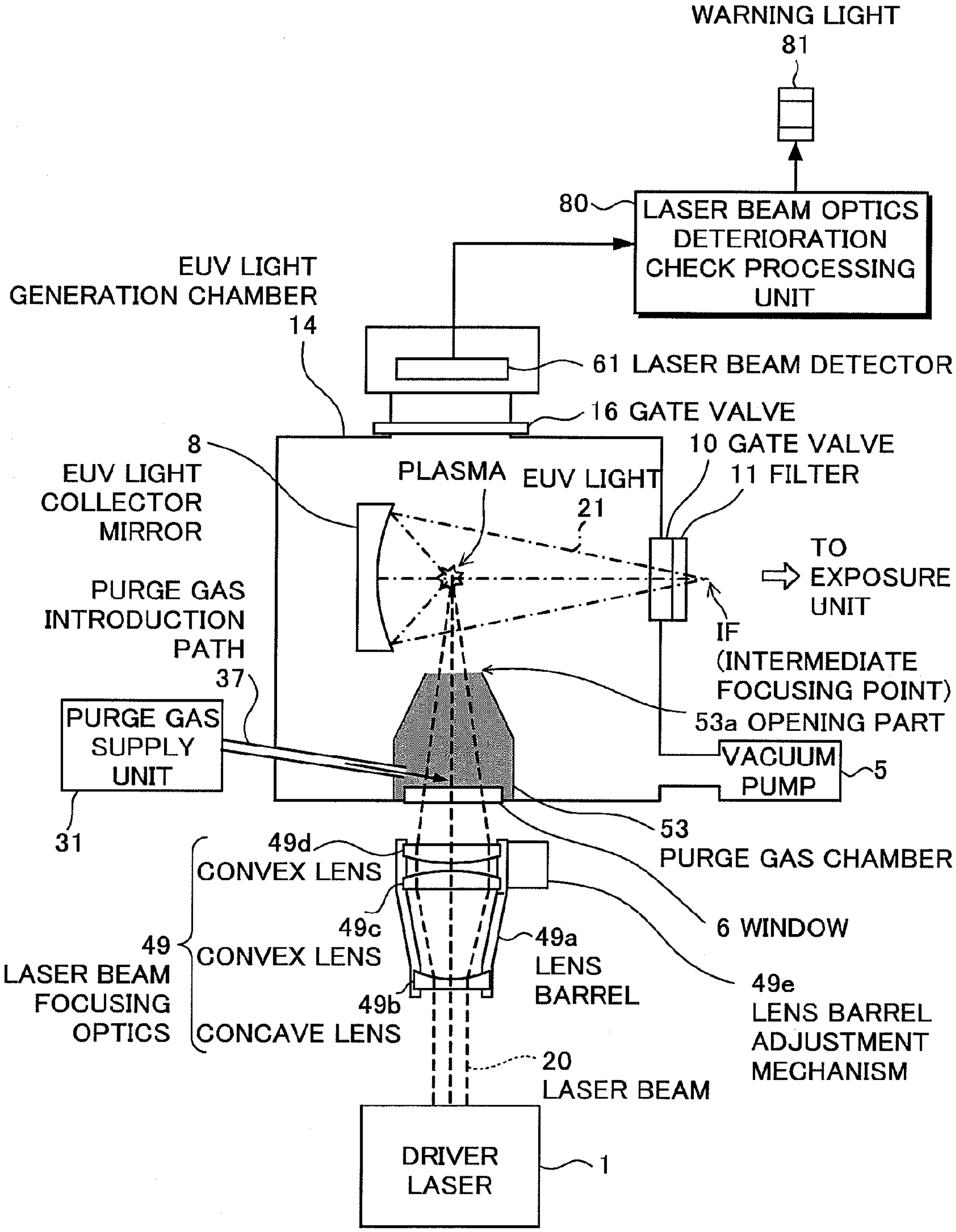
FIG. 20 is a schematic diagram showing a state of EUV light generation in an EUV light source apparatus according to a seventh embodiment of the present invention.
Figure 21:
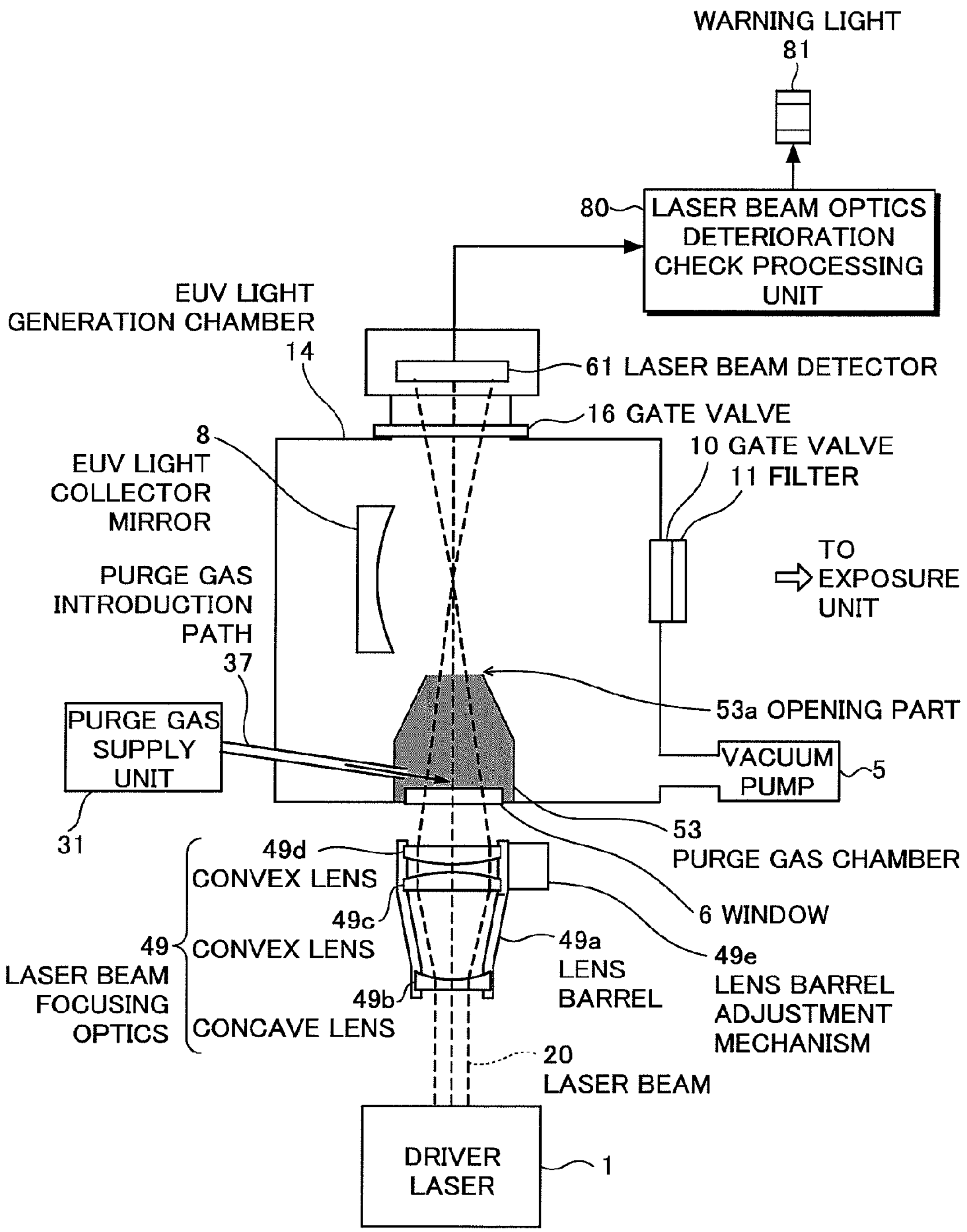
FIG. 21 is a schematic diagram showing a state without EUV light generation in the EUV light source apparatus according to the seventh embodiment of the present invention.

FIG. 20 and FIG. 21 are schematic diagrams showing the EUV light source apparatus according to the present embodiment. FIG. 20 is a schematic diagram showing a state of EUV light generation in the EUV light source apparatus according to the present embodiment, and FIG. 21 is a schematic diagram showing a state without EUV light generation in the EUV light source apparatus according to the present embodiment. Note that, FIG. 20 and FIG. 21 omit the target material supply unit 3 and the target material collecting cylinder 7 (refer to FIG. 1) from the drawings and the target material is assumed to be injected in the direction perpendicular to the page.

First, mainly with reference to FIG. 20, the operation in the case of EUV light generation in the EUV light source apparatus according to the present embodiment will be described, and then, mainly with reference to FIG. 21, the operation in the case without EUV light generation in the EUV light source apparatus according to the present embodiment will be described.

As shown in FIG. 20, the laser beam 20 emitted from the driver laser 1 to the upward direction in the drawing is input into a laser beam focusing optics 49.

The laser beam focusing optics 49 includes a lens barrel 49*a*, a concave lens 49*b* and convex lenses 49*c* and 49*d* disposed within the lens barrel 49*a*, and a lens barrel adjustment mechanism 49*e*. The laser beam 20 input into the laser beam focusing optics 49 is diffused by the concave lens 49*b*, collimated by the convex lens 49*c*, and focused by the convex lens 49*d*. The laser beam 20 focused by the convex lens 49*d* is transmitted through the window 6 to be input into an EUV light generation chamber 14. Note that the lens barrel adjustment mechanism 49*e* can adjust the position and the angle (tilt angle) of the lens barrel 49*a*.

The laser beam 20 input into the EUV light generation chamber 14 is focused onto the path of the target material. Thereby, the target material is excited into plasma and the EUV light 21 is generated.

The EUV light collector mirror 8 reflects the generated EUV light 21 to the rightward direction in the drawing to focus the EUV light 21 onto the IF (intermediate focusing point). The EUV light 21 having been reflected by the EUV light collector mirror 8 is transmitted through a gate valve 10 and a filter 11 provided to the EUV light generation chamber 14. The EUV light 21 focused onto the IF (intermediate focusing point) is guided to the exposure unit or the like via the transmission optics hereinafter.

The EUV light source apparatus further includes a purge gas supply unit 31 and a purge gas introduction path 37 for introducing the purge gas injected from the purge gas supply unit 31 to the surface of the window 6 on the inner side of the EUV light generation chamber 14.

Further, a purge gas chamber 53 surrounding the window 6 is attached to the inner wall of the EUV light generation chamber 14. The purge gas chamber 53 has a tapered cylindrical shape at the upper part thereof in the drawing and is provided with an opening part 53*a* on the top thereof (upper side in the drawing) for transmitting the laser beam 20 having been transmitted through the window 6.

Next, the operation in the case without EUV light generation in the EUV light source apparatus according to the present embodiment will be described with reference to FIG. 21.

In the case without EUV light generation in the EUV light source apparatus according to the present embodiment, the laser beam having been transmitted through the gate valve 16 is input into the laser beam detector 61.

In the case without EUV light generation in the EUV light source apparatus according to the present embodiment, the laser beam optics deterioration check processing unit 80 carries out the processing shown in the flowchart of FIG. 5 using the signal or data from the laser beam-detector 61.

Note that, while the three lenses (concave lens 49*b* and convex lenses 49*c* and 49*d*) are used in the present embodiment, four or more lenses may be used for improving the aberration.

(Eighth Embodiment)

Figure 22:
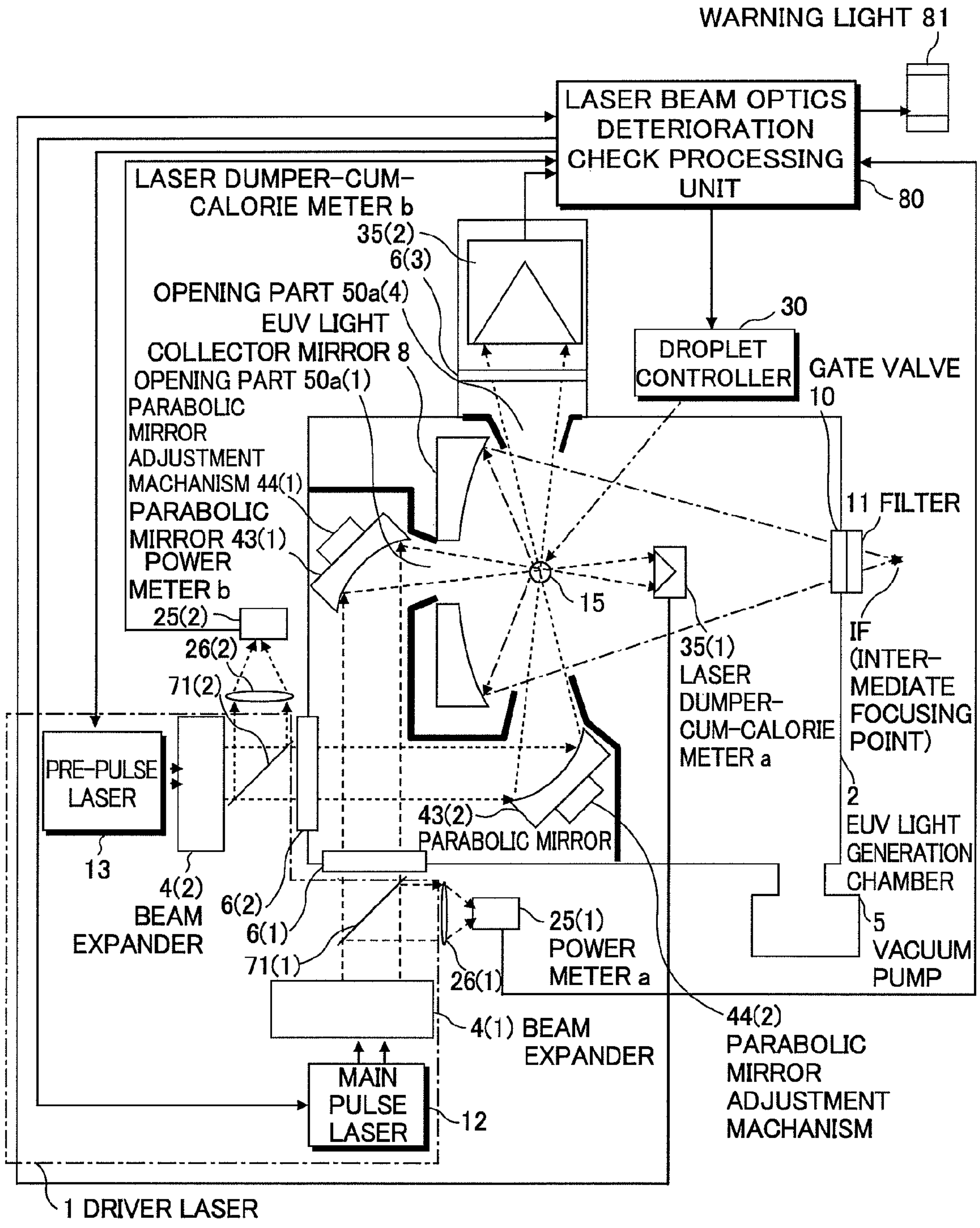
FIG. 22 is a schematic plan view showing an outline of an EUV light source apparatus according to an eighth embodiment of the present invention.
Figure 23:
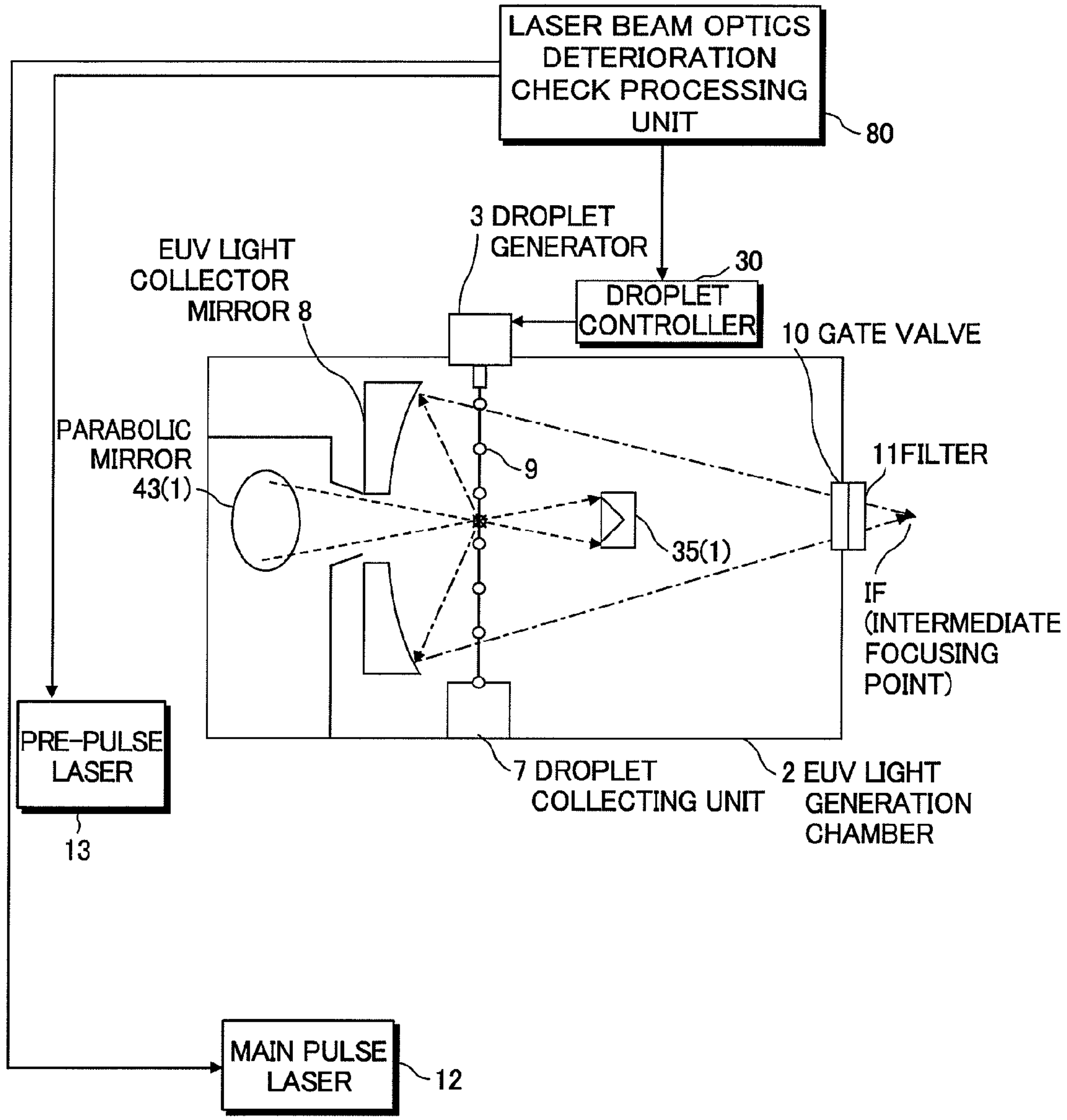
FIG. 23 is a schematic elevation view of the EUV light source apparatus according to the eighth embodiment of the present invention.

FIG. 22 is a schematic plan view showing an outline of an EUV light source apparatus according to an eighth embodiment of the present invention, and FIG. 23 is a schematic elevation view thereof.

The EUV light source apparatus according to the present embodiment has a feature that deterioration or the like can be detected accurately in the laser beam focusing optics of the EUV light generation chamber and thereby a quick action can be taken against the deterioration or variation of the EUV light generation efficiency. As shown in the drawings, the EUV light source apparatus of the present embodiment comprises a driver laser 1, an EUV light generation chamber 2, a target material supply unit 3, and a laser beam focusing optics including a beam expander.

The EUV light source apparatus of the present embodiment is a system performing efficient plasma light generation by applying a pre-pulse laser beam to a droplet of the target material for making the target to be expanded or turning the target into plasma, and applying a main pulse laser beam to the expanded target or the target turned into plasma.

While the driver laser 1 is an oscillation type amplification laser apparatus generating driver laser beam used for exciting the target material, the driver laser 1 in the present embodiment is configured with a main pulse laser 12 and a pre-pulse laser 13 as shown by the dashed-dotted line. For the driver laser 1, it is possible to use various publicly known lasers (e.g., ultra-violet laser such as KrF, XeF, infra-red laser such as Ar, $CO_2$, YAG, etc., and the like).

The EUV light generation chamber 2 is a vacuum chamber where the EUV light is generated. To the EUV light generation chamber 2, windows 6(1) and 6(2) are attached for transmitting the laser beams generated from the main pulse laser 12 and the pre-pulse laser 13 of the driver laser 1 into the EUV light generation chamber 2. Further, within the EUV light generating chamber 2 are disposed with a target injection nozzle of a droplet generator 3, a droplet collecting unit 7, and an EUV light collector mirror 8.

The droplet generator 3 supplies the target material used for generating the EUV light into the EUV light generation chamber 2 via the target injection nozzle. A part of the supplied target material which remains without being irradiated with the laser beam is collected by the droplet collecting unit 7. Various materials known in public (e.g., tin (Sn), xenon (Xe), etc.) can be used for the target material.

Further, the state of the target material may be any of solid, liquid, and gas, and the target material may be supplied to a space within the EUV light generation chamber 2 in any publicly known state such as a continuous flow (target jet flow) and liquid drops (droplets). For example, in the case of using a liquid xenon (Xe) target for the target material, the droplet generator 3 is configured with a gas cylinder supplying high purity xenon gas, a mass flow controller, a refrigeration unit for liquefying the xenon gas, a target injection nozzle, etc. On the other hand, in the case of using tin (Sn) for the target material, the droplet generator 3 is configured with a heating device heating Sn for liquefaction, a target injection nozzle, etc. Further, for generating the droplets, a vibration device such as a piezoelectric element is added to the above configuration.

Note that, by control of a droplet controller 30, the droplet generator 3 supplies the target material into the EUV light generation chamber 2 when the EUV light source apparatus generates the EUV light, and does not supply the target material into the EUV light generation chamber 2 when the EUV light source apparatus does not generate the EUV light.

A pre-pulse laser beam focusing optics is configured with a beam expander 4(2), a window 6(2), and a parabolic mirror 43(2), and focuses the laser beam emitted from the pre-pulse laser 13 so as to form a focus on the path of the target material. Further, a main pulse laser beam focusing optics is configured with a beam expander 4(1), a window 6(1), and a parabolic mirror 43(1), and focuses the laser beam emitted from the main pulse laser 12 so as to form a focus on the target material 9 which has been expanded by the pre-pulse laser. Thereby, the target material 9 is excited into plasma and the EUV light is generated. Note that the laser beam focusing optics may be configured with a single optical element (e.g., single convex lens or the like) and also may be configured with a plurality of optical elements. In the case of configuring the laser beam focusing optics with a plurality of optical elements, it is possible to dispose some of the optical elements within the EUV light generation chamber 2.

Note that, in the case of using an excimer laser or a YAG laser of a harmonic wave or a fundamental wave of YAG laser for the main pulse laser 12 or the pre-pulse laser 13, it is preferable to use a material less absorbing the laser beam such as synthetic quartz, $CaF_2$, and $MgF_2$, for the material of the concave lens and the convex lens which compose the expander 4, and for the material of the window 6. On the other hand, in the case of using an infra-red laser such as $CO_2$ laser for the main pulse laser 12, ZnSe, GaAs, Ge, Si, diamond, etc are suitable for the material of the concave lens, the convex lens, and the window 6. Further, it is preferable to provide an anti-reflection (AR) coating of a dielectric multi-layer film on each surface of the concave lens, the convex lens, and the window 6.

The EUV light collector mirror 8 is an ellipsoid-shaped concave mirror with a Mo/Si film formed on the surface thereof for reflecting light with a wavelength of 13.5 nm, for example, in a high reflectance, and focuses the generated EUV light by reflection to guide the EUV light to the transmission optics. Further, this EUV light is guided to the exposure unit or the like via the transmission optics.

As shown in FIG. 22, after the pre-pulse laser beam is expanded by the beam expander 4(2), a part of the beam is made to branch by the beam splitter 71(2) and input into a power meter 25(2) via a convex lens 26(2), and thereby the output power Wp0 of the pre-pulse laser is monitored before the pre-pulse laser beam is input into the EUV light generation chamber 2.

On the other hand, the pre-pulse laser beam transmitted through the beam splitter 71(2) transmits through the window 6(2) to enter the EUV light generation chamber 2, irradiates and reflects on an off-axis parabolic mirror 43(2), and is focused to be applied to the droplet 9 in synchronization with timing that the droplet 9 supplied from the droplet generator 3 reaches a predetermined position. Thereby, the droplet 9 is made instantly to expand or excited into plasma at a part irradiated with the laser beam.

Meanwhile, after the main pulse laser beam is expanded by the beam expander 4(1), a part of the beam is split to branch by the beam splitter 71(1) and input into a power meter 25(1) via a convex lens 26(1), and thereby the output power Wm0 of the main pulse laser beam is monitored before the main pulse laser beam is input into the EUV light generation chamber 2. The remaining split part of the main pulse laser beam is transmitted through the window 6(1) to enter the EUV light generation chamber 2, irradiates and reflects on an off-axis parabolic mirror 43(1), and is focused to be applied to the target expanded by the pre-pulse laser beam.

In this manner, since the main pulse laser beam is applied to the droplet 9 at the part which is expanded or exited into plasma by the pre-pulse laser beam application, it is possible to realize EUV light generation having a high efficiency of conversion to the EUV light.

Note that, for the substrate material of the parabolic concave mirror 43(2) for focusing the pre-pulse laser beam, it is possible to use synthetic quartz, $CaF_2$, Si, Zerodur (registered trade mark), Al, Cu, Mo, or the like, and it is preferable to provide a high reflection coating of a dielectric multi-layer film on the surface of such a substrate.

Further, in the case of using a $CO_2$ laser for the main pulse laser 12, Cu or the like having a built-in cooling device may be used for the substrate material of the focusing parabolic concave mirror 43(1), and preferably a high reflection coating of Au is provided on the surface of such a substrate.

The EUV light source apparatus of the present embodiment is provided with a laser dumper-cum-calorie meter 35(1) for the main pulse laser beam and a laser dumper-cum-calorie meter 35(2) for the pre-pulse laser beam, and can measure energies of the main pulse laser beam and the pre-pulse laser beam at the target position (focusing point 15).

When the energy of the laser beam at the target position (focusing point 15) is measured, the laser beam optics deterioration check processing unit 80 sends an instruction to the droplet controller 30 and the main-pulse laser 12 or the pre-pulse laser 13, not to make the droplet to exist at the focusing point 15 at timing of laser beam focusing and irradiating.

The pre-pulse laser beam is once focused on the focusing point 15 by the parabolic mirror 43(2), made to pass through the focusing point without hitting the droplet, made to pass through an opening of opening part 50_a_(4) while being diffused after that, transmitted through a window 6(3), and input into the laser dumper-cum-calorie meter 35(2) to be absorbed. The calorie meter of the laser dumper-cum-calorie meter 35(2) detects the energy Wp of the pre-pulse laser at the focusing point 15.

Further, the main pulse laser beam is once focused on the focusing point 15 by the parabolic mirror 43(1), made to pass through the focusing point 15 without hitting the droplet, and input into the laser dumper-cum-calorie meter 35(1) to be absorbed, while being diffused after that. The calorie meter of the laser dumper-cum-calorie meter 35(1) detects the energy Wm of the main pulse laser at the focusing point 15.

Note that it is preferable to dispose a debris shield as shielding means surrounding any parts with walls except a funnel-shaped opening part directed toward the focusing point 15, for protecting each of the windows 6(1), 6(2), and 6(3) and the parabolic mirrors 43(1) and 43(2) from the debris.

As shown in FIG. 23, the laser beam focusing point 15 is a cross point where the main pulse laser beam path parallel to the page in the drawing, the pre-pulse laser beam path perpendicular to the page in the drawing, and the trajectory of the droplet 9 intersect one another. Note that, in the case of a metal target such as Sn, the center position of the target, which is expanded or excited into plasma, sometimes shifts a little bit, when the target is expanded or excited into plasma by the pre-pulse laser beam. In such a case, the focusing points of the pre-pulse laser beam and the main pulse laser beam do not always meet each other. However, the shift between both focusing points is so small that errors are not caused in the energy detections of both laser beams. While both focusing points 15 are described to meet each other in the specification, even if both focusing points are shifted from each other, the shift is so small that there is no problem for implementing the present embodiment.

Here, three methods will be described in the following, as the method of making the droplet not to exist at the focusing point 15 when the radiation energy of the laser beam is measured.

(a) The generation of the droplet is interrupted and the energies of the main pulse laser beam and the pre-pulse laser beam are measured. This method has an advantage that the measurement can be carried out without changing the optical axes of both laser beams.

(b) The generation timing of the droplet or the oscillation timing of the main pulse laser beam or the pre-pulse laser beam is shifted, and the laser beam energy is measured when the collision between the droplet and the laser beam is avoided. When the generation of the droplet is once interrupted, a considerable time is required for generating the droplet normally again. This method, which only shifts the droplet generation timing, has an advantage that only a short time is required for return to the normal state. In addition, the optical axis of the laser beam is not changed. Further, in the laser beam energy measurement method, in which the collision between the droplet and the laser beam is avoided by the oscillation timing shift of the main pulse laser beam or the pre-pulse laser beam, only the laser oscillation timing needs to be changed while the droplet generation timing needs not to be changed, and thereby there is an advantage that start-up of the EUV light requires only a short time, since both laser beam axes and the droplet generation can maintain extremely stable states.

(c) The optical axes of the main pulse laser beam and the pre-pulse laser beam are shifted slightly from the target while the generation of the droplet is maintained without change, such that the respective laser beams do not hit the droplet and the target expanded or excited into plasma, and then the energy of the laser beams is measured. Since the laser beam energy is detected while the droplet is generated stably without interruption of the droplet dropping, there is an advantage that the start-up requires only a short time after the return.

Figure 24:
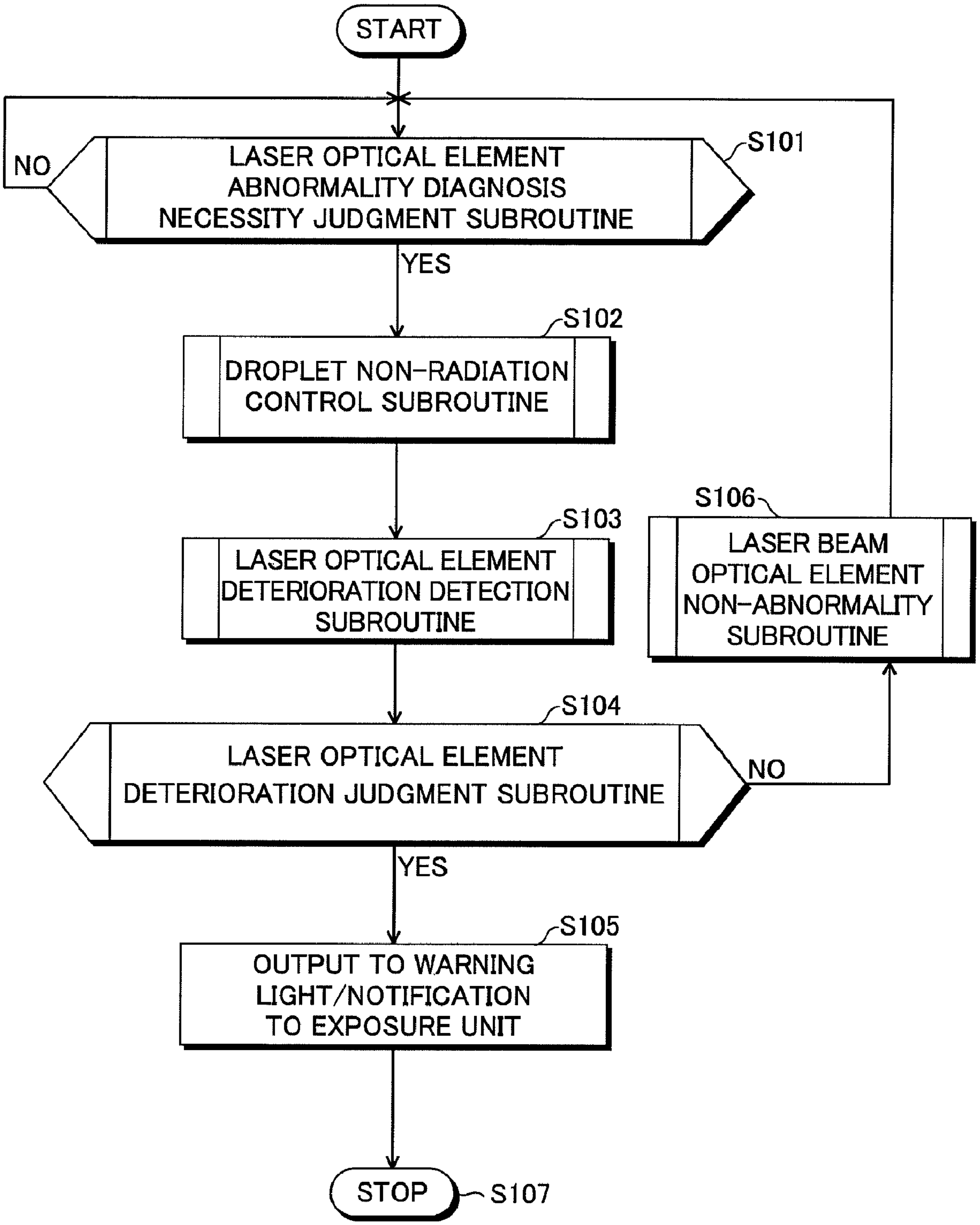
FIG. 24 is a flowchart illustrating a procedure example of laser-optics deterioration detection which is carried out in the EUV light source apparatus of the eighth embodiment of the present invention.

FIG. 24 is a main flowchart illustrating an example of a detection sequence for the deterioration of the laser beam optics, which is carried out by the laser beam optics deterioration check processing unit 80 in the EUV light source apparatus of the present embodiment.

The laser beam optics deterioration check processing unit 80 first carries out a laser optical element abnormality diagnosis necessity judgment subroutine (S101), and determines whether or not to carry out a deterioration diagnosis of the laser optical element. Here, if the deterioration diagnosis is determined not to be carried out (NO), the process returns to S101 again and the subroutine is carried out repeatedly until the deterioration diagnosis is determined to be carried out.

On the other hand, if the deterioration diagnosis of the optical element is determined to be carried out (YES), the process goes to the next step and a droplet non-radiation control subroutine (S102) is carried out. Subsequently, a laser optical element deterioration detection subroutine (S103) is carried out, and according to the result, laser optical element deterioration judgment subroutine (S104) is carried out for the pre-pulse laser and the main pulse laser. If the deterioration is determined to exist (YES), the process goes to S105, and the operator is notified about the deterioration of the optical element by an output to the warning light and also the EUV light source apparatus is stopped after notification to the controller of the exposure unit (S107). On the other hand, if the deterioration is determined to be in an allowable range (NO) when the laser optical element deterioration judgment subroutine (S104) is carried out for the pre-pulse laser and the main pulse laser, the process goes to a laser optical element non-abnormality subroutine (S106) and, after that, returns to the first step S101 and this routine is repeated.

Figure 25:
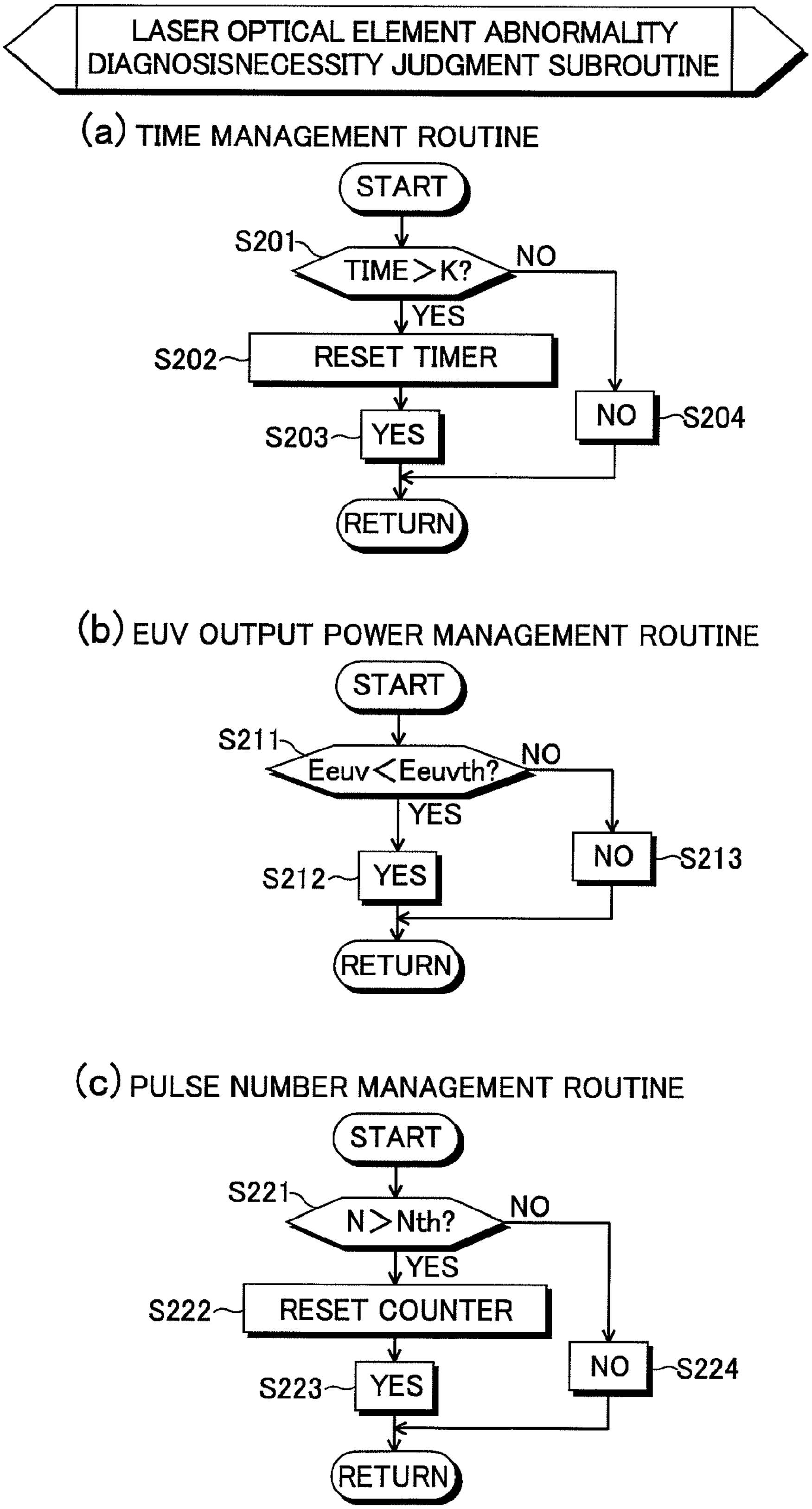
FIG. 25 is a flowchart showing contents of a laser optical element abnormality diagnosis necessity judgment subroutine.

FIG. 25 is a flowchart showing the contents of the laser optical element abnormality diagnosis necessity judgment subroutine (S101).

As a criterion for judging necessity of the optical element abnormality diagnosis, there are used a criterion based on time elapsed from the preceding diagnosis, a criterion based on the EUV output power, and a criterion based on the number of laser beam pulses accumulated from the preceding diagnosis. Some of these criterions may be selected for use, or all these criterions may be used and, if any one of the criterions is satisfied, the abnormality diagnosis may be carried out.

FIG. 25 shows (a) a time management routine, (b) an EUV output power management routine, and (c) a pulse number management routine, assuming that any one is carried out thereamong. Note that, when these routines are connected serially, and, if a NO result is found in one routine, the process goes to the next routine, all of the conditions can be checked and, if any one of the conditions is satisfied, the abnormality diagnosis can be carried out.

(a) The time management routine is a routine for the case that the abnormality diagnosis is carried out at a constant period. By use of a timer, it is determined whether or not a time measurement result reaches K hours of the period (S201). If the time has not reached K hours, the abnormality diagnosis is determined to be unnecessary (NO), and this routine is terminated. Further, if K hours have elapsed, the timer is reset (S202), the abnormality diagnosis is determined to be necessary (YES) (S203), and the time management routine is terminated.

(b) The EUV output power management routine is a routine for the case that the abnormality diagnosis is carried out unless the EUV output power reaches a predetermined value.

The EUV output power Eeuv measured by an EUV output power measurement equipment is compared with a predetermined threshold value Eeuvth (S211). If Eeuv is not smaller than Eeuvth, the abnormality diagnosis is determined to be unnecessary (NO) (S213) and this routine is terminated. If Eeuv is smaller than Eeuvth, the abnormality diagnosis is determined to be necessary (YES) (S212) and the EUV output power routine is terminated.

(c) The pulse number management routine is a routine for the case that the abnormality diagnosis is carried out every time the number of EUV light radiation pulses reaches a predetermined number.

The number of the EUV light pulses N is counted by a counter, and the counted number of the counter is compared with a predetermined threshold value Nth (S221). If N does not exceed Nth, the abnormality diagnosis is determined to be unnecessary (NO) (S224) and this routine is terminated. If N exceeds Nth, the counter is reset (S222), the abnormality diagnosis is determined to be necessary (YES) (S223), and the pulse number management routine is terminated.

Figure 26:
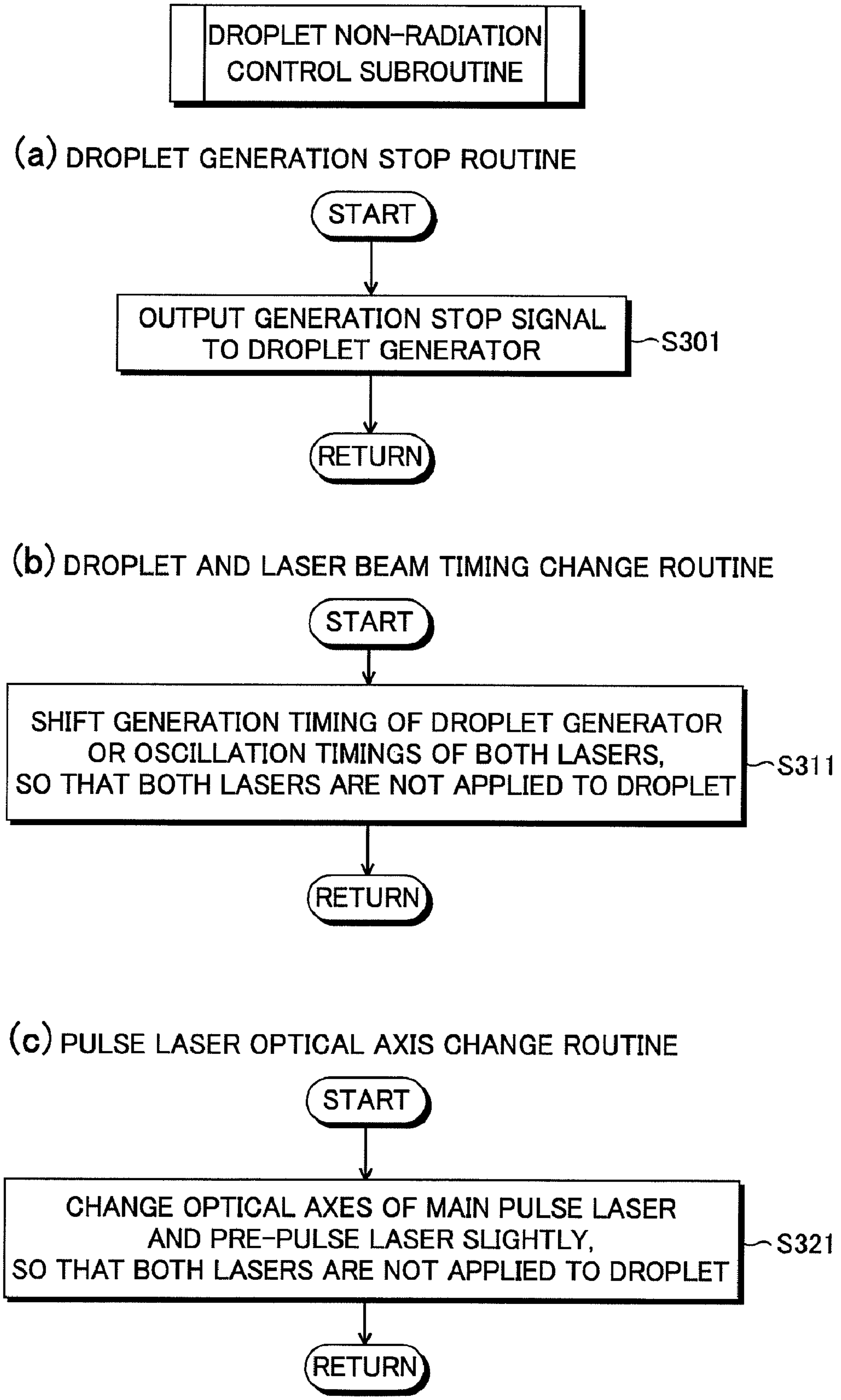
FIG. 26 is a flowchart showing contents of a droplet non-radiation control subroutine.

FIG. 26 is a flowchart showing the contents of the droplet non-radiation control subroutine (S102). The laser beam optics deterioration check processing unit 80 preliminarily selects and carries out one of the three methods of making the droplet not exist at the laser beam focusing point 15 for measuring the laser beam radiation energy. Accordingly, the droplet non-radiation control subroutine (S102) has (a) a routine for interrupting the droplet generation, (b) a routine for changing the timing between the droplet and the laser beam, and (c) a routine for changing the pulse laser optical axis, and the laser beam optics deterioration check processing unit 80 selects and carries out any one of the routines.

(a) The routine for interrupting the droplet generation is a routine for outputting droplet generation interruption signals to the droplet generator 3 via the droplet controller 30 (S301) and returns after the interruption of the droplet generation. By execution of this routine, the pre-pulse laser beam and the main pulse laser beam become to be input into the calorie meters without irradiating the droplet.

(b) The routine for changing the timing between the droplet and the laser beam is a routine which shifts the droplet generation timing in the droplet generator 3 via the droplet controller 30 from the oscillation timings of the pre-pulse laser beam and the main pulse laser beam, or shifts the oscillation timings of these pulse laser beams via a pre-pulse laser controller and a main pulse laser controller, respectively, from the droplet generation timing, and thereby the pulse laser beam does not irradiate the droplet (S311) and the routine returns.

(c) The routine for changing the pulse laser optical axis is a routine which changes the axes of the pre-pulse laser and the main pulse laser slightly from the path of the droplet (S321), and thereby makes both of the laser beams to be input into the calorie meters without hitting the droplet and then returns. Since the diameter of the droplet is approximately 30 μm to 100 μm, it is sufficient to shift the optical axes by several hundred μm and the shifts of the optical axes do not affect the measured values of the pulse laser energies.

Figure 27:
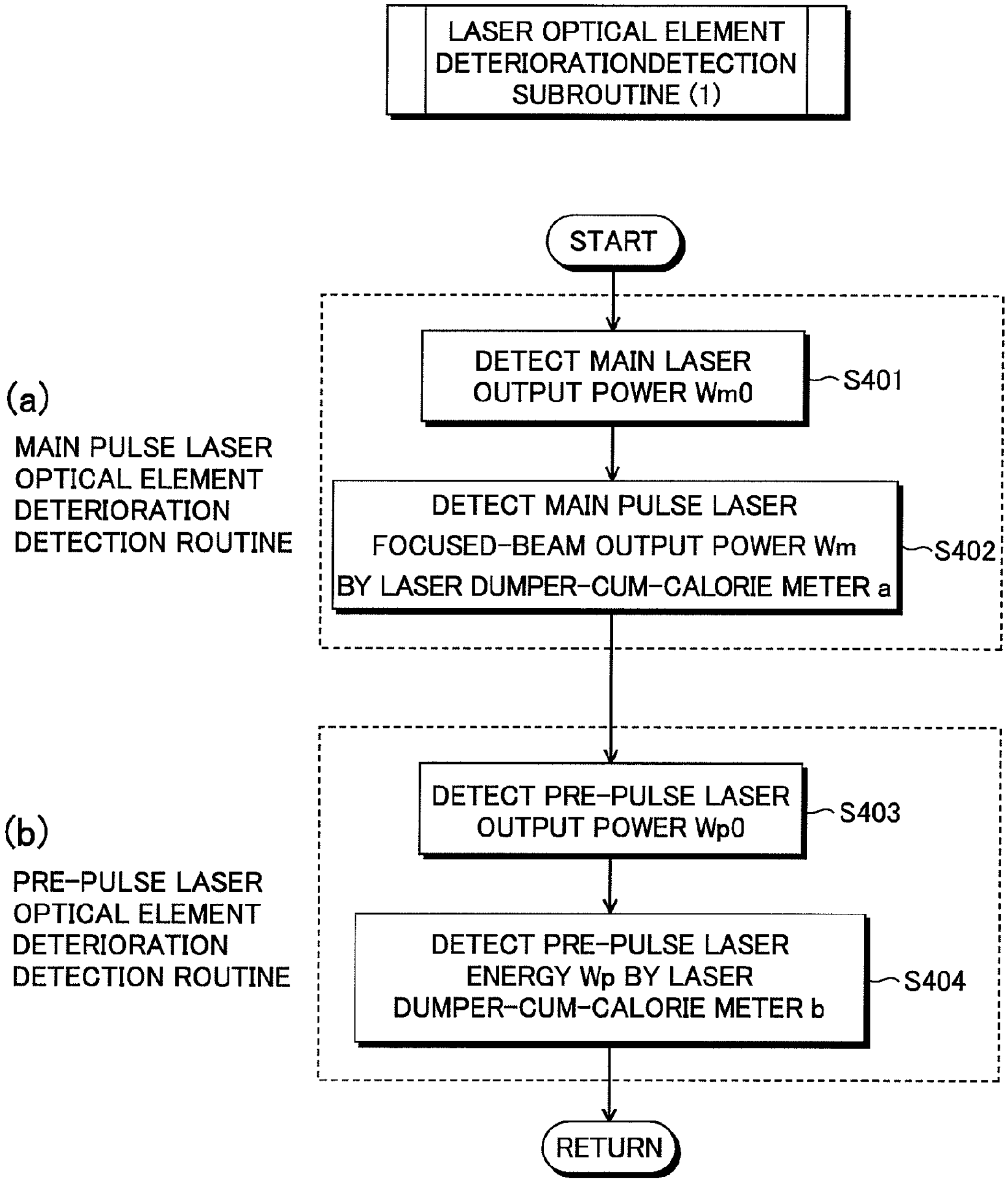
FIG. 27 is a flowchart showing contents of a first example for a laser optical element deterioration detection subroutine.

FIG. 27 is a flowchart showing the contents of a first example for the laser optical element deterioration detection subroutine (S103). The laser beam optics deterioration check processing unit 80 measures the laser beam radiation energy at the focusing point 15 and detects the state of the laser optical element deterioration by the output power reduction. The laser optical element deterioration detection subroutine (S103) is configured with (a) a routine for detecting the deterioration of the main pulse laser optical element, and (b) a routine for detecting the deterioration of the pre-pulse laser optical element.

(a) The main pulse laser optical element deterioration detection routine first detects the output power Wm0 of the main pulse laser before the input into the EUV light generation chamber 2 with the power meter 25(1) for the main pulse laser (S401). Then, the main pulse laser optical element deterioration detection routine measures the output power Wm of the main pulse laser at the focusing point 15 with the laser dumper-cum-calorie meter for the main pulse laser 35(1) (S402), and the process goes to the next step.

(b) The pre-pulse laser optical element deterioration detection routine first detects the output power Wp0 of the pre-pulse laser before the input into the EUV light generation chamber 2 with the power meter 25(2) for the pre-pulse laser (S403). Then, the pre-pulse laser optical element deterioration detection routine measures the output power Wp of the pre-pulse laser at the focusing point 15 with the laser dumper-cum-calorie meter for the pre-pulse laser 35(2) (S404), and the process returns to the main routine.

Note that outputs of power monitors contained in the laser apparatuses can be utilized respectively for the output power Wm0 of the main pulse laser and the output power Wp0 of the pre-pulse laser before the input into the EUV light generation chamber 2.

Figure 28:
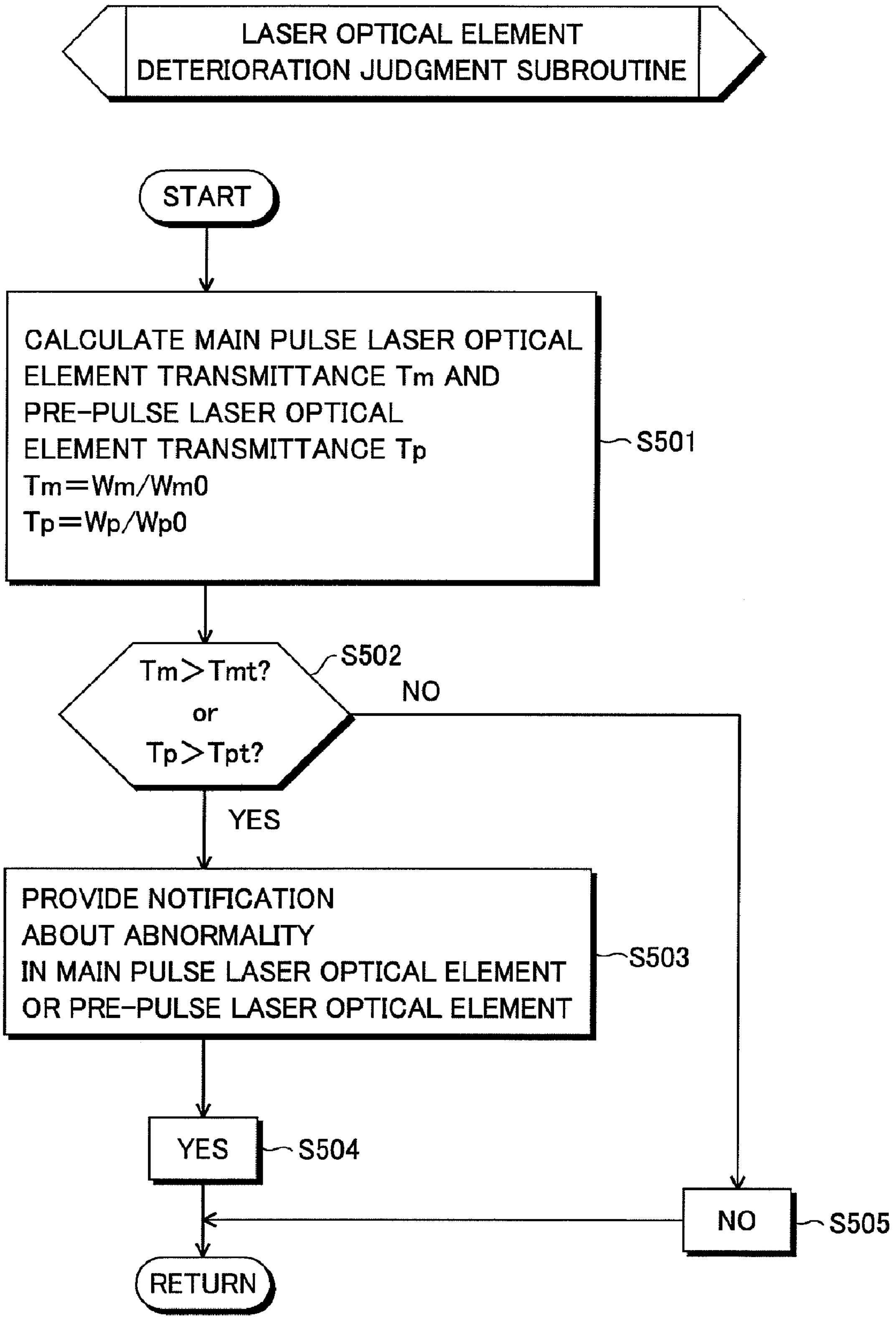
FIG. 28 is a flowchart showing contents of a laser optical element deterioration judgment subroutine.

FIG. 28 is a flowchart showing the contents of the laser optical element deterioration judgment subroutine (S104). The laser beam optics deterioration check processing unit 80 calculates a transmittance and judges the deterioration state of the optical element disposed within the EUV light generation chamber 2 among the optical elements used for the pre-pulse laser and the main pulse laser.

The laser optical element deterioration judgment subroutine (S104) first calculates total transmittances Tm and Tp of the optical elements used for the main pulse laser and the pre-pulse laser according to the following formula using the laser output powers Wm0 and Wp0 before the input into the EUV light generation chamber 2 and the laser output powers Wm and Wp at the focusing point 15, respectively (S501).

$$Tm=Wm/Wm0$$

$$Tp=Wp/Wp0$$

Next, the laser optical element deterioration judgment subroutine (S104) compares the total transmittances Tm and Tp with threshold values of the transmittances Tmt and Tpt, respectively (S502) and judges the deterioration of the optical element. If the total transmittance for the main pulse laser Tm is lower than the threshold value Tmt or the total transmittance for the pre-pulse laser Tp is lower than the threshold value Tpt, the optical element is determined to have the deterioration and the notification of abnormality is carried out (S503), and also the optical element is determined to have the deterioration (YES) (S504) and the process returns to the main routine. On the other hand, if the transmittances Tm and Tp do not reach the threshold value Tmt and Tpt, respectively, the optical elements are determined not to have the deterioration (NO) (S505) and the process returns to the main routine.

If the deterioration of the optical element in each of the pre-pulse laser and the main pulse laser is determined to be within the allowable range in the laser optical element deterioration judgment subroutine (S104), the laser beam optics deterioration check processing unit 80 carries out the laser optical element non-abnormality notification subroutine (S106).

Figure 29:
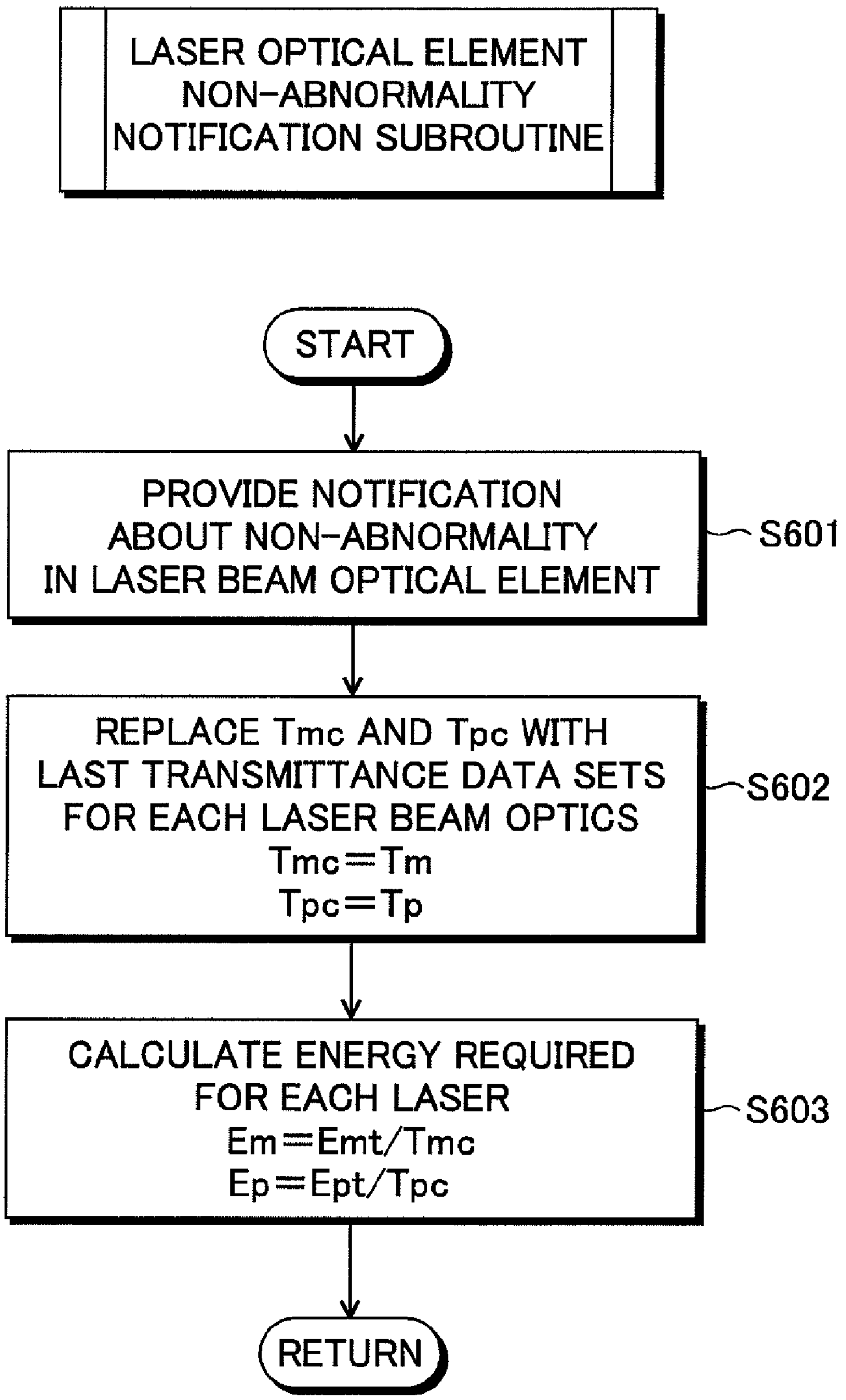
FIG. 29 is a flowchart showing contents of a laser optical element non-abnormality notification subroutine.

FIG. 29 is a flowchart showing the contents of the laser optical element non-abnormality notification subroutine (S106).

This subroutine first notifies the operators or the exposure unit that the laser optical element does not have abnormality (S601). Then this subroutine replaces the respective total transmittances Tmc and Tpc of the main pulse laser optical element and the pre-pulse laser optical element with the last measured values Tm and Tp (S602), respectively, to accurately reflect the current state to the criterion indexes.

$$Tmc=Tm$$

$$Tpc=Tp$$

Note that the transmittance changes in the optics of each laser may be recorded with time.

Further, required output energies Em and Ep for both of the pulse lasers are calculated by use of the following formulas from the total transmittances and laser beam energies Emt and Ept required at the focusing point 15, respectively (S603). After that, the process returns to the main flow.

$$Em=Emt/Tmc$$

$$Ep=Ept/Tpc$$

While not shown in the flowchart, the laser beam optics deterioration check processing unit 80 adjusts the output power of the laser apparatus according to this result. In the main flow, the energies of the main pulse laser 12 and the pre-pulse laser 13 are adjusted by use of the last transmittance values Tmc and Tpc of the main pulse laser optical element and the pre-pulse laser optical element, respectively.

The above processing provides the following advantages.

(1) Since the laser beam is focused to be applied to the droplet according to the last transmittance of the laser optics, it is possible to stabilize the pulse energy of the EUV light.

(2) By measuring the temporal change of the transmittance for the optics of each laser, it becomes possible to predict the deterioration of the laser optics and to carry out preventive repair and maintenance. For example, by preliminary warning, it is possible to exchange or repair parts at a time convenient for maintenance, avoiding an accidental shutdown of the EUV light source apparatus, and to reduce down time of the apparatus.

(Ninth Embodiment)

Figure 30:
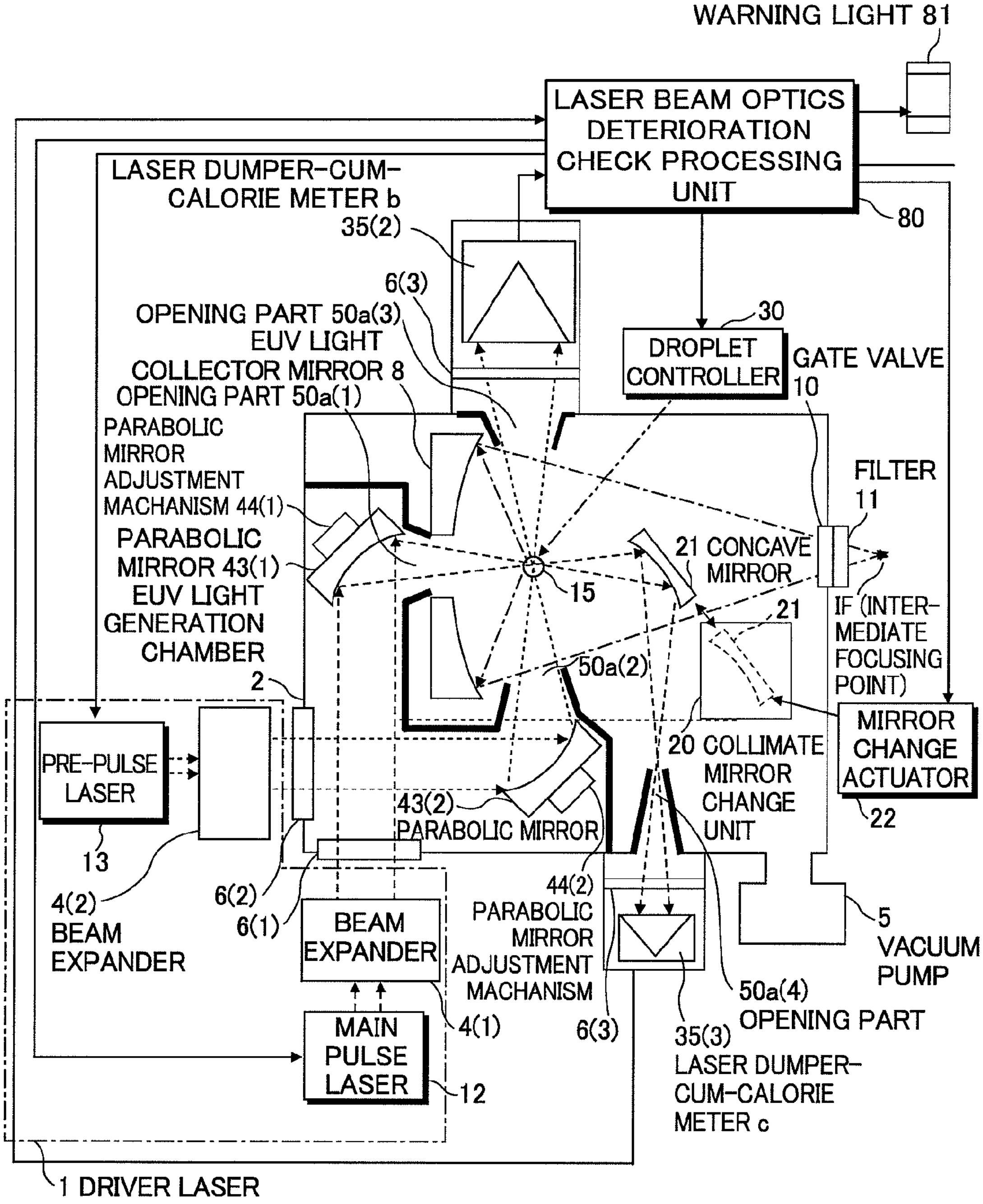
FIG. 30 is a schematic plan view showing an outline of an EUV light source apparatus according to a ninth embodiment of the present invention.

FIG. 30 is a schematic plan view showing an outline of an EUV light source apparatus according to a ninth embodiment of the present invention. The EUV light source apparatus of the present embodiment is different from the EUV light source apparatus of the eighth embodiment only in that the calorie meter for the main pulse laser beam is disposed so as to be protected from the debris, and the other constituents are almost the same.

That is, the laser dumper-cum-calorie meter 35(3) for the main pulse laser beam is disposed outside an opening part 50*a*(4) which is provided to the wall of the EUV light generation chamber 2, instead of being disposed immediately close to the focusing point 15. Then, the main pulse laser beam, which has been focused once onto the focusing point 15 and is being diffused, is reflected by the concave mirror 21 to be focused again, made to pass through an opening of opening part 50*a*(4) forming a debris shield, transmitted through the window 6(3), and made to reach the laser dumper-cum-calorie meter 35(3).

Further, the concave mirror 21 is usually accommodated in a protection chassis of a focusing mirror (or collimator mirror) exchange unit 20 to be protected from the debris, and, only in the measurement, inserted into the optical path of the main pulse laser by a mirror exchange actuator 22. Accordingly, the concave mirror 21 is not stained with the debris and resistant to the deterioration.

Moreover, the laser dumper-cum-calorie meter 35(3) is effectively prevented by the debris shield and the window 6(3) from being deteriorated by the debris.

When measuring the total transmittance of the main pulse laser optical element, it is possible to obtain an accurate measurement result by using the extracted concave mirror 21 which is not deteriorated by stain with the debris.

Note that, while FIG. 30 does not illustrate power meters measuring the output powers of the main pulse laser beam and the pre-pulse laser beam before the input into the EUV chamber 2, output powers which are measured by the laser output power monitors contained in the laser apparatuses, can be used instead as Wm0 and Wp0, respectively.

In addition, after the measurement of the main pulse laser beam energy, the concave mirror 21 without deterioration may be returned into the chassis of the focusing mirror (or collimator mirror) exchange unit 20 and the usual original concave mirror 21 may be made to return for dumping the main pulse laser beam input into the concave mirror to the laser damper-cum-calorie meter 35(3). Further, a laser dumper may be provided in a down-stream side of the concave mirror 21 and the laser beam may be dumped to the laser dump when the concave mirror 21 is evacuated.

Figure 31:
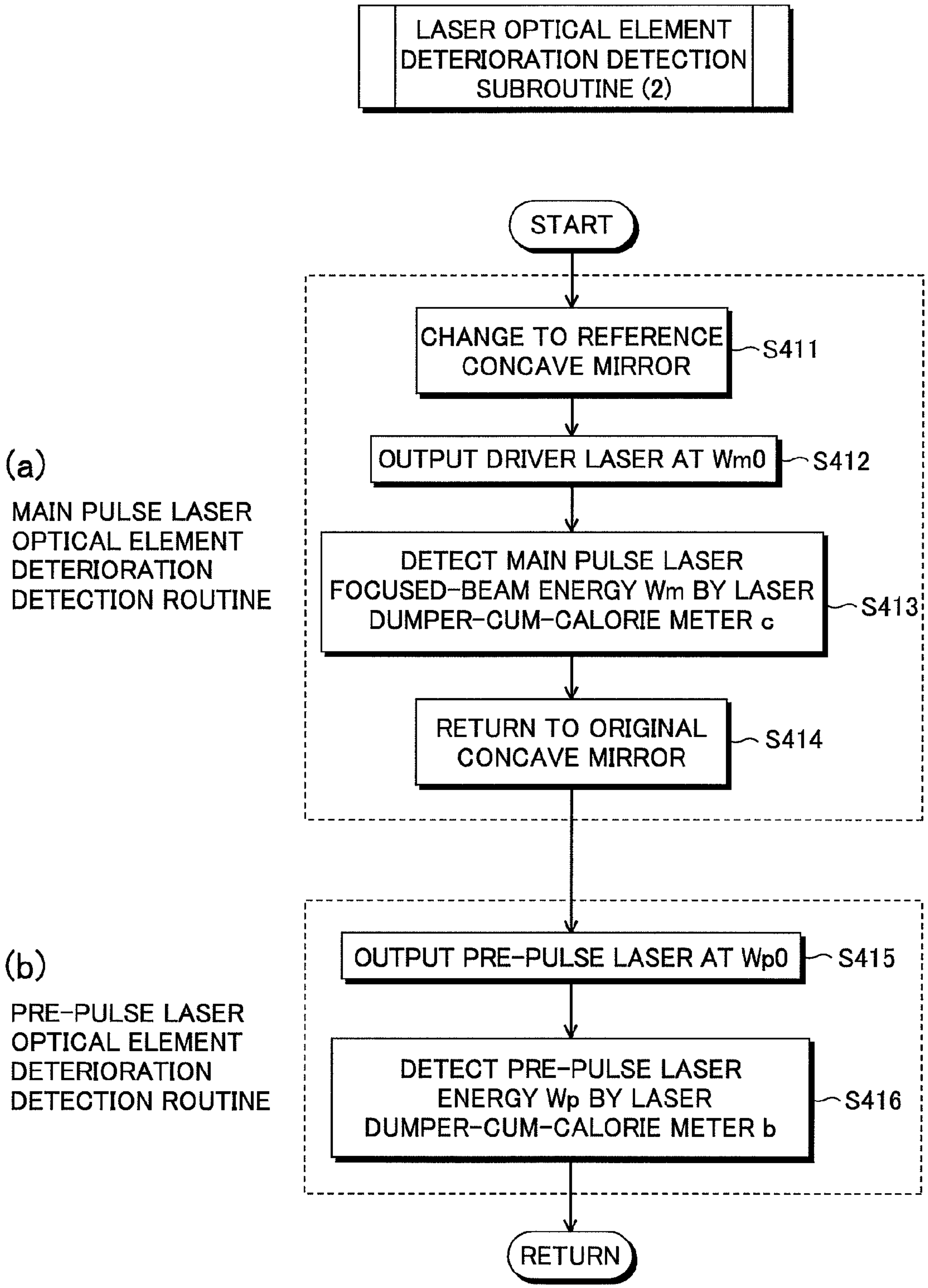
FIG. 31 is a flowchart showing contents of a second example of a laser optical element deterioration detection subroutine which is applied to the ninth embodiment of the present invention.

FIG. 31 is a flowchart showing the contents of a second example of the laser optical element deterioration detection subroutine (S103) which is used instead of the first example of the laser optical element deterioration detection subroutine when the main flowchart for the EUV light source apparatus of the present invention is applied to the ninth embodiment. Main difference of the second subroutine from the first subroutine shown in FIG. 27 is mainly in the main pulse laser optical element deterioration detection routine (a), and other part does not have a big difference. In the following, the second example of the laser optical element deterioration detection subroutine (S103) will be described.

In (a) the main pulse laser optical element deterioration detection routine of the second example of the laser optical element deterioration detection subroutine (S103), first the reference concave mirror 21 without stain with the debris is extracted from the chassis of the focusing mirror (collimator mirror) exchange unit 20 and disposed in the measurement optical path (S411).

Next, the main pulse laser beam is output having a power locked at Wm0 by use of the power monitor contained in the main pulse laser apparatus (S412). The output power Wm of the main pulse laser beam at the focusing point 15 is measured by laser dumper-cum-calorie meter 35(3) for the main pulse laser (S413), and the reference concave mirror 21 is replaced by the original mirror (S414). Then, the process goes to the next (b) pre-pulse laser optical element deterioration detection routine.

(b) In the pre-pulse laser optical element deterioration detection routine, first the pre-pulse laser apparatus outputs the pre-pulse laser beam so as to have the power of Wp0 (S415). Then, the output power Wp of the pre-pulse laser beam at the focusing point 15 is measured by the laser dumper-cum-calorie meter 35(2) for the pre-pulse laser (S416), and the process returns to the main routine.

(Tenth Embodiment)

Figure 32:
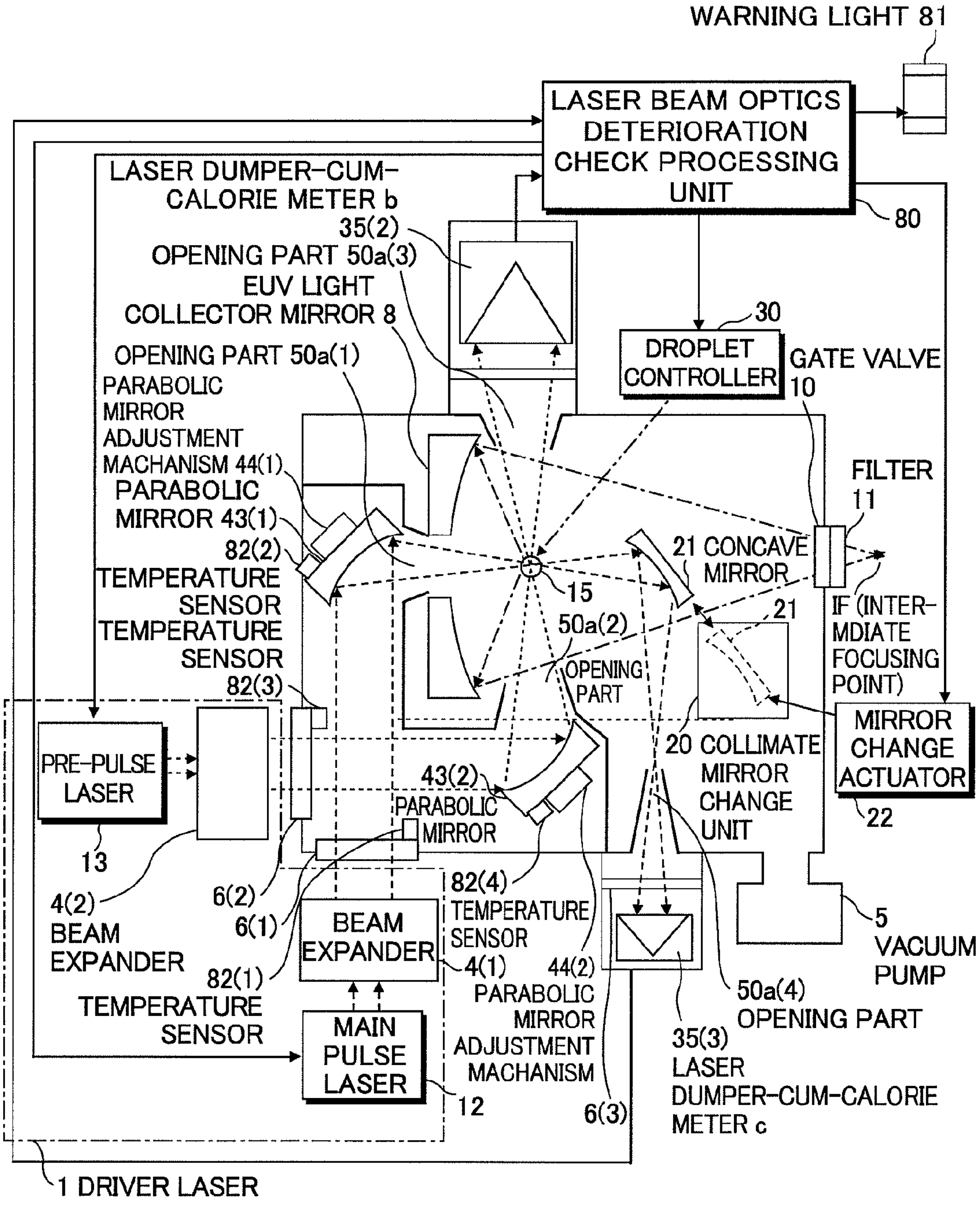
FIG. 32 is a schematic plan view showing an outline of an EUV light source apparatus according to a tenth embodiment of the present invention.

FIG. 32 is a schematic plan view showing an outline of an EUV light source apparatus according to a tenth embodiment of the present invention. The EUV light source apparatus of the present embodiment has a feature that a temperature monitor is provided to the laser optical element in the EUV light source apparatus of the ninth embodiment shown in FIG. 29. The other constituents are almost the same.

That is, temperature sensors 82(1), 82(2), 82(3), and 82(4), such as thermo-couples, platinum resistance temperature detectors, and radiation thermometers, are disposed at the window 6(1) and the parabolic mirror 43(1) for the main pulse laser, and the window 6(2) and the parabolic mirror 43(2) for the pre-pulse laser, so as to detect the deterioration in each of the optical elements by detecting temperature thereof, since the deterioration of the optical element generates heat and increases temperature thereof.

This method has an advantage that it is possible to know which individual optical element is deteriorated.

In addition to (a) the time management routine, (b) the EUV output power management routine, and (c) the pulse number management routine, the tenth embodiment uses (d) an optical element temperature management routine in parallel as a routine judging necessity of the optical element abnormality diagnosis in the laser optical element abnormality diagnosis necessity judgment subroutine (S101), when the main flowchart shown in FIG. 24 is applied to the tenth embodiment.

Figure 33:
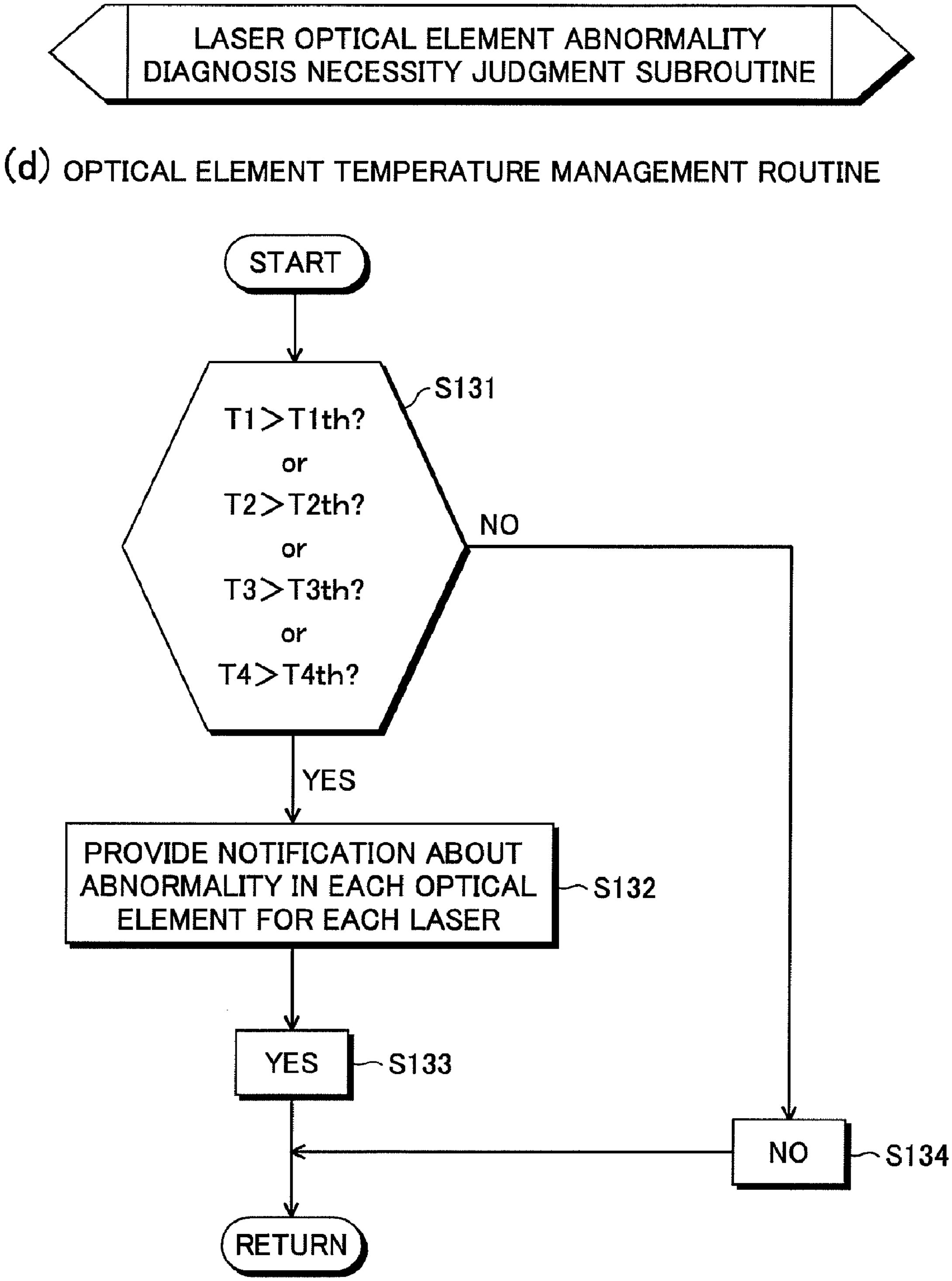
FIG. 33 is a flowchart showing an optical element temperature management routine used in a laser optical element abnormality diagnosis necessity judgment subroutine in a tenth embodiment.

FIG. 33 is a flowchart showing (d) the optical element temperature management routine which is to be added to the laser optical element abnormality diagnosis necessity judgment subroutine (S101).

(d) The optical element temperature management routine is a subroutine managing the temperature of each of the optical elements and determining to carry out the abnormality diagnosis even when only one of the optical elements under temperature management exceeds a predetermined threshold value.

First, it is determined whether or not the temperature T1 of the window 6(1) for the main pulse laser exceeds the threshold value T1th thereof, whether or not the temperature T2 of the parabolic mirror 43(1) for the main pulse laser exceeds the threshold value T2th thereof, whether or not the temperature T3 of the window 6(2) for the pre-pulse laser exceeds the threshold value T3th thereof, or whether or not the temperature T4 of the parabolic mirror 43(2) for the pre-pulse laser exceeds the threshold value T4th thereof (S131). If the temperature in anyone of the optical elements exceeds the threshold value, the operator or the outside equipments such as the exposure unit is notified about abnormality occurrence in the laser optical element (S132). Then, it is determined that the abnormality diagnosis is required (YES) (S133), and the temperature management routine is terminated.

On the other hand, in Step S131, if the temperature values of all the optical elements under the management do not exceed the respective threshold values, it is determined that the abnormality diagnosis is not necessary (NO) (S134), and the temperature management routine is terminated.

(Eleventh Embodiment)

Figure 34:
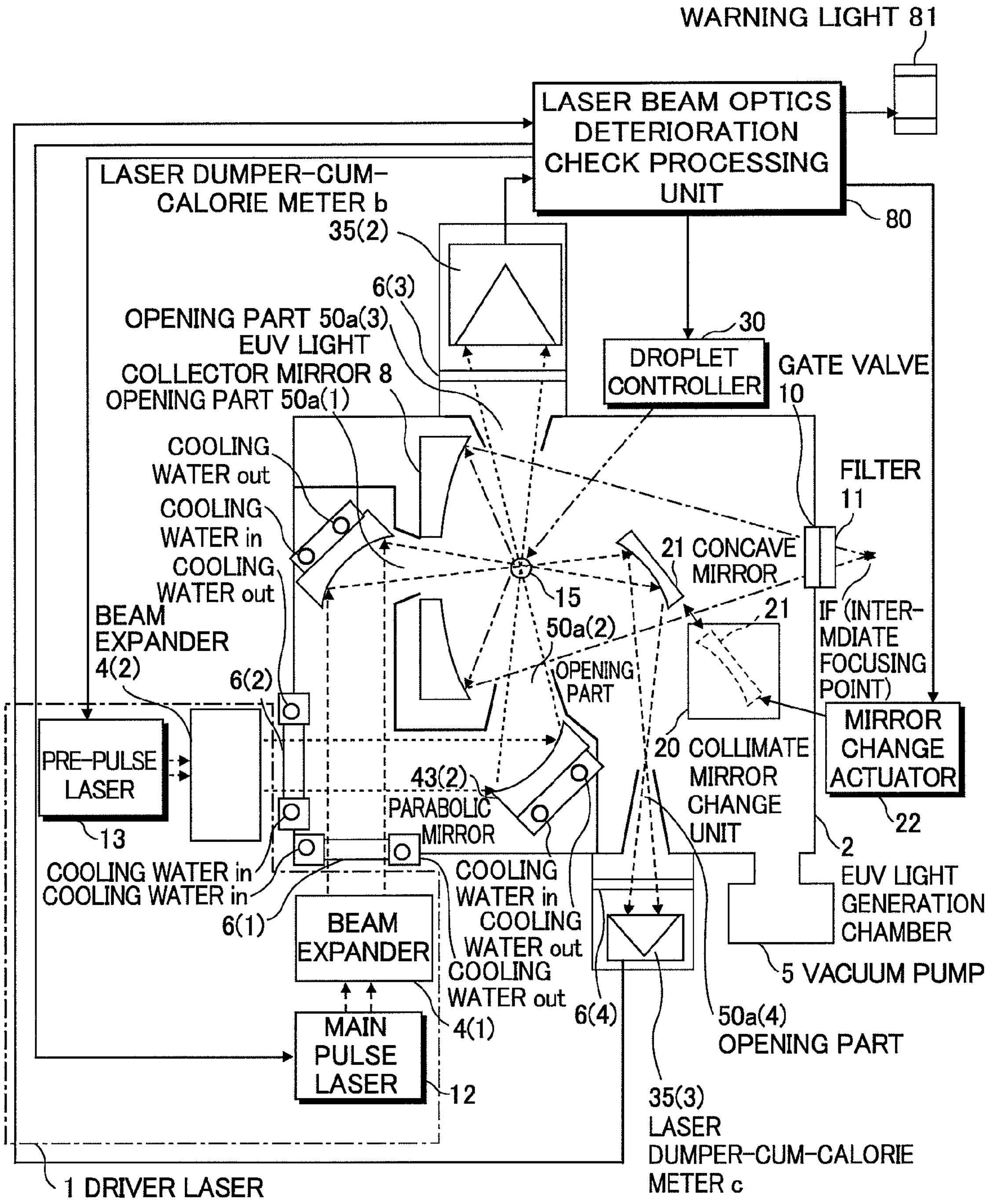
FIG. 34 is a schematic plan view showing an outline of an EUV light source apparatus according to an eleventh embodiment of the present invention.
Figure 35:
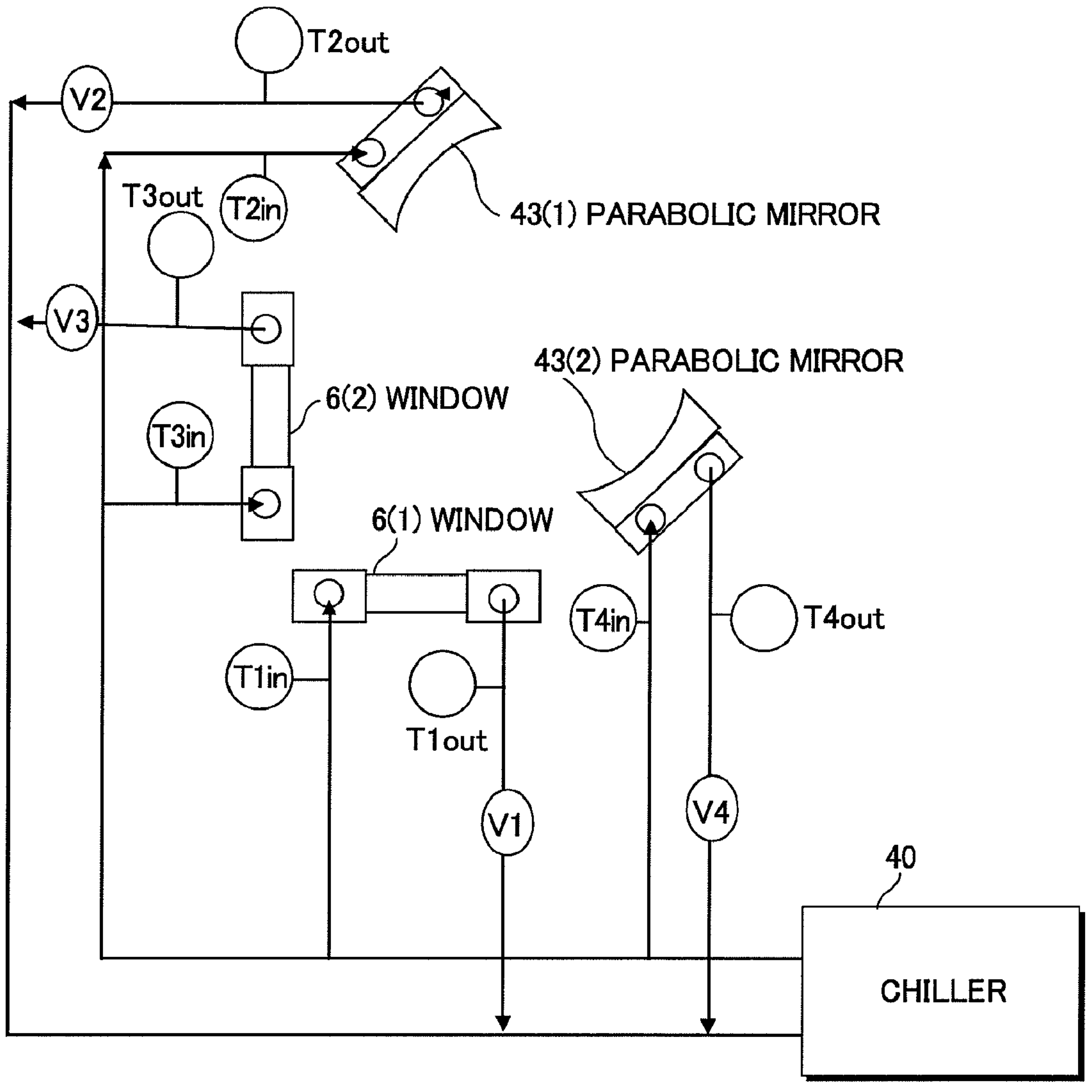
FIG. 35 is a cooling water circulation circuit diagram in the eleventh embodiment.

FIG. 34 is a schematic plan view showing an outline of an EUV light source apparatus according to an eleventh embodiment of the present invention. FIG. 35 is a cooling water circulation circuit diagram in the eleventh embodiment. The Euv light source apparatus of the present embodiment has an advantage that a waste heat amount is managed by use of a cooling water flow for the laser optical elements in the EUV light source apparatus of the ninth embodiment shown in FIG. 29. The other constituents are almost the same.

That is, cooling water is made to flow through the window 6(1) and the parabolic mirror 43(1) for the main pulse laser and the window 6(2) and the parabolic mirror 43(2) for the pre-pulse laser so as to prevent the optical elements from being distorted by thermal stress or the like.

Since the output power of the main pulse laser is 10 kW to 20 kW, the wave front is distorted because of the heat generation even if the surface of the optical element is not deteriorated, and the optical element needs to be cooled for maintaining the beam focusing performance.

Since the output power of the pre-pulse laser is 100 W to 200 W, the optical elements need not to be cooled if the optical elements are not deteriorated by the debris. However, even when the optical element is deteriorated a little bit and absorbs the heat, it is possible to prevent the wave front from being distorted and to maintain the beam focusing performance by the cooling.

Accordingly, it is preferable also for the beam focusing performance to cool the laser optical elements.

As shown in FIG. 35, in the present embodiment, the cooling water output from a chiller 40 is made to branch to be supplied to the respective optical elements in parallel, used for cooling the optical elements, and ejected in parallel to a returning pipe to the chiller 40. For each of the optical elements, inlet temperature of the cooling water Tin (T1in, T2in, T3in, or T4in), outlet temperature of the cooling water Tout (T1out, T2out, T3out, or T4out), and flow amount of the cooling water V (V1, V2, V3, or V4) are measured and the waste heat amount is calculated to detect the state of the deterioration in the optical elements for appropriate management thereof.

Note that, while the drawing illustrates a system in which the cooling water is circulated in parallel for all the related optical elements, the present embodiment is not limited to this example and obviously a serial pipe arrangement or a combination of the serial and parallel pipe arrangements, for example, may be used for all the optical elements. In conclusion, the pipe arrangement may be one that provides a piping route without affecting the beam focusing performances of the main-pulse laser beam and the pre-pulse laser beam and also provides a capability of measuring the temperature at the inlet and the outlet in each of the optical elements and measuring the cooling water flow amount.

Further, in the case that the cooling water amount is the same for all the optical elements by use of the serial pipe arrangement, for example, only the temperature may be measured at the inlet and the outlet in each of the optical elements.

Figure 36:
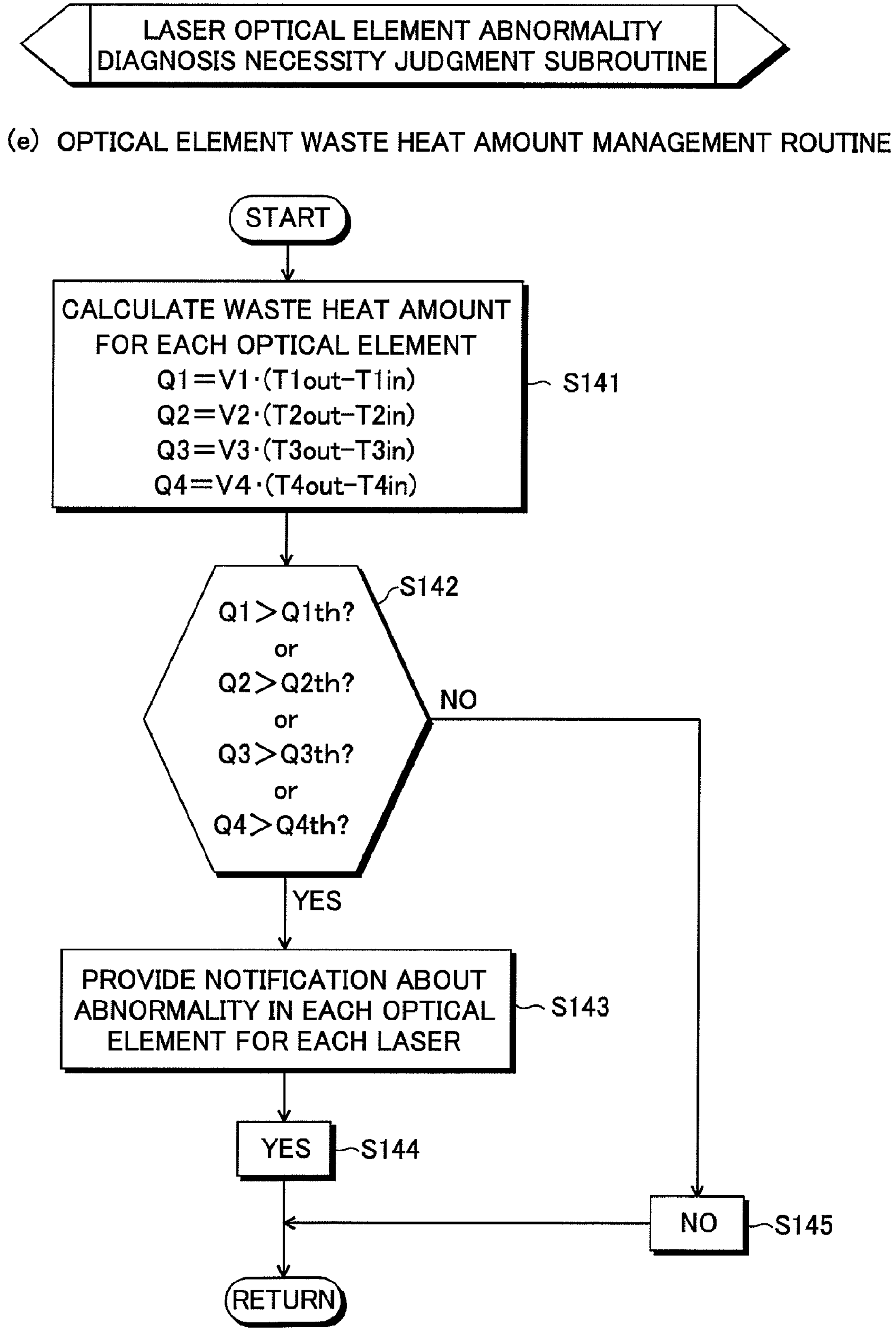
FIG. 36 is a flowchart showing an optical element waste heat amount management routine used in a laser optical element abnormality diagnosis necessity judgment subroutine of the eleventh embodiment.
Figure 37:
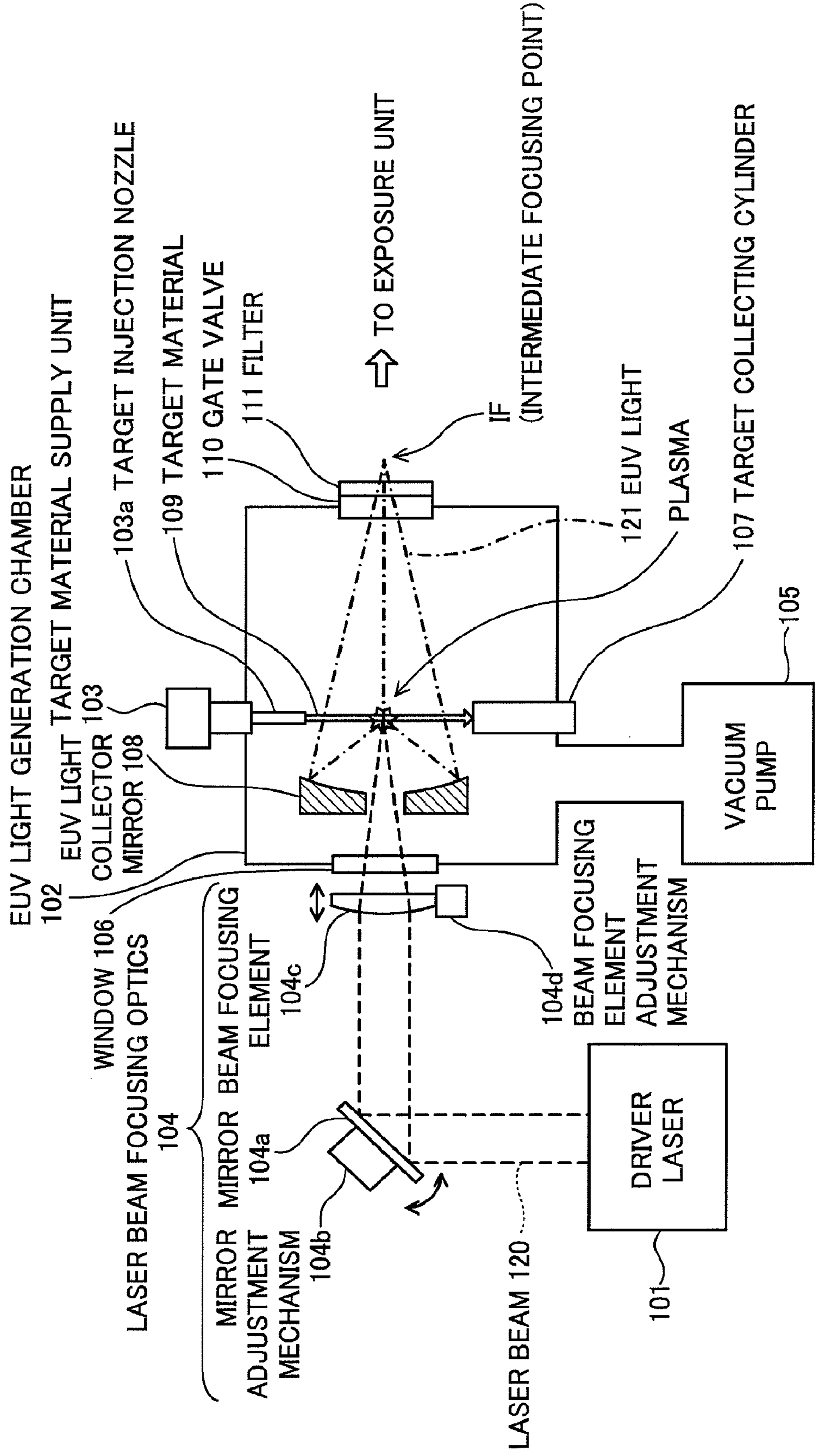
FIG.37 PRIOR ART
FIG. 37 is a diagram showing an outline of a conventional LPP type EUV light source apparatus.

FIG. 36 is a flowchart showing (e) an optical element waste heat amount management routine which is a routine necessary for determining the necessity of the optical element abnormality diagnosis in the laser optical element abnormality diagnosis necessity judgment subroutine (S101) of the eleventh embodiment.

(e) The optical element waste heat amount management routine is a subroutine determining whether or not to carry out the abnormality diagnosis according to the waste heat amount taken out by the cooling water from each of the optical elements. The waste heat amount Q in each of the optical elements can be obtained from the cooling water amount V, the inlet temperature of the cooling water Tin, and the outlet temperature of the cooling water Tout, according to a formula Q=V (Tout−Tin).

First, the waste heat amount Q (Q1, Q2, Q3, or Q4) is obtained for each of the window 6(1) and the parabolic mirror 43(1) for the main pulse laser and the window 6(2) and the parabolic mirror 43(2) for the pre-pulse laser by use of measured values of the cooling water flow amount V, the inlet temperature of the cooling water Tin, and the outlet temperature of the cooling water Tout (S141).

Next, it is determined whether or not the waste heat amount Q1 of the window 6(1) for the main pulse laser exceeds a threshold value thereof Q1th, whether or not the waste heat amount Q2 of the parabolic mirror 43(1) for the main pulse laser exceeds a threshold value thereof Q2th, whether or not the waste heat amount Q3 of the window 6(2) for the pre-pulse laser exceeds a threshold value thereof Q3th, or whether or not the waste heat amount Q4 of the parabolic mirror 43(2) for the pre-pulse laser exceeds a threshold value thereof Q4th (S142). If the waste heat amount in any one of the optical elements exceeds the threshold value thereof, the operator or the outside equipments such as the exposure unit is notified about the abnormality occurrence in the laser optical element (S143), and also it is determined that the abnormality diagnosis is necessary (YES) (S144) and the optical element waste heat amount management routine is terminated.

On the other hand, in Step S142, if the waste heat amount does not exceed the threshold value for each of all the optical elements under management, it is determined that the abnormality diagnosis is not necessary (NO) (S145), and the waste heat amount management routine is terminated.

While, in the above description, each of the inlet temperature Tin and the outlet temperature Tout of the cooling water and the cooling water amount V for each of the optical elements are measured and the diagnosis necessity is judged from the obtained waste heat amount Q, the present embodiment is not limited to this example and the judgment may be carried out according to any measured value corresponding to the waste heat amount.

For example, in the case of supplying the cooling water serially, the flow amount measurement may be carried out at one point. Further, in the case of controlling the flow amount such that the flow amount value becomes a predetermined value, the flow amount measurement is not necessary and the waste heat amount can be managed by use of the temperature difference between the inlet and the outlet of the cooling water.

Further, in the case that the cooling water control is carried out such that all the inlet temperatures of the cooling water and also all the flow amounts for the respective optical elements are the same as each other, the waste heat amount can be managed according to the flow shown in FIG. 33, by use of only the outlet temperature of the cooling water Tout for each of the optical elements.

Moreover, while the main laser beam is focused by the concave mirror 21 and input into the opening part 50*a*(4) in the embodiments shown in FIG. 30, FIG. 32, and FIG. 34, the present invention is not limited to these embodiments, and the main laser beam may be collimated once by this concave mirror and then input into the opening part 50*a*(4) which is made wider a little bit. Further, even in the case that this concave mirror 21 is not a concave mirror but a flat mirror, there is not a problem if the diffused main laser beam can be input into the opening part 50*a*(4) and the laser dumper-cum-calorie meter 35(3). In this manner, any optical element may be used as far as the main laser beam is once reflected and input into the laser dumper-cum-calorie meter. Note that, in the case that the main laser beam is once focused by the concave mirror 21 and input into the small opening part 50*a*(4) as in the embodiments shown in FIG. 30, FIG. 32, and FIG. 34, it is possible to obtain a bigger advantage of preventing the window 6(4) from being stained with the debris. In addition, also in the case of the pre-pulse laser beam, another optical element may be used for introducing the pre-pulse laser beam into the laser dumper-cum-calorie meter.

The invention claimed is:

1. An extreme ultraviolet light source apparatus for generating extreme ultraviolet light by irradiating a target material supplied to a region with a laser beam and thereby turning said target material into plasma, said apparatus comprising:

- an extreme ultraviolet light generation chamber including said region therein;
- a target material supply unit for supplying the target material;
- optics for introducing the laser beam from an outside of said extreme ultraviolet light generation chamber to said region;
- a first laser beam detector for detecting the laser beam which has passed through said region;
- a processing unit for judging deterioration of said optics according to a detection result of said first laser beam detector; and
- a display unit for displaying judgment result of said processing unit.

2. The extreme ultraviolet light source apparatus according to claim 1, further comprising:

a shield for shielding between said region and said first laser beam detector at least in a period where said target material is irradiated with the laser beam.

3. The extreme ultraviolet light source apparatus according to claim 1, further comprising:

a temperature sensor at a part of said optics, wherein said processing unit judges deterioration of said optics according to a detection result of said temperature sensor.

4. The extreme ultraviolet light source apparatus according to claim 1, wherein said first laser beam detector is disposed outside said extreme ultraviolet light generation chamber, and at least one optical element is disposed within said extreme ultraviolet light generation chamber, and introduces the laser beam, which has passed through said region, into said first laser beam detector.

5. The extreme ultraviolet light source apparatus according to claim 1, wherein the laser beam passes through said region when said target material supply unit does not supply said target material.

6. The extreme ultraviolet light source apparatus according to claim 1, wherein the laser beam passes through said region by adjusting at least one of injection timing of said target material from said target material supply unit and emission timing of the laser beam from said driver laser.

7. The extreme ultraviolet light source apparatus according to claim 1, wherein the laser beam passes through said region by adjusting at least one of a trajectory of said target material from said target material supply unit and an optical path of the laser beam.

8. The extreme ultraviolet light source apparatus according to claim 1, further comprising a driver laser for emitting the laser beam.

9. The extreme ultraviolet light source apparatus according to claim 8, wherein said driver laser includes a $CO_2$ laser.

10. The extreme ultraviolet light source apparatus according to claim 1, wherein said extreme ultraviolet light generation chamber includes a purge gas supply unit.

11. The extreme ultraviolet light source apparatus according to claim 10, wherein said extreme ultraviolet light generation chamber comprises a debris shield having an opening directed toward said region.

12. The extreme ultraviolet light source apparatus according to claim 1, wherein said display unit comprises a warning light.

13. The extreme ultraviolet light source apparatus according to claim 1, wherein said display unit comprises a display device including LCD (liquid crystal display).

14. The extreme ultraviolet light source apparatus according to claim 1, wherein said optics has a cooling device for an optical element.

15. The extreme ultraviolet light source apparatus according to claim 1, wherein said first laser beam detector includes a calorie meter.

16. The extreme ultraviolet light source apparatus according to claim 1, wherein said first laser beam detector includes an area sensor.

17. The extreme ultraviolet light source apparatus according to claim 16, wherein said area sensor includes one of a CCD (charge coupled device) and CMOS (complimentary metal oxide semiconductor) sensor.

18. The extreme ultraviolet light source apparatus according to claim 16, wherein said area sensor has focusing optics.

19. The extreme ultraviolet light source apparatus according to claim 16, wherein said area sensor has a filter.

20. The extreme ultraviolet light source apparatus according to claim 16, further comprising a beam splitter for splitting the laser beam which has passed through said region.

21. The extreme ultraviolet light source apparatus according to claim 16, wherein said optics includes a laser beam focusing optics.

22. The extreme ultraviolet light source apparatus according to claim 21, wherein said processing unit judges at least one of deterioration and distortion of at least one optical element of said laser beam focusing optics or judges a shift of a focal point of the laser beam focused by said laser beam focusing optics from a position where the plasma is to be generated, based on an image of the laser beam detected by said area sensor.

23. The extreme ultraviolet light source apparatus according to claim 21, wherein said laser beam focusing optics includes at least one laser beam focusing mirror.

24. The extreme ultraviolet light source apparatus according to claim 21, wherein said laser beam focusing optics includes at least one laser beam focusing lens.

25. The extreme ultraviolet light source apparatus according to claim 1, wherein said optics has a window.

26. The extreme ultraviolet light source apparatus according to claim 25, further comprising:

a beam splitter for splitting the laser beam before the laser beam passes through said window; and a second laser beam detector for detecting a laser beam split by said beam splitter, wherein said processing unit judges deterioration of said optics according to a detection result of said second laser beam detector as well as the detection result of said first laser beam detector.

27. An extreme ultraviolet light source apparatus for generating extreme ultraviolet light by irradiating a target material at a region with a pre-pulse laser beam and further irradiating the target material with a main pulse laser beam, said apparatus comprising:

an extreme ultraviolet light generation chamber including said region therein;

a target material supply unit for supplying the target material toward the region;

optics for introducing the pre-pulse laser beam and the main pulse laser beam from an outside of said extreme ultraviolet light generation chamber to said region, said optics including a window;

a first beam splitter for splitting the main pulse laser beam before the main pulse laser beam passes through said window;

a first laser beam detector for detecting a split main pulse laser beam;

a second beam splitter for splitting the pre-pulse laser beam before the pre-pulse laser beam passes thought said window;

a second laser beam detector for detecting a split pre-pulse laser beam;

a processing unit for judging deterioration of said optics according to a detection result of at least one of said first and second laser beam detectors; and a display unit for displaying judgment result of said processing unit.

* * * * *